US012630870B2

(12) United States Patent
Kim et al.

(10) Patent No.: US 12,630,870 B2
(45) Date of Patent: May 19, 2026

(54) PARTITION-FREE DIGITAL PCR (dPCR) SYSTEM

(71) Applicant: Canon Virginia, Inc., Newport News, VA (US)

(72) Inventors: Hanyoup Kim, Pleasanton, CA (US); Julia Pittaluga, Virginia Beach, VA (US); Joseph Myrick, West Point, VA (US); Jeremy Schreiber, Williamsburg, VA (US); Scott Sundberg, Yorktown, VA (US); Yoichi Murakami, Newport News, VA (US)

(73) Assignee: Canon Virginia, Inc., Newport News, VA (US)

( * ) Notice: Subject to any disclaimer, the term of this patent is extended or adjusted under 35 U.S.C. 154(b) by 1122 days.

(21) Appl. No.: 16/749,919

(22) Filed: Jan. 22, 2020

(65) Prior Publication Data

US 2020/0232020 A1 Jul. 23, 2020

Related U.S. Application Data

(60) Provisional application No. 62/947,393, filed on Dec. 12, 2019, provisional application No. 62/795,392, filed on Jan. 22, 2019.

(51) Int. Cl.
*C12Q 1/6851* (2018.01)
*C12Q 1/686* (2018.01)
(Continued)

(52) U.S. Cl.
CPC ........... *C12Q 1/6851* (2013.01); *C12Q 1/686* (2013.01); *G01N 21/6456* (2013.01);
(Continued)

(58) Field of Classification Search
None
See application file for complete search history.

(56) References Cited

U.S. PATENT DOCUMENTS 8,741,570 B2 6/2014 Duhr
9,399,217 B2 7/2016 Esfandyarpour
(Continued)

FOREIGN PATENT DOCUMENTS

JP 2013-236613 A 11/2013
JP 2015-053893 A 3/2015
(Continued)

OTHER PUBLICATIONS

Kim, J. et al., Multiplex real-time PCR using temperature sensitive primer-supplying hydrogel particles and its application for malaria species dentification, PLOS ONE, vol. 13, ee0190451, pp. 1-12 (Year: 2018).*

(Continued)

*Primary Examiner* — Aaron A Priest
*Assistant Examiner* — Tian Yu
(74) *Attorney, Agent, or Firm* — Canon U.S.A., Inc., IP Division

(57) ABSTRACT

The present disclosure relates to methods and systems for partition-free quantification of molecules. The methods and systems provided allow a sample to be amplified such that discrete amplification spots can be analyzed to quantify the number of molecules without requiring physical partitions in order to separate the amplification spots.

29 Claims, 64 Drawing Sheets

(51) Int. Cl.

| | |
|---|---|
| *G01N 21/64* | (2006.01) |
| *G01N 25/04* | (2006.01) |
| *G16B 20/10* | (2019.01) |
| *G16B 20/20* | (2019.01) |
| *G16B 25/20* | (2019.01) |
| *G16B 40/00* | (2019.01) |

(52) U.S. Cl.
CPC ............. *G01N 25/04* (2013.01); *G16B 20/10* (2019.02); *G16B 20/20* (2019.02); *G16B 25/20* (2019.02); *G16B 40/00* (2019.02)

(56) References Cited

U.S. PATENT DOCUMENTS

| | | |
|---|---|---|
| 2016/0051985 A1 | 2/2016 | Knight et al. |
| 2017/0065977 A1 | 3/2017 | Esfandyarpour et al. |

FOREIGN PATENT DOCUMENTS

| | | |
|---|---|---|
| WO | 2013/165748 A1 | 11/2013 |
| WO | 2016/170109 A1 | 10/2016 |
| WO | 2018/125835 A1 | 7/2018 |

OTHER PUBLICATIONS

Hatch, A.C. et al., 1-Million droplet array with wide-field fluorescence imaging for digital PCR, Lab on a Chip, vol. 11, pp. 3838-3845 (Year: 2011).*

Drobyshev, A. L. et al., The role of DNA diffusion in solid phase polymerase chain reaction with gel-immobilized primers in planar and capillary microarray format, Biomicrofluidics, vol. 3, 04412, pp. 1-12 (Year: 2009).*

Lin et al., Digital Loop-Mediated Isothermal Amplification on a Commercial Membrane. ACS Sens. Jan. 25, 2019;4(1):242-249. doi: 10.1021/acssensors.8b01419. Epub Jan. 15, 2019. PMID: 30604619; PMCID: PMC6350201. (Year: 2019).*

Polyvinylpyrrolidone(PVP)—Wikipedia; Archived Mar. 23, 2018 on WaybackMachine (Year: 2018).*

Son, J., Cho, B., Hong, S. et al. Ultrafast photonic PCR. Light Sci Appl 4, e280 (2015). doi.org/10.1038/lsa.2015.53 (Year: 2015).*

Huang et al., Smartphone-Based in-Gel Loop-Mediated Isothermal Amplification (gLAMP) System Enables Rapid Coliphage MS2 Quantification in Environmental Waters. Environ Sci Technol. Jun. 5, 2018;52(11):6399-6407. doi: 10.1021/acs.est.8b00241. Epub May 16, 2018. PMID: 29738236; PMCID: PMC5990930. (Year: 2018).*

Diffusion Coefficient—Multiphysics Cyclopedia. COMSOL. (Published online Jan. 14, 2015). www.comsol.de/multiphysics/diffusion-coefficient (Year: 2015).*

Li et al. Selective detection of individual DNA molecules by capillary polymerase chain reaction. Anal Chem. Apr. 1, 2001;73(7):1537-43. doi: 10.1021/ac001125p. PMID: 11321306 (Year: 2001).*

Huang et al. Smartphone-Based in-Gel Loop-Mediated Isothermal Amplification (gLAMP) System Enables Rapid Coliphage MS2 Quantification in Environmental Waters. Environ Sci Technol. Jun. 5, 2018;52(11):6399-6407. doi: 10.1021/acs.est.8b00241. Epub May 16, 2018. (Year: 2018).*

Full width at half maximum—Wikipedia; Archived Jul. 21, 2017 on WaybackMachine (Year: 2017).*

Samwer, Matthias et al.; DNA Cross-Bridging Shapes a Single Nucleus from a Set of Mitotic Chromosomes; Cell, vol. 170, Issue 5, 956-972.e23; 2017 (Year: 2017).*

Singh et al. mitoBKCa is encoded by the Konma1 gene, and a splicing sequence defines its mitochondrial location, Proc. Natl. Acad. Sci. U.S.A. 110 (26) 10836-10841, doi.org/10.1073/pnas. 1302028110 (2013) (Year: 2013).*

Hatch, A., et al., "1-Million droplet array with wide-field fluorescence imaging for digital PCR", Lab on a Chip, 2011, No. 11, pp. 3838-3845.

Wikipedia.com, "Convection", Jan. 10, 2019.

Wikipedia.com, "Digital Polymerase Chain Reaction", Sep. 23, 2018.

Nie, B., et al., "Scoring Single-Nucleotide Polymorphisms at the Single-Molecule Level by Counting Individual DNA Cleavage Events on Surfaces", Anal. Chem., Oct. 15, 2005, vol. 77, No. 20, pp. 6594-6600.

Jarvius, J., et al., "Digital quantification using amplified single-molecule detection", Nature Methods, Sep. 1, 2006, vol. 3, No. 9, pp. 725-727.

Krishnan, M., et al., "Theoretical considerations for counting nucleic acid molecules in microdevices", J. Micromech. Microeng., Jan. 1, 2005, vol. 15, No. 1, pp. N6-N10.

Li, H., et al., "Selective Detection of Individual DNA Molecules by Capillary Polymerase Chain Reaction", Anal. Chem., Feb. 27, 2001, vol. 73, No. 7, pp. 1537-1543.

Morinishi, L.S., et al., "Simple Bulk Readout of Digital Nucleic Acid Quantification Assays", J. Vis. Exp., Sep. 24, 2015, vol. 3791, No. 103, pp. e52925: 1-9.

Zhang, C., et al., "Single-Molecule DNA Amplification and Analysis Using Microfluidics", Chem. Rev., Aug. 11, 2010, vol. 110, No. 8, pp. 4910-4947.

Fraley, S. I., et al., "Universal digital high-resolution melt: a novel approach to broad-based profiling of heterogeneous biological samples", Nucleic Acids Research, Aug. 9, 2013, vol. 41, No. 18, pp. e175: 1-13.

Xu, L., et al., "Virtual microfluids for digital quantification and single-cell sequencing", Nature Methods, Sep. 1, 2016, vol. 13, No. 9, pp. 759-762.

Jarvius, J., et al., "Supplementary Methods for "Digital quantification using amplified single-molecule detection"", Nature Methods, Aug. 23, 2006, retrieved from the Internet: https://www.nature.com/articles/nmeth916#Sec2.

Xu, L., et al., "Virtual microfluidics for digital quantification and single-cell sequencing," Nature Methods, Sep. 2016, pp. 759-762, vol. 13, No. 9.

* cited by examiner

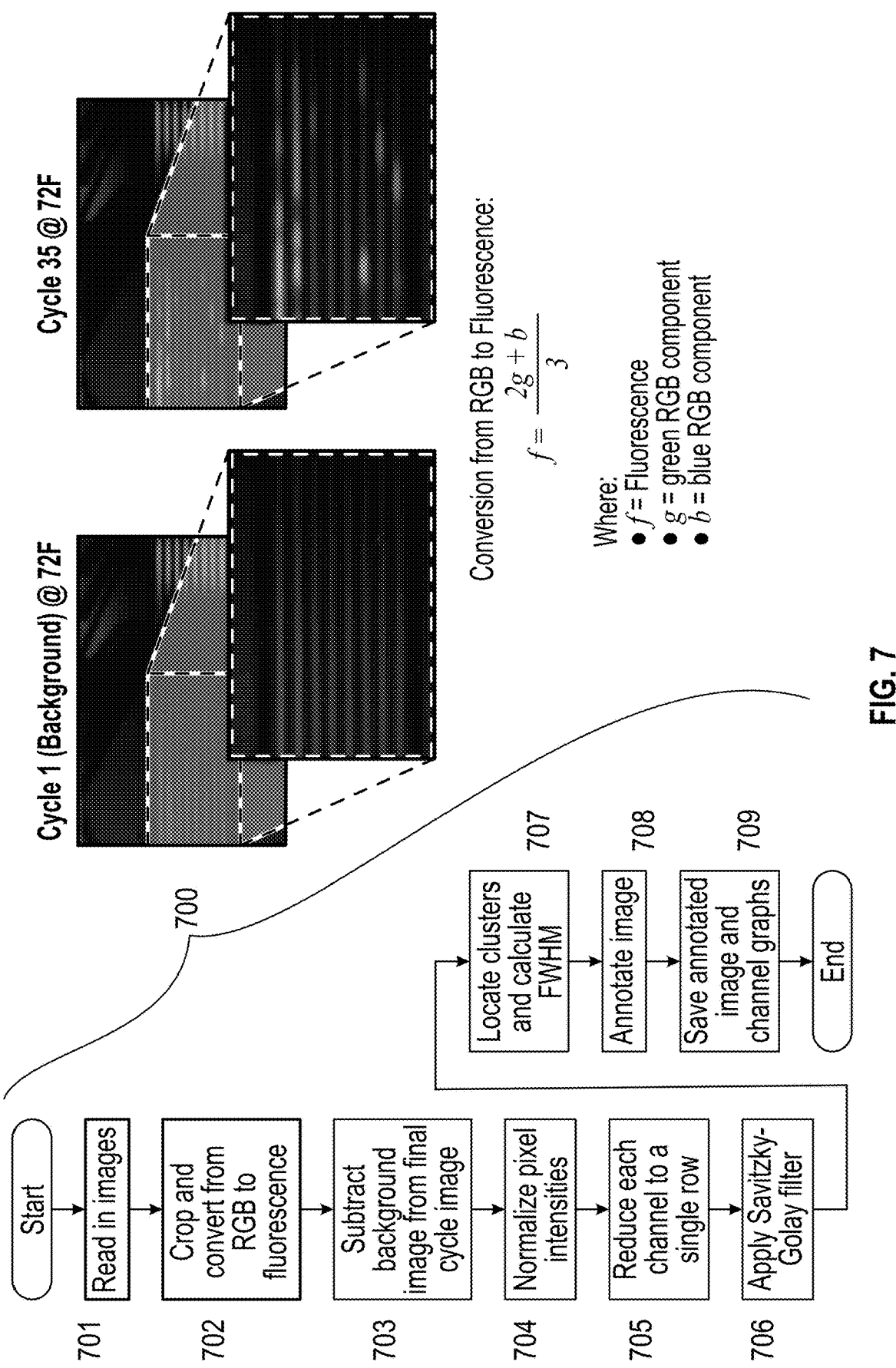

Cycle 1 (Background) @ 72F

Cycle 35 @ 72F

Conversion from RGB to Fluorescence:

$$f = \frac{2g + b}{3}$$

Where:
- $f$ = Fluorescence
- $g$ = green RGB component
- $b$ = blue RGB component

700

Start

Read in images — 701

Crop and convert from RGB to fluorescence — 702

Subtract background image from final cycle image — 703

Normalize pixel intensities — 704

Reduce each channel to a single row — 705

Apply Savitzky-Golay filter — 706

Locate clusters and calculate FWHM — 707

Annotate image — 708

Save annotated image and channel graphs — 709

End

FIG. 7

Figure 10:
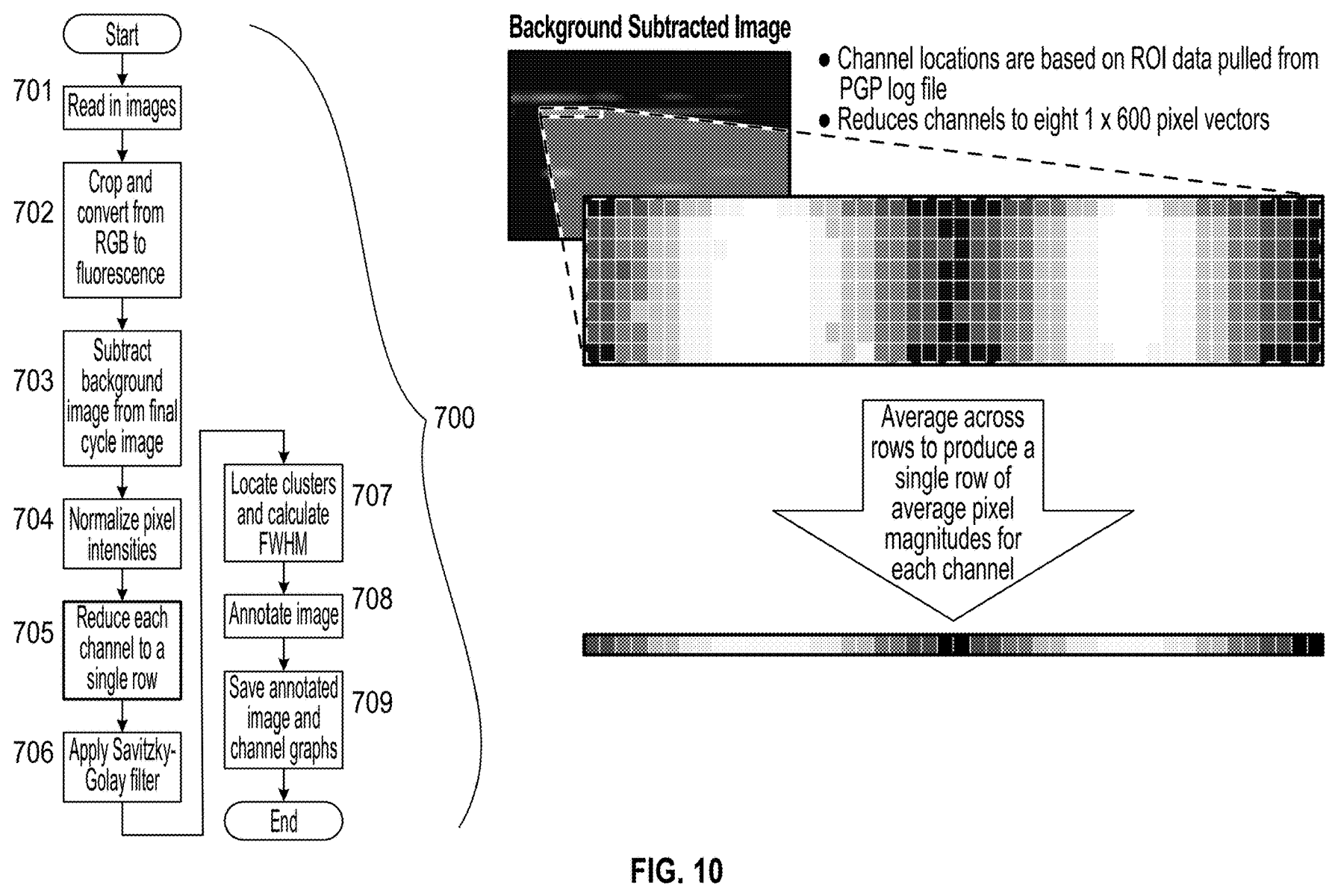

Background Subtracted Image

- Channel locations are based on ROI data pulled from PGP log file
- Reduces channels to eight 1 x 600 pixel vectors Average across rows to produce a single row of average pixel magnitudes for each channel

Start

701  Read in images

702  Crop and convert from RGB to fluorescence

703  Subtract background image from final cycle image

704  Normalize pixel intensities

705  Reduce each channel to a single row

706  Apply Savitzky-Golay filter

707  Locate clusters and calculate FWHM

708  Annotate image

709  Save annotated image and channel graphs

End

The Savitzky-Golay filter knocks down any remaining noise in the channels, producing a smooth curve suitable for analysis.

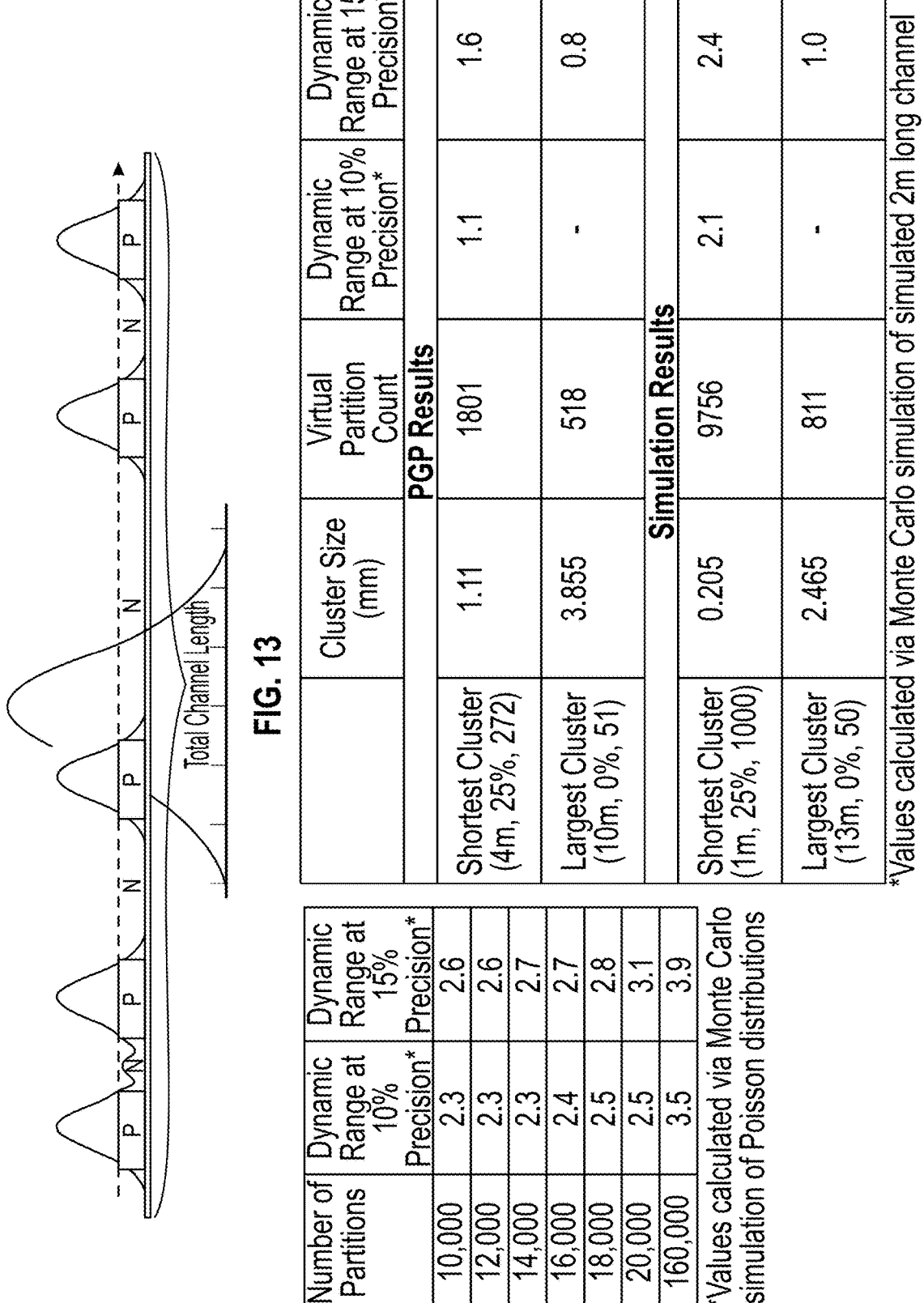

FIG. 13

| Number of Partitions | Dynamic Range at 10% Precision* | Dynamic Range at 15% Precision* |
|---|---|---|
| 10,000 | 2.3 | 2.6 |
| 12,000 | 2.3 | 2.6 |
| 14,000 | 2.3 | 2.7 |
| 16,000 | 2.4 | 2.7 |
| 18,000 | 2.5 | 2.8 |
| 20,000 | 2.5 | 3.1 |
| 160,000 | 3.5 | 3.9 |

*Values calculated via Monte Carlo simulation of Poisson distributions

| | Cluster Size (mm) | Virtual Partition Count | Dynamic Range at 10% Precision* | Dynamic Range at 15% Precision* |
|---|---|---|---|---|
| PGP Results | | | | |
| Shortest Cluster (4m, 25%, 272) | 1.11 | 1801 | 1.1 | 1.6 |
| Largest Cluster (10m, 0%, 51) | 3.855 | 518 | - | 0.8 |
| Simulation Results | | | | |
| Shortest Cluster (1m, 25%, 1000) | 0.205 | 9756 | 2.1 | 2.4 |
| Largest Cluster (13m, 0%, 50) | 2.465 | 811 | - | 1.0 |

*Values calculated via Monte Carlo simulation of simulated 2m long channel

FIG. 14

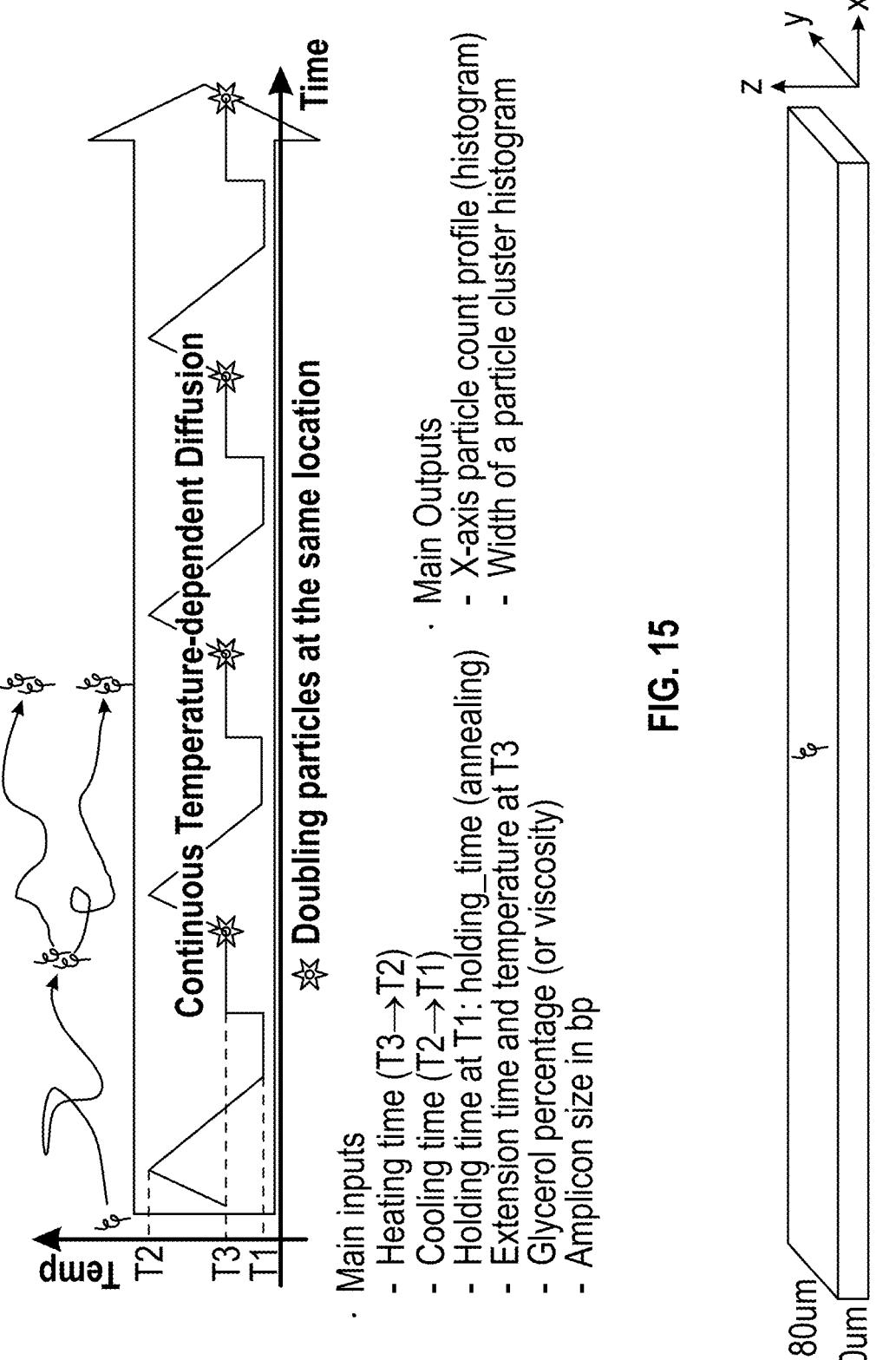

Continuous Temperature-dependent Diffusion

☆ Doubling particles at the same location

· Main inputs
 - Heating time (T3→T2)
 - Cooling time (T2→T1)
 - Holding time at T1: holding_time (annealing)
 - Extension time and temperature at T3
 - Glycerol percentage (or viscosity)
 - Amplicon size in bp · Main Outputs
 - X-axis particle count profile (histogram)
 - Width of a particle cluster histogram

$$D = \frac{kT}{b\pi\Upsilon\eta} = \frac{k}{b\pi} \times \frac{1}{\Upsilon} \times \frac{1}{\mu} \times (T_{celcius} + 273) = C_0 \times \boxed{[f([bp])]} \times \boxed{\frac{1}{\mu(T_{celcius}, C_{glycerol\%})}} \times (T_{celcius} + 273)$$

$C_0$ : constant $= 1.64 \times 10^{-9} \dfrac{mm^2 \bullet Pa}{K}$ $f([bp]) \propto ([bp])^{-0.72}$ : empirical relationship from Lukacs et al. 2000

$\mu(T_{celcius}, C_{glycerol\%})$ = (glycerol or additive contribution) × (PCR mix temperature dependency)

$= \dfrac{\textit{viscosity of x\% glycerol in water}}{\textit{viscosity of 0\% glycerol in water}}$ × (linear fit of viscosity of PCR mix)

$= \dfrac{\textit{viscosity of x\% glycerol in water}}{\textit{viscosity of 0\% glycerol in water}} \times \left(0.001 + \dfrac{(0.00061 - 0.001)}{(95-60)}(T_{celcius}, -60)\right)$

| Glycerol % Wt. | Temperature, °C. | | | | | | |
| --- | --- | --- | --- | --- | --- | --- | --- |
| | 0 | 10 | 20 | 30 | 40 | 50 | 60 |
| | Viscosity, Centipoises | | | | | | |
| 0* | 1.792 | 1.308 | 1.005 | 0.8007 | 0.6560 | 0.5494 | 0.4688 |
| 10 | 2.44 | 1.74 | 1.31 | 1.03 | 0.826 | 0.680 | 0.575 |
| 20 | 3.44 | 2.41 | 1.76 | 1.35 | 1.07 | 0.879 | 0.731 |
| 30 | 5.14 | 3.49 | 2.50 | 1.87 | 1.46 | 1.16 | 0.956 |

Segur et al. 1951

| | Temperature (°C) | Viscosity (Pas) |
| --- | --- | --- |
| PCR solution Experiment | 25 | 0.0019 |
| PCR solution Experiment | 60 | 0.0010 |
| PCR solution Experiment | 95 | 0.00061 |
| 24 Tachibana et al. 2015 | | |

FIG. 17

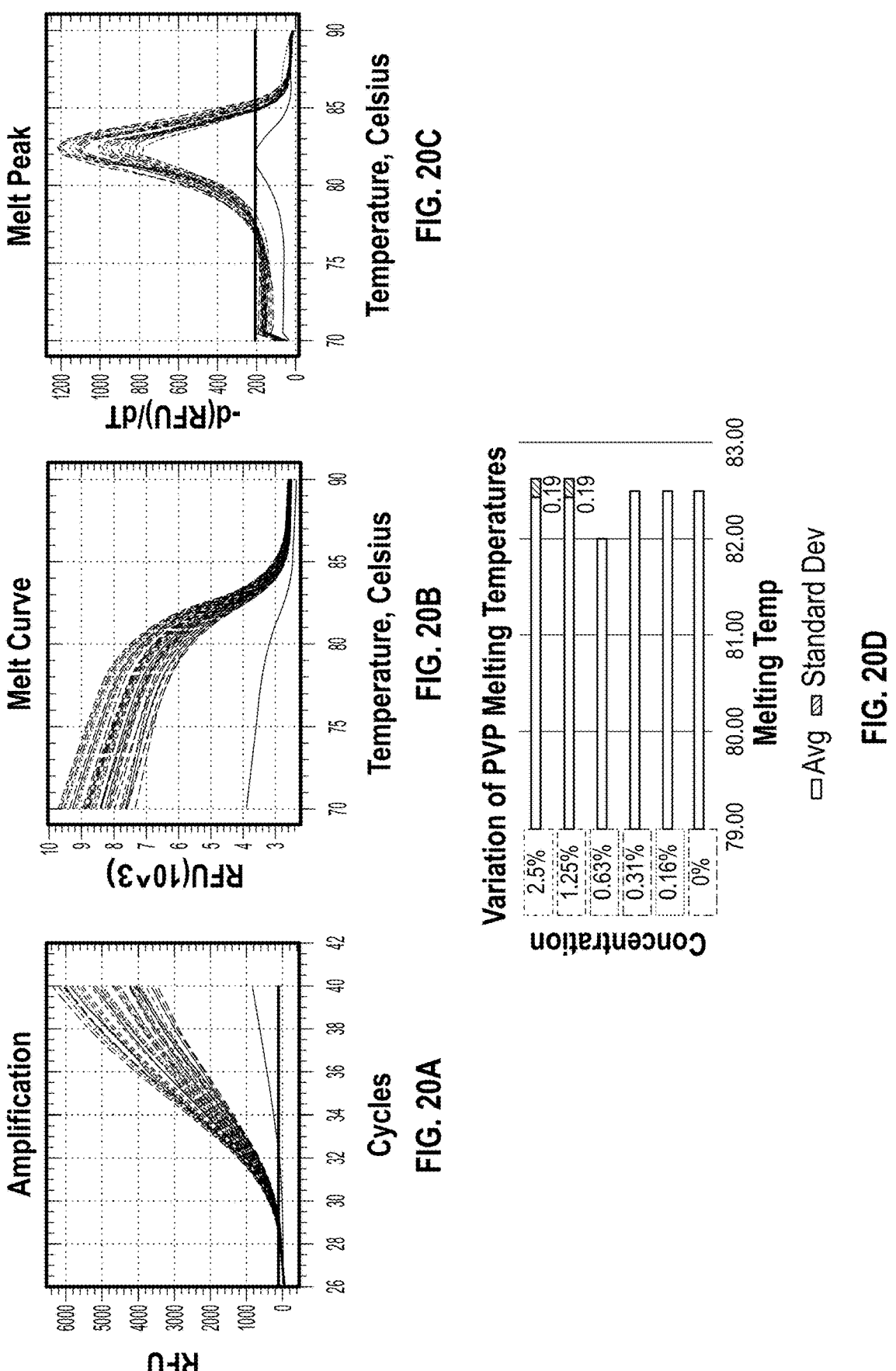

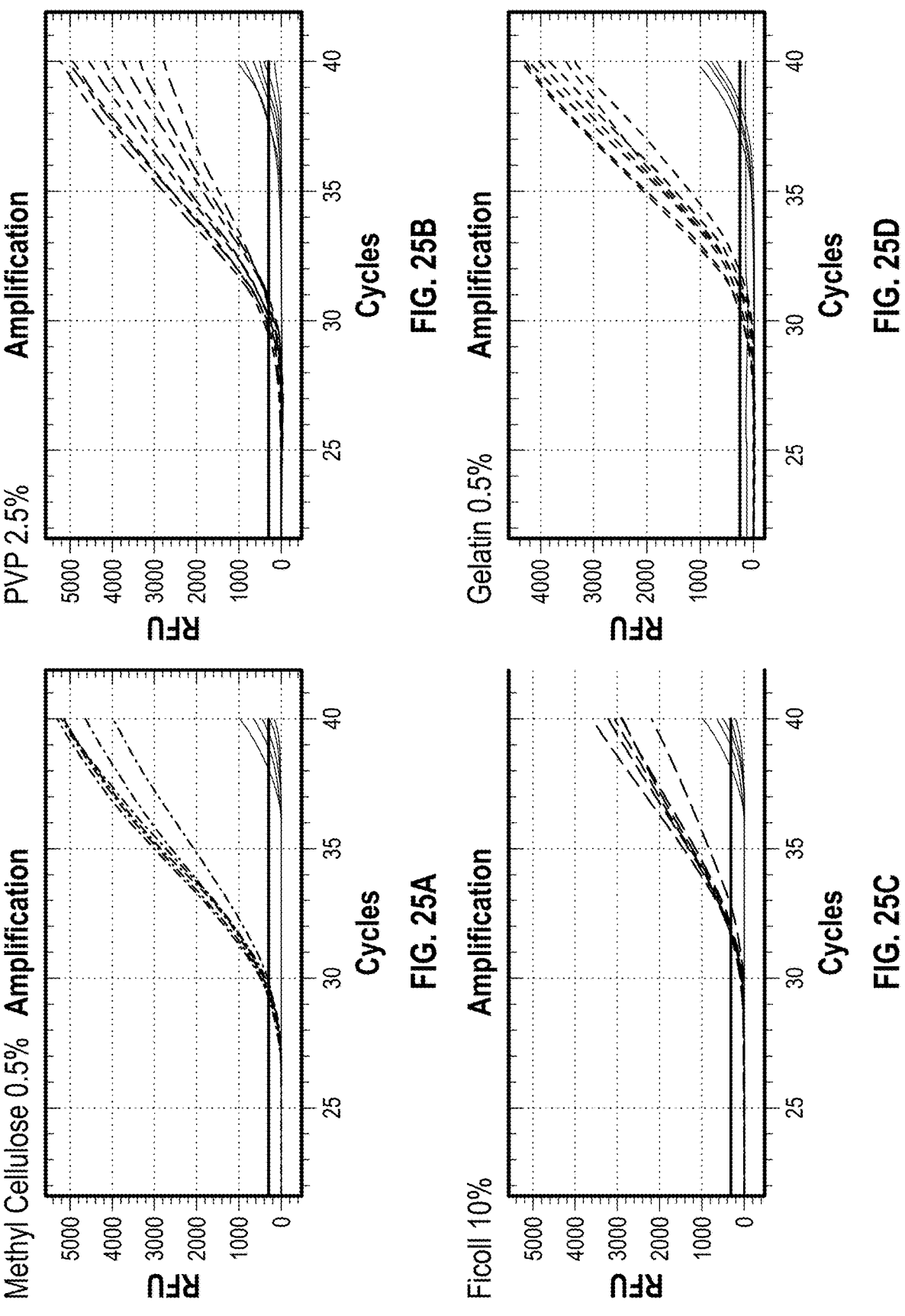

1: LOW    5: LOW
2: LOW    6: LOW
3: LOW    7: PVP HIGH
4: LOW    8: 0 PVP HIGH

PVP 100 bp 10 MIN 0.5ng/µL PVP

0% GLYCEROL DOE

25% GLYCEROL DOE

*MTHFR1286*
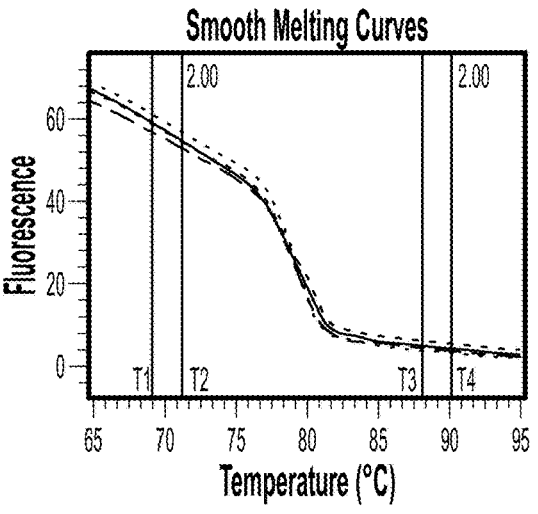
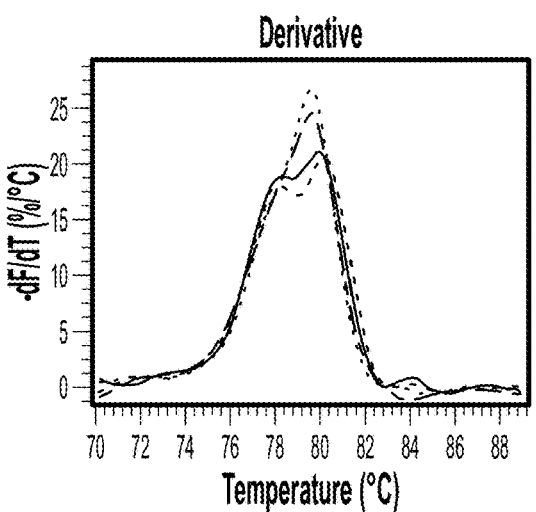
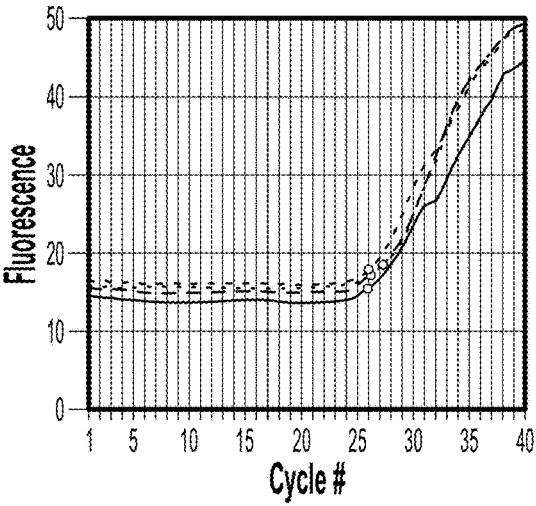
| ☑ Ch1 | ☑ Ch2 | ☑ Ch3 | ☑ Ch4 |
|-------|-------|-------|-------|
| ☐ Ch5 | ☐ Ch6 | ☐ Ch7 | ☐ Ch8 |
○ Denature  ○ Arrival  ◉ Extension
Cq Values
| CH1 | CH2 | CH3 | CH4 | CH5 | CH6 | CH7 | CH8 |
|------|------|------|------|------|------|------|------|
| 25.88 | 26.10 | 25.96 | 27.37 | 22.11 | 23.12 | 20.44 | 21.41 |
3 min PCR
FIG. 32A-C

*MTHFR1286*
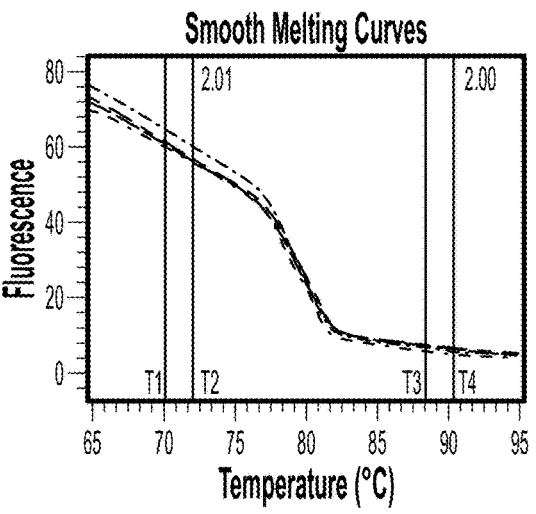
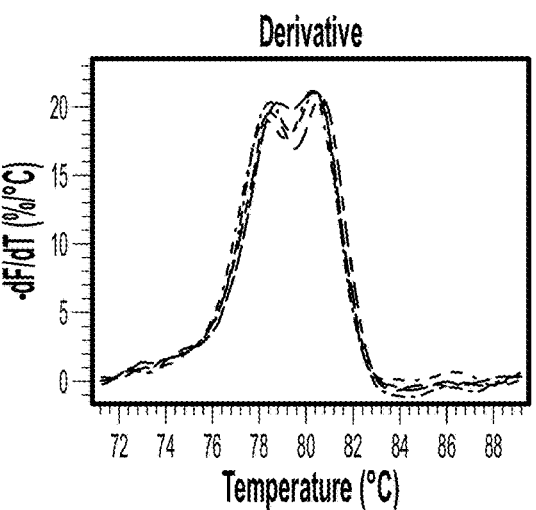
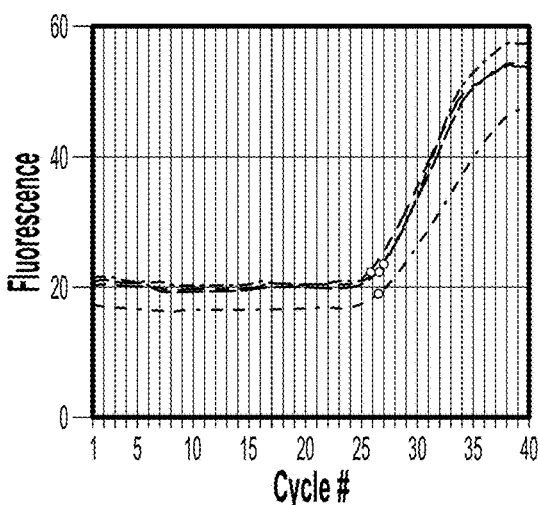
| CH1 | CH2 | CH3 | CH4 | CH5 | CH6 | CH7 | CH8 |
|------|------|------|------|------|------|------|------|
| 33.50 | 35.60 | 11.63 | 10.05 | 25.37 | 26.63 | 25.72 | 26.38 |
2 min PCR
FIG. 32D-F

*MTHFR665*
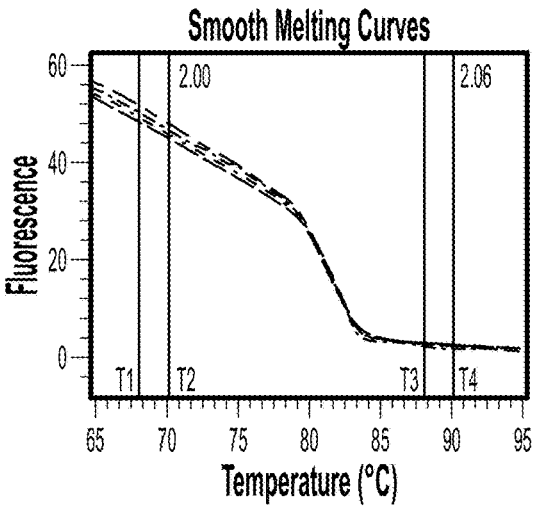
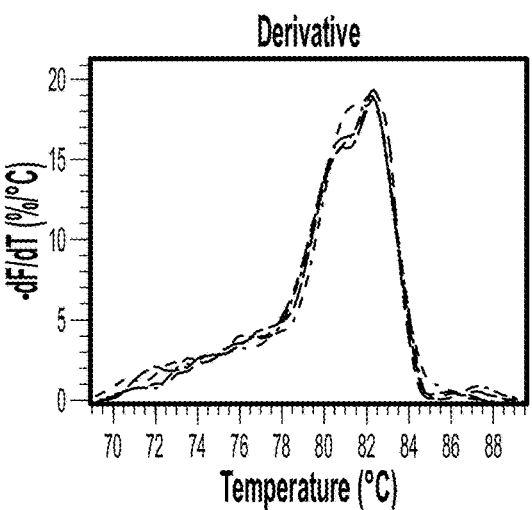
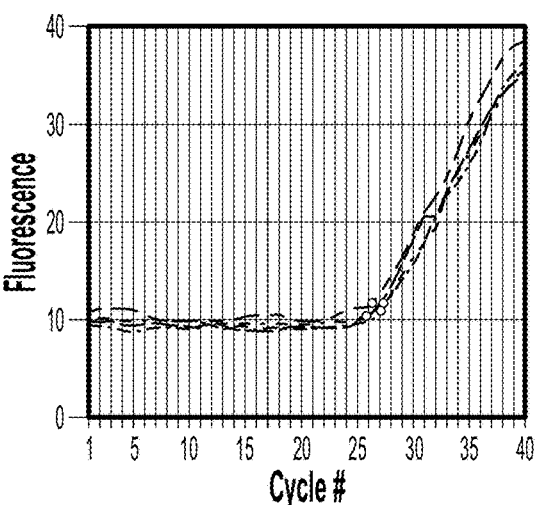
Cq Values
| CH1 | CH2 | CH3 | CH4 | CH5 | CH6 | CH7 | CH8 |
|-----|-----|-----|-----|-----|-----|-----|-----|
| 14.18 | 38.00 | 7.43 | 45.00 | 25.73 | 27.11 | 26.27 | 27.20 |
3 min PCR
FIG. 32G-I

*MTHFR665*
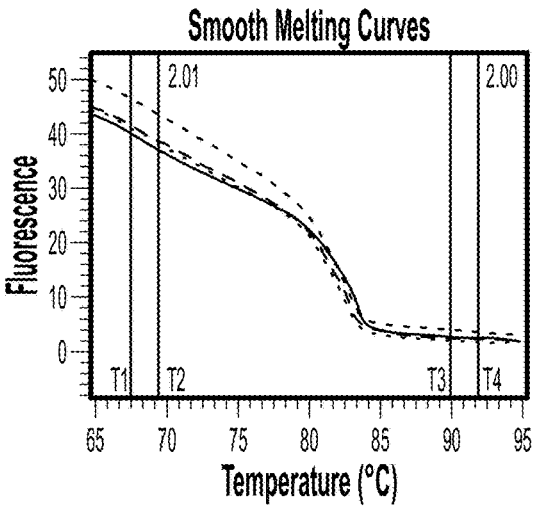
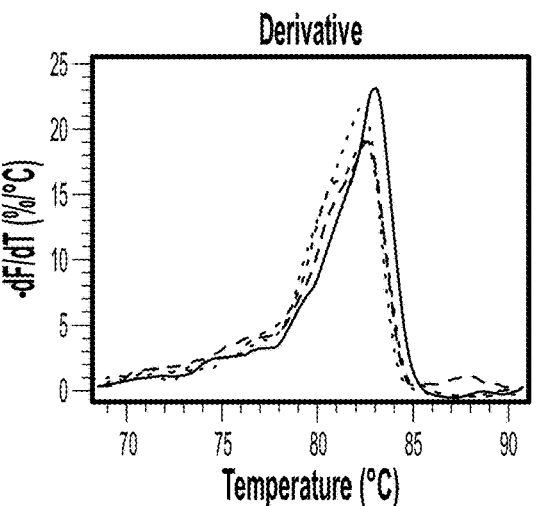
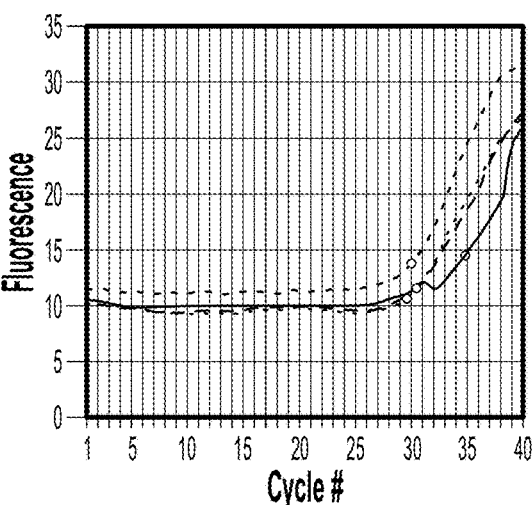
| CH1 | CH2 | CH3 | CH4 | CH5 | CH6 | CH7 | CH8 |
|-------|-------|-------|-------|-------|-------|-------|-------|
| 34.67 | 29.53 | 29.92 | 30.20 | 25.94 | 39.00 | 40.00 | 27.30 |
2 min PCR
FIG. 32J-L

*MTHFR1286*
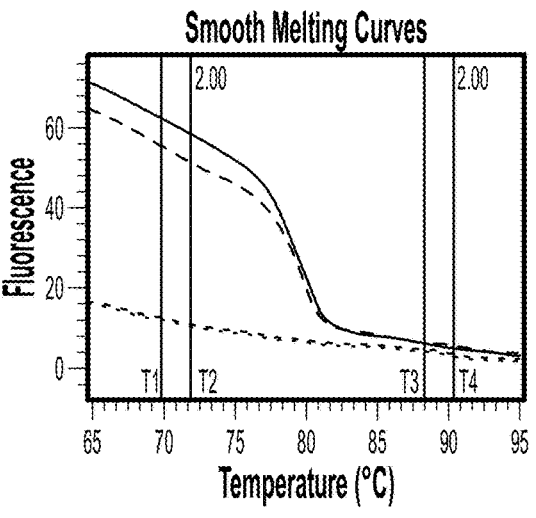
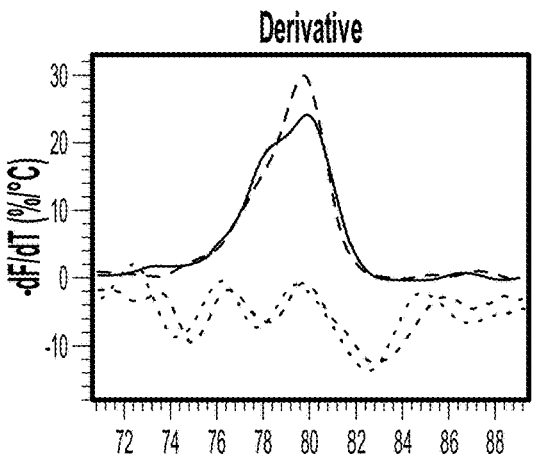
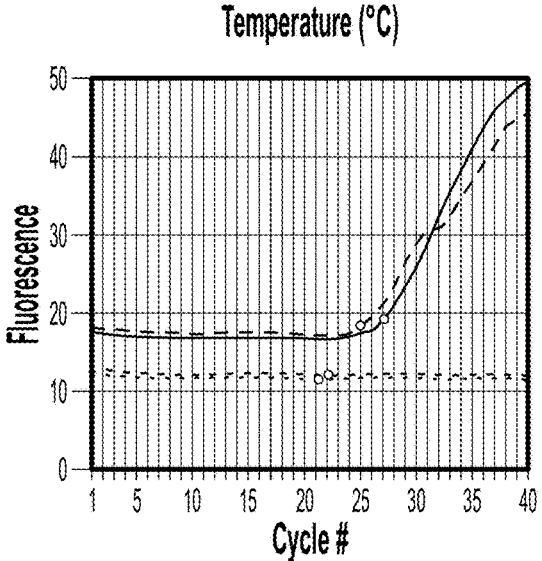
☑ Ch1   ☑ Ch2   ☑ Ch3   ☑ Ch4
☐ Ch5   ☐ Ch6   ☐ Ch7   ☐ Ch8
○ Denature   ○ Arrival   ● Extension
Cq Values
| CH1 | CH2 | CH3 | CH4 | CH5 | CH6 | CH7 | CH8 |
|-----|-----|-----|-----|-----|-----|-----|-----|
| 27.06 | 21.10 | 22.07 | 24.87 | 23.05 | 22.03 | 34.00 | 40.00 |
3 min PCR
FIG. 33A-C

*MTHFR1286*
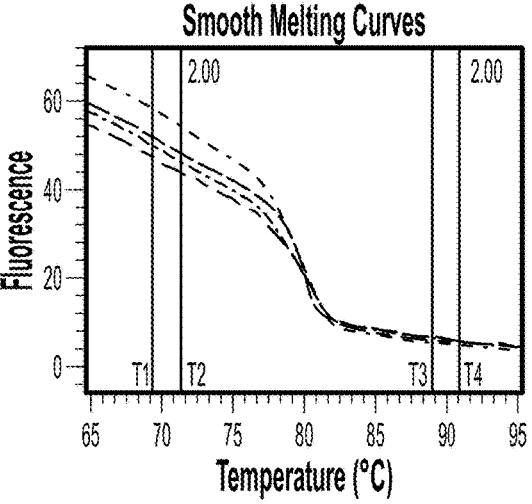
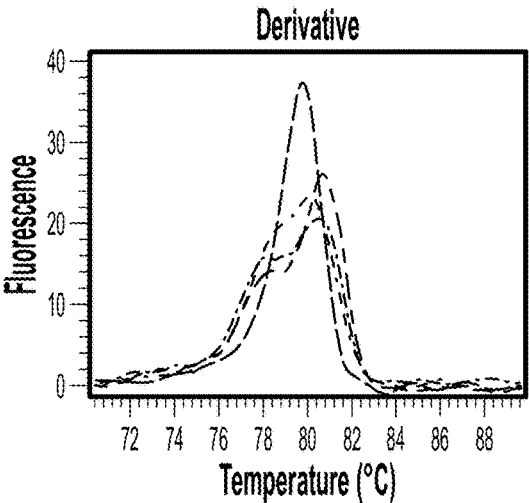
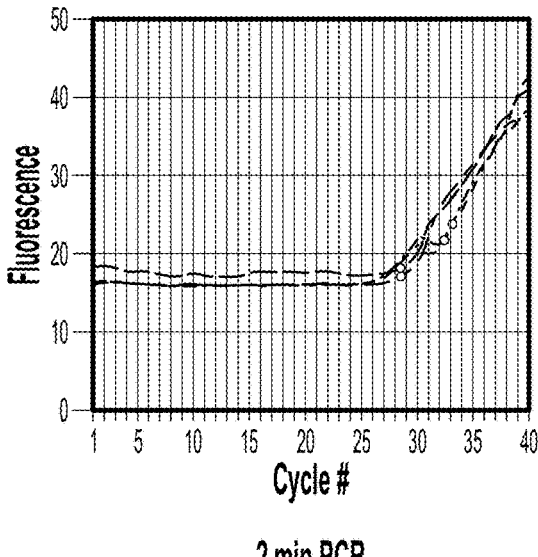
2 min PCR
FIG. 33D-F

*MTHFR665*
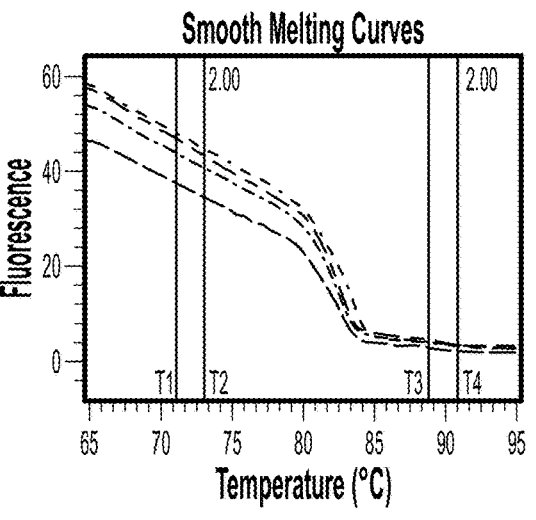
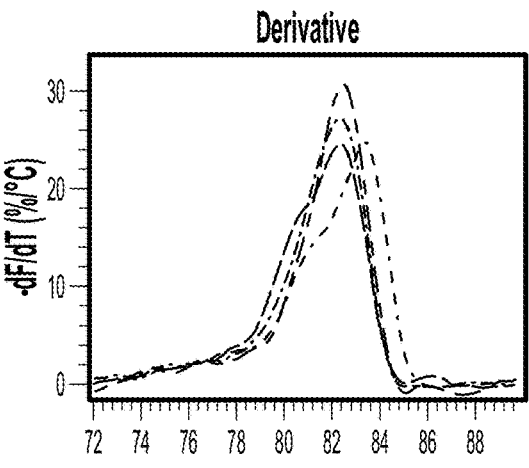
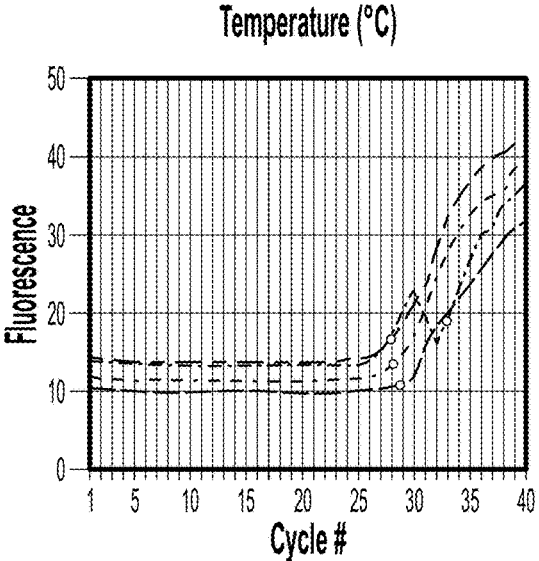
| CH1 | CH2 | CH3 | CH4 | CH5 | CH6 | CH7 | CH8 |
|-----|-----|-----|-----|-----|-----|-----|-----|
| 27.23 | 40.00 | 33.71 | 33.44 | 28.72 | 33.03 | 27.97 | 28.14 |
3 min PCR
FIG. 33G-I

MTHFR665
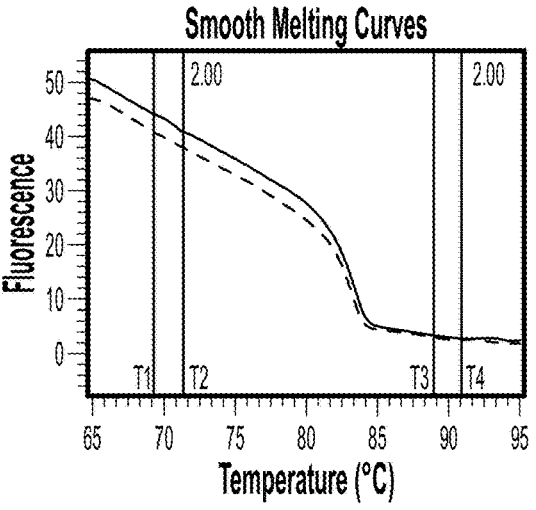
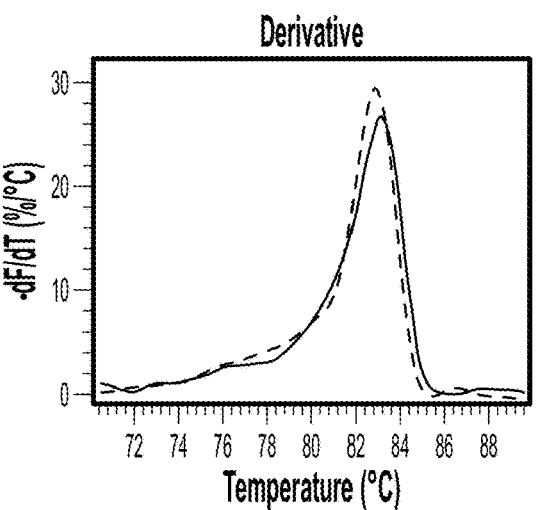
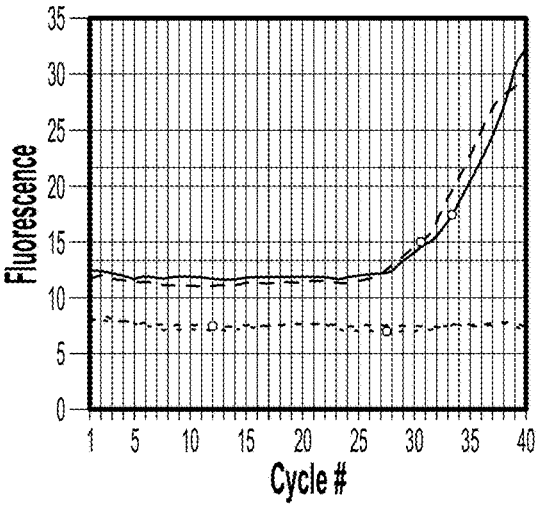
☑ Ch1  ☑ Ch2  ☑ Ch3  ☑ Ch4
☐ Ch5  ☐ Ch6  ☐ Ch7  ☐ Ch8
○ Denature  ○ Arrival  ● Extension
Cq Values
| CH1 | CH2 | CH3 | CH4 | CH5 | CH6 | CH7 | CH8 |
|-----|-----|-----|-----|-----|-----|-----|-----|
| 33.39 | 27.31 | 11.99 | 30.49 | 28.39 | 32.36 | 28.48 | 32.99 |
2 min PCR
FIG. 33J-L

*MTHFR1286*
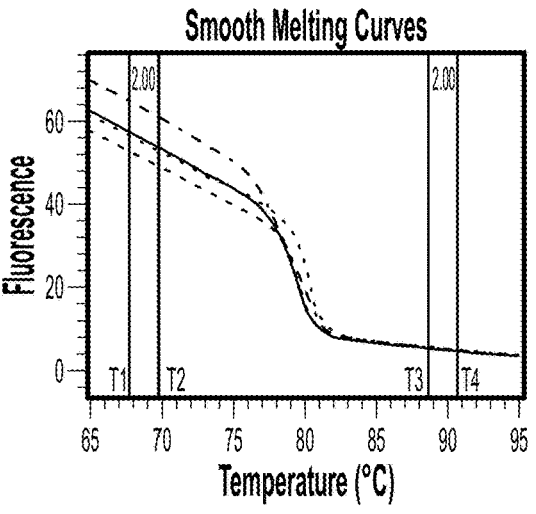
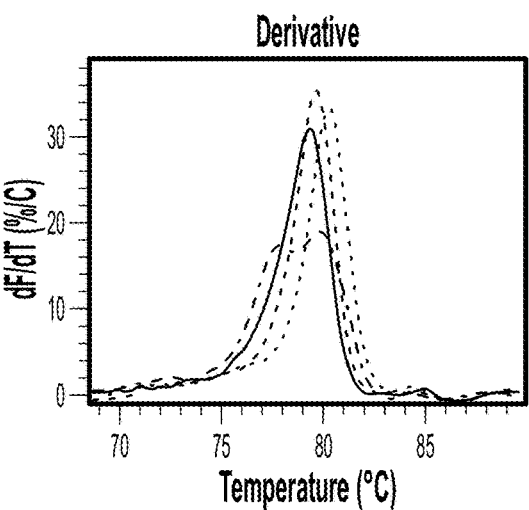
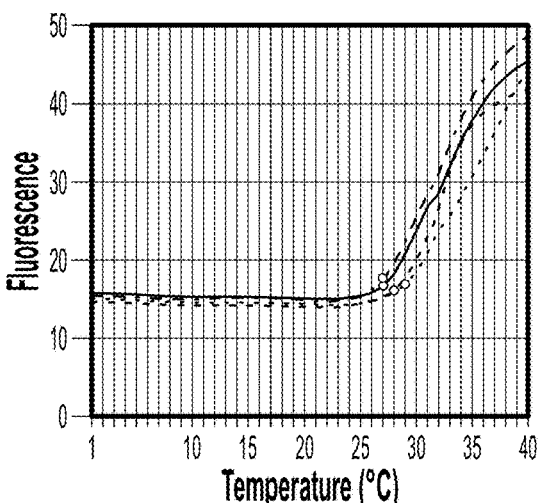
| CH1 | CH2 | CH3 | CH4 | CH5 | CH6 | CH7 | CH8 |
|-------|-------|-------|-------|-------|-------|-------|-------|
| 25.08 | 26.10 | 25.96 | 27.37 | 22.11 | 29.12 | 20.44 | 21.41 |
3 min PCR
FIG. 34A-C

*MTHFR1286*
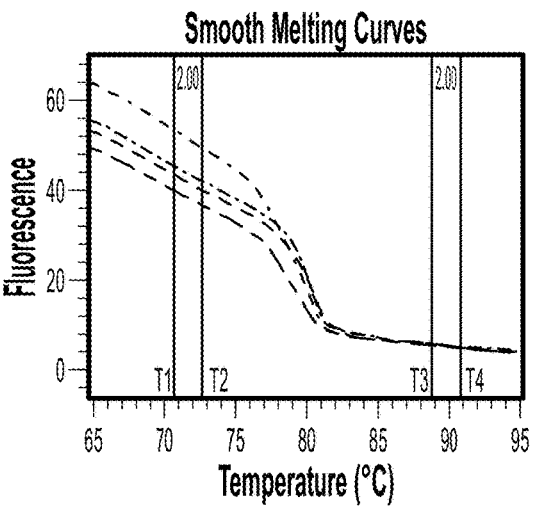
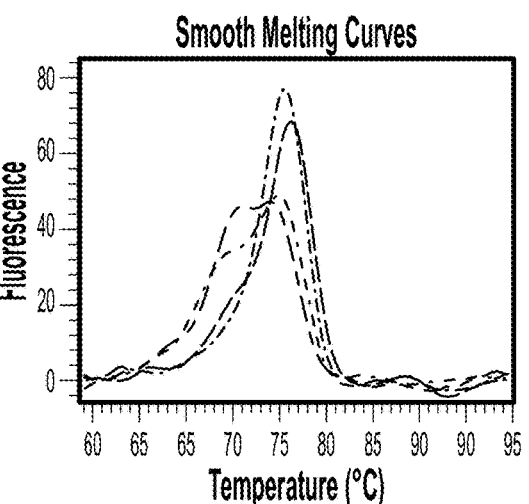
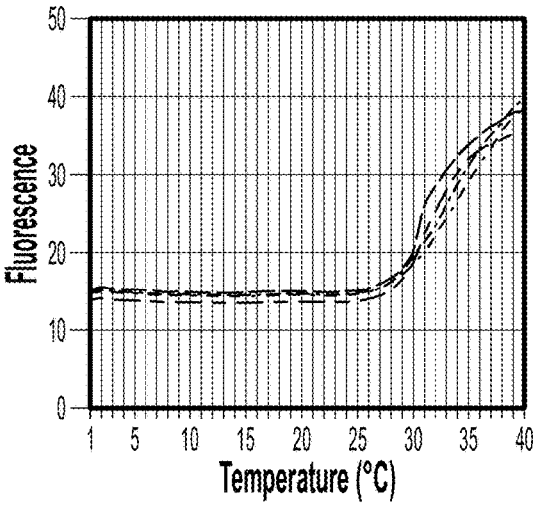
| | Ch1 | | Ch2 | | Ch3 | | Ch4 |
| | Ch5 ☑ | | Ch6 ☑ | | Ch7 ☑ | | Ch8 ☑ |
○ Denature  ○ Arrival  ● Extension
Cq Values
| CH1 | CH2 | CH3 | CH4 | CH5 | CH6 | CH7 | CH8 |
|-----|-----|-----|-----|-----|-----|-----|-----|
| 33.50 | 35.60 | 11.63 | 10.05 | 26.37 | 26.63 | 25.72 | 26.38 |
2 min PCR
FIG. 34D-F

*MTHFR665*
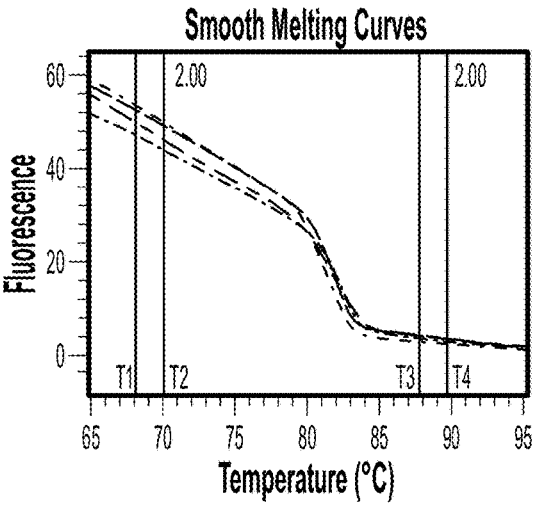
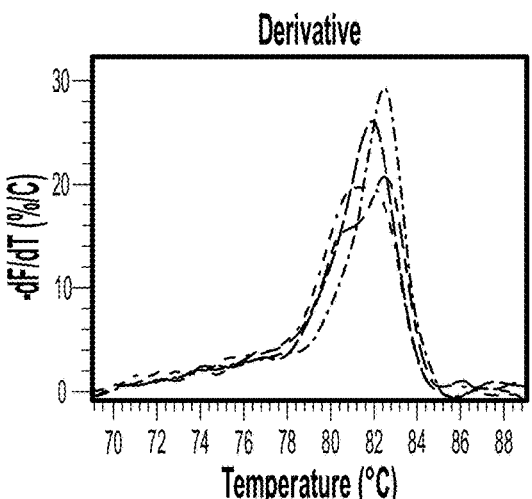
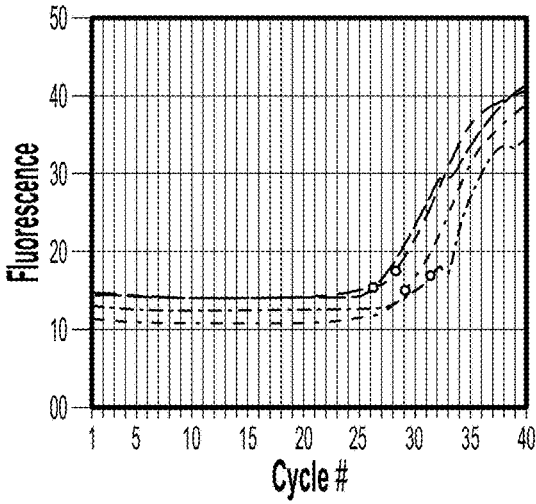
| Cq Values | | | | | | | |
|---|---|---|---|---|---|---|---|
| CH1 | CH2 | CH3 | CH4 | CH5 | CH6 | CH7 | CH8 |
| 22.7 | 40.00 | 39.00 | 17.62 | 26.19 | 31.27 | 28.10 | 28.81 |
3 min PCR
FIG. 34G-I

*MTHFR665*
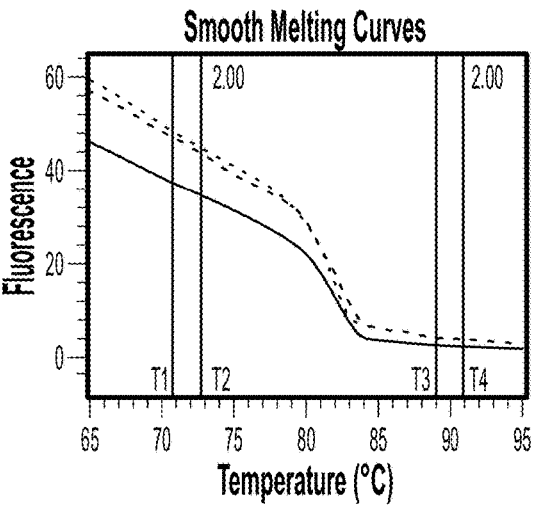
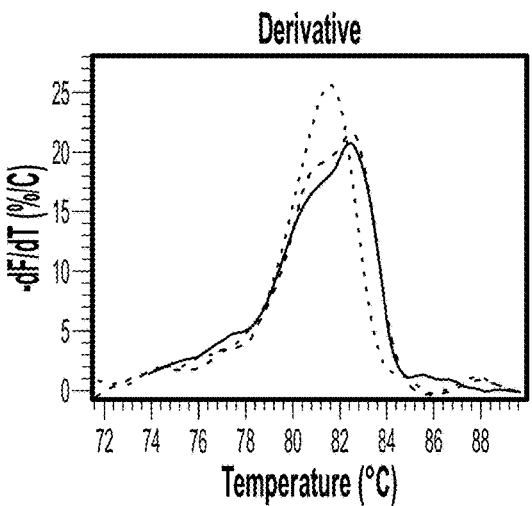
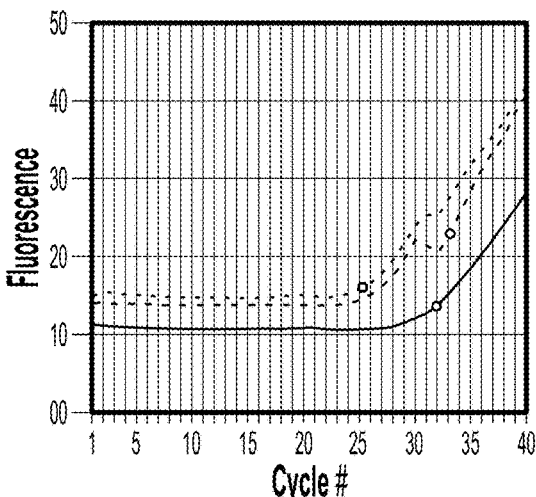
| CH1 | CH2 | CH3 | CH4 | CH5 | CH6 | CH7 | CH8 |
|-----|-----|-----|-----|-----|-----|-----|-----|
| 31.78 | 25.00 | 33.04 | 17.48 | 27.70 | 28.28 | 27.97 | 29.02 |
2 min PCR
FIG. 34J-L

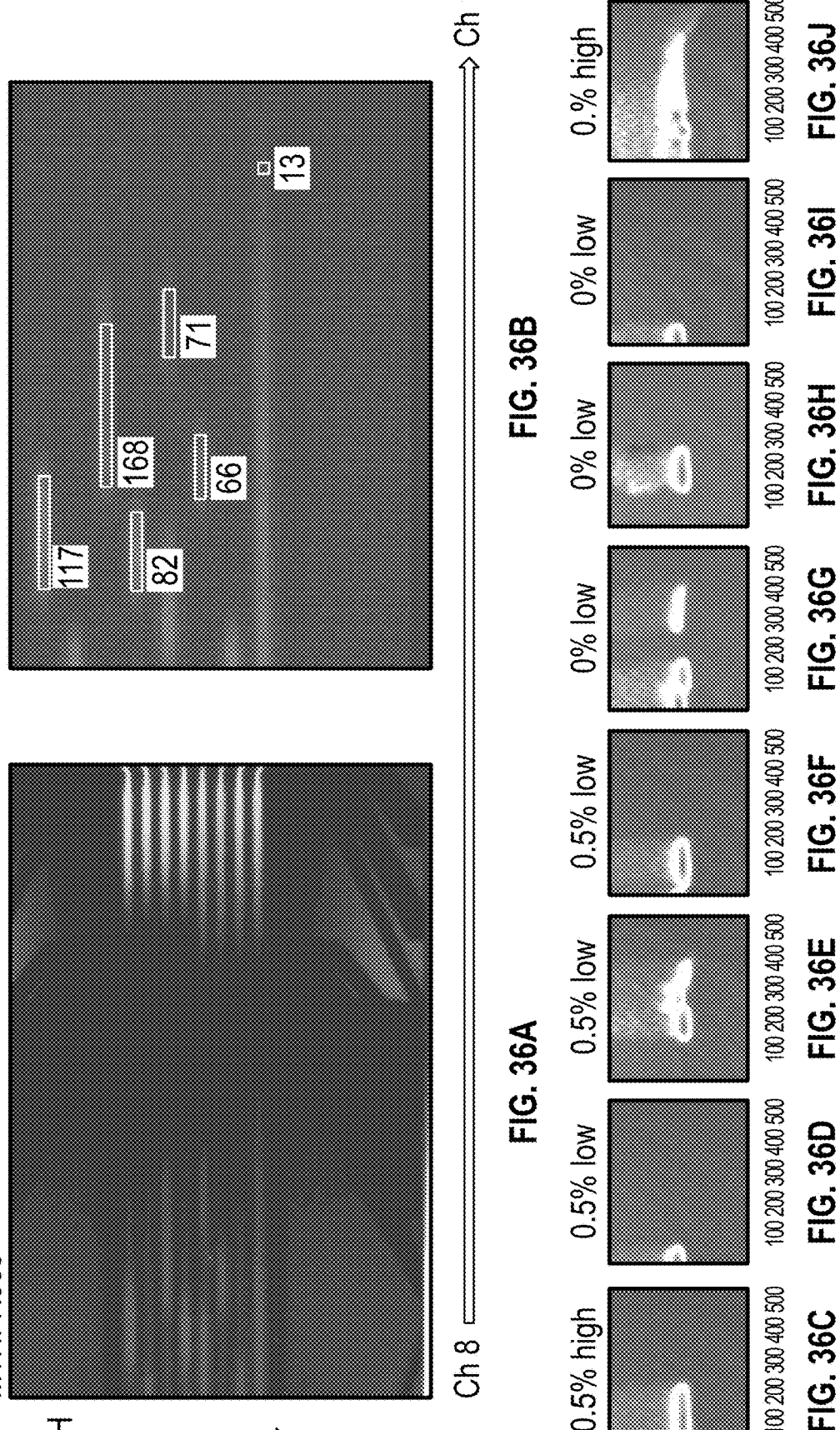

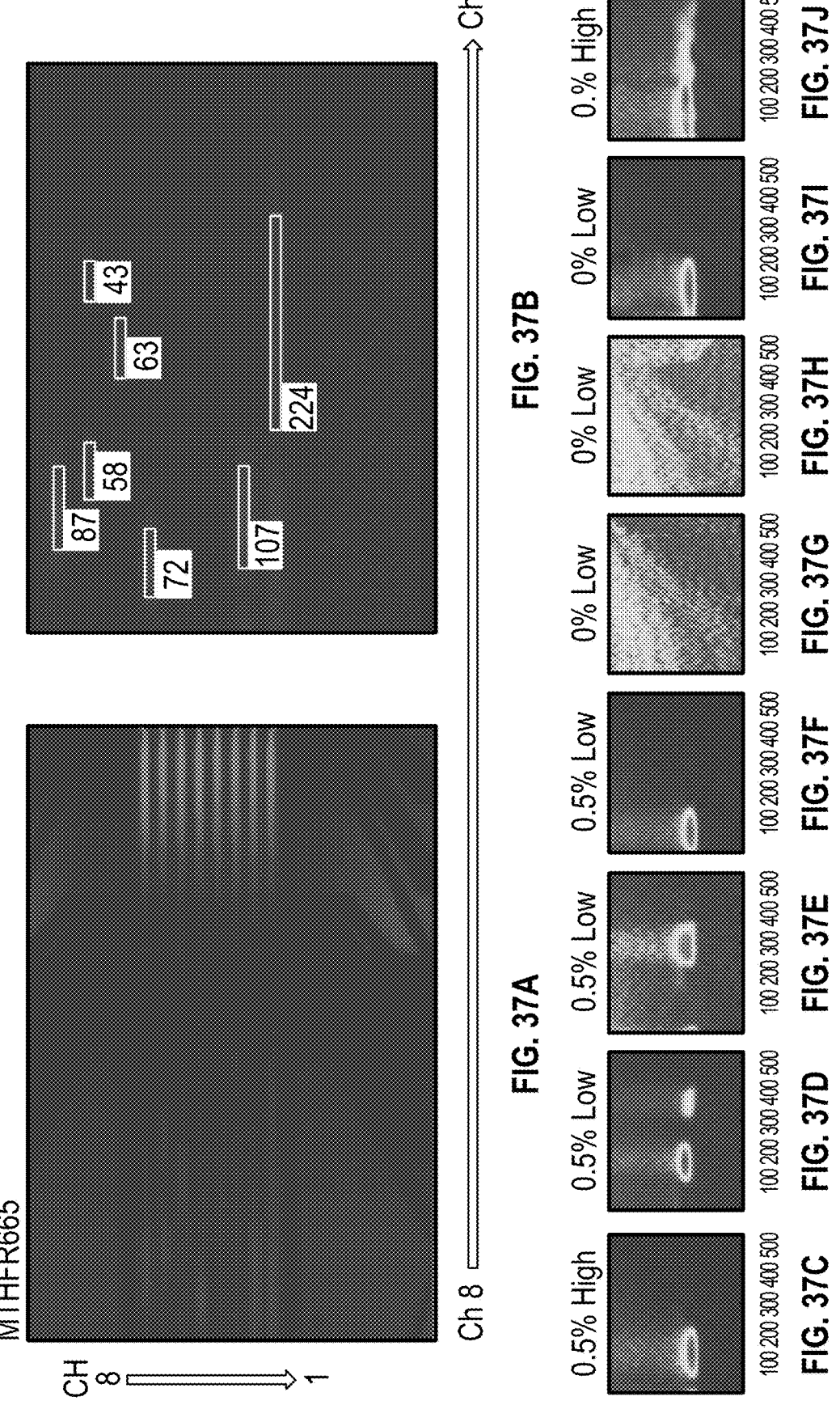

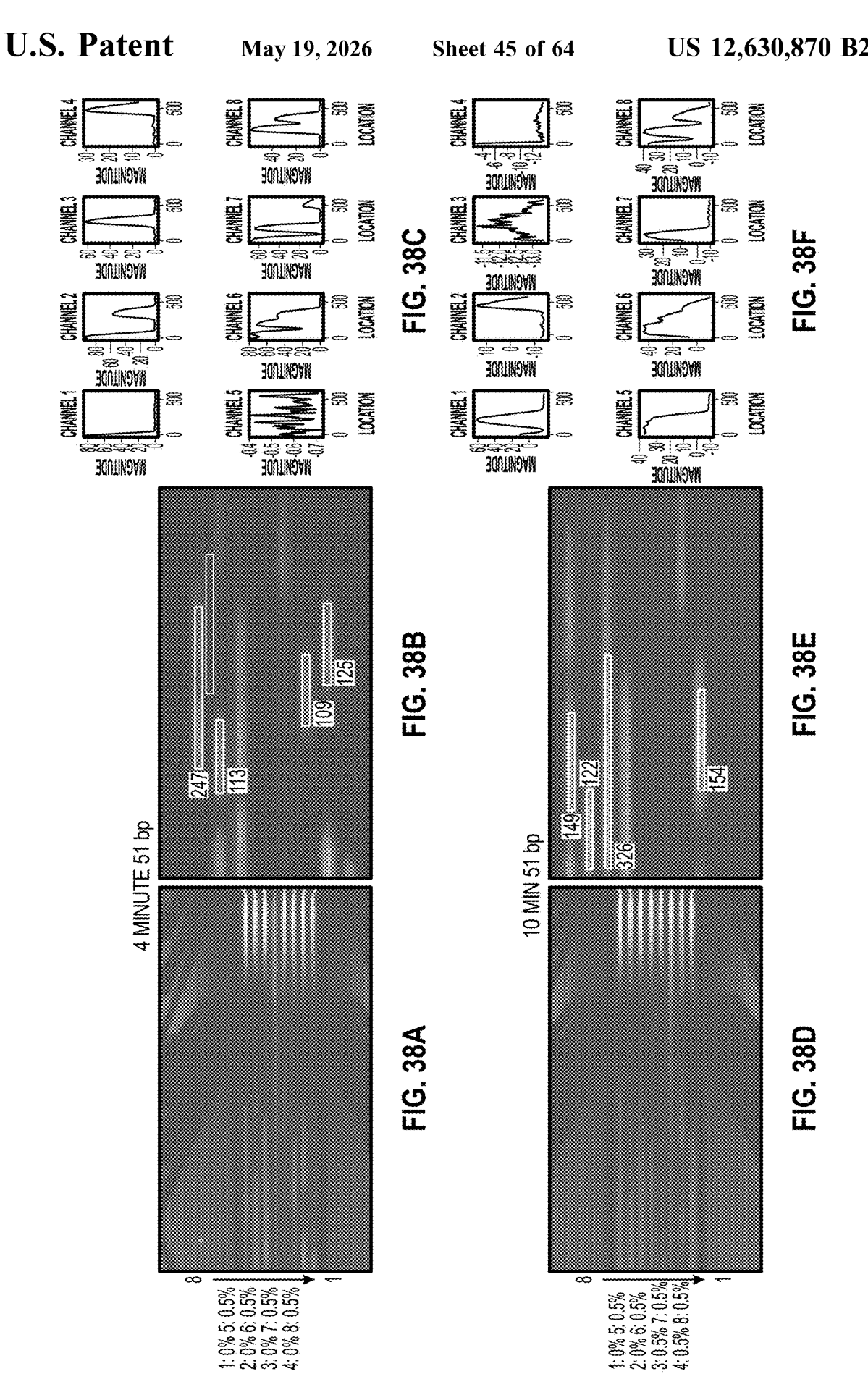

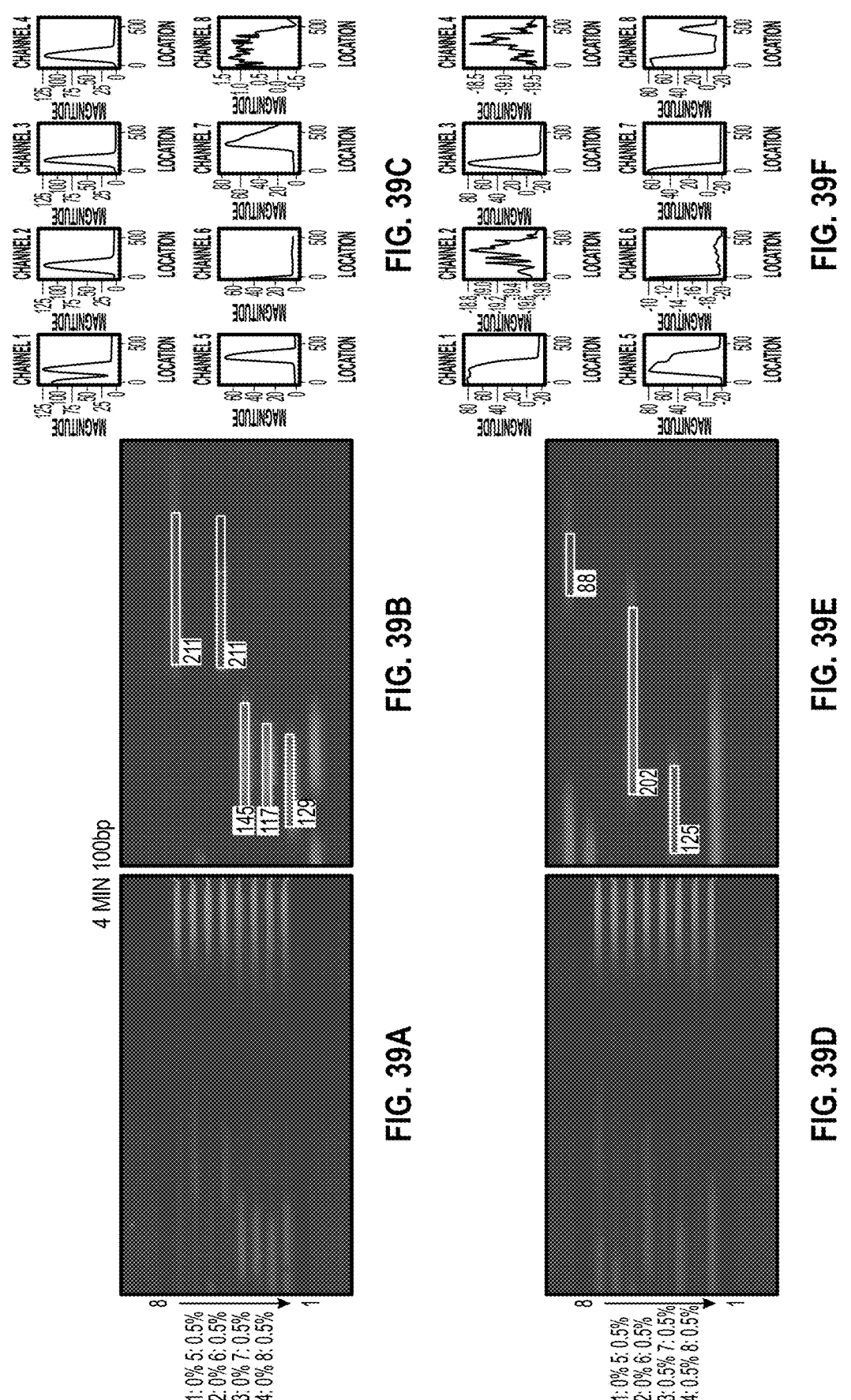

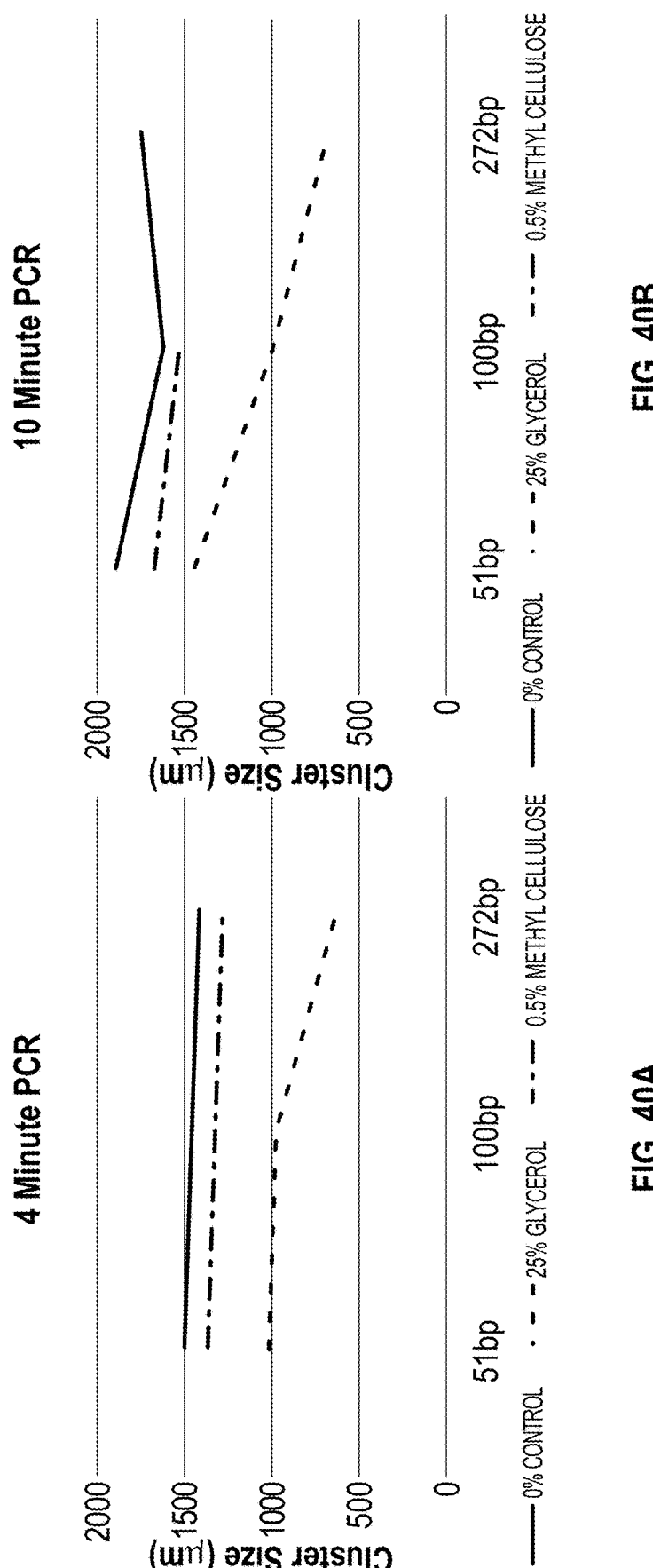

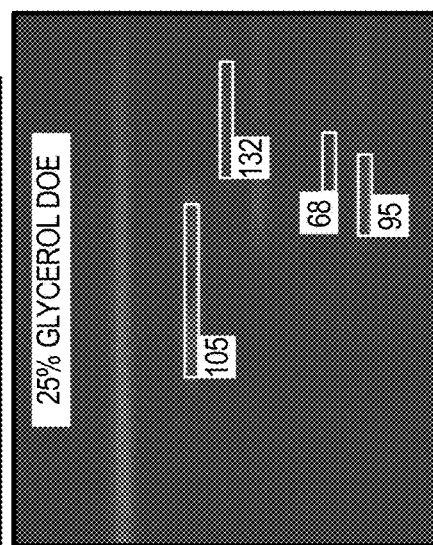
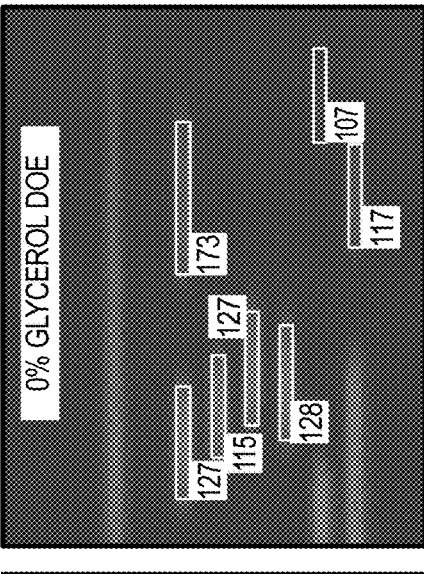
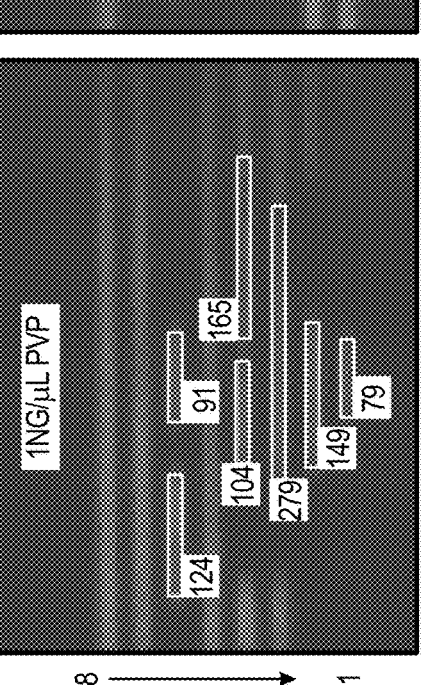
FIG. 41C
FIG. 41B
FIG. 41A
1: LOW  5: LOW
2: LOW  6: LOW
3: LOW  7: PVP HIGH
4: LOW  8: 0 PVP HIGH

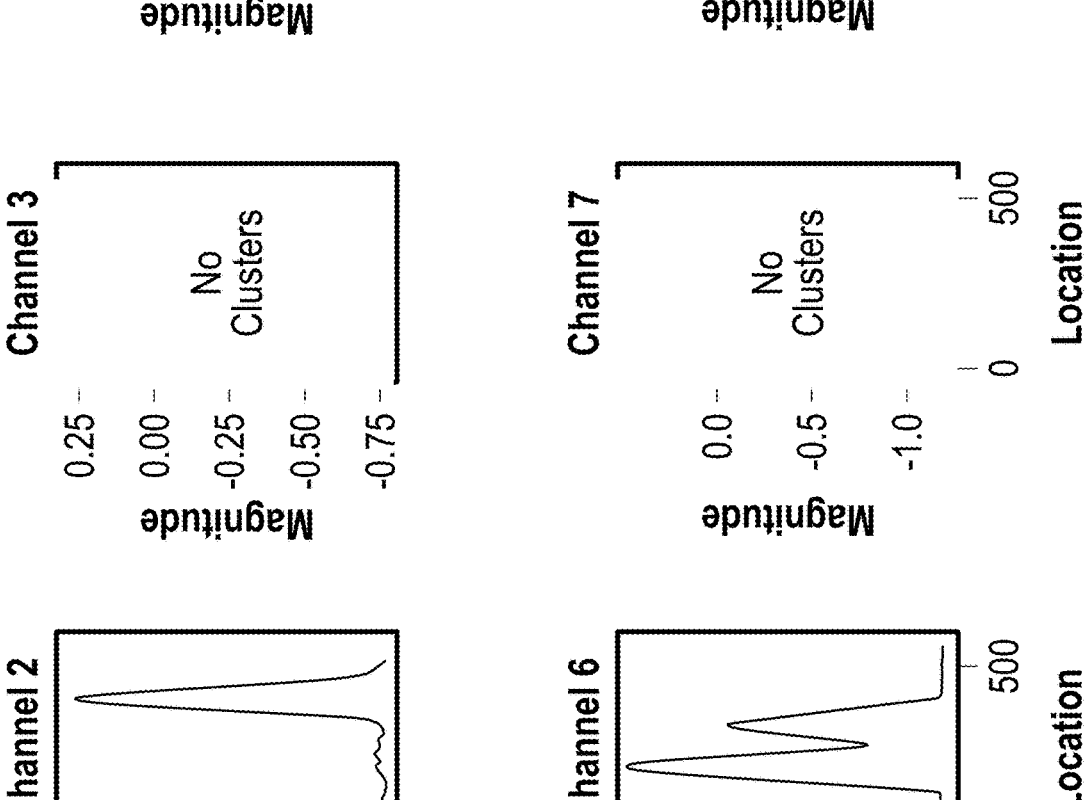
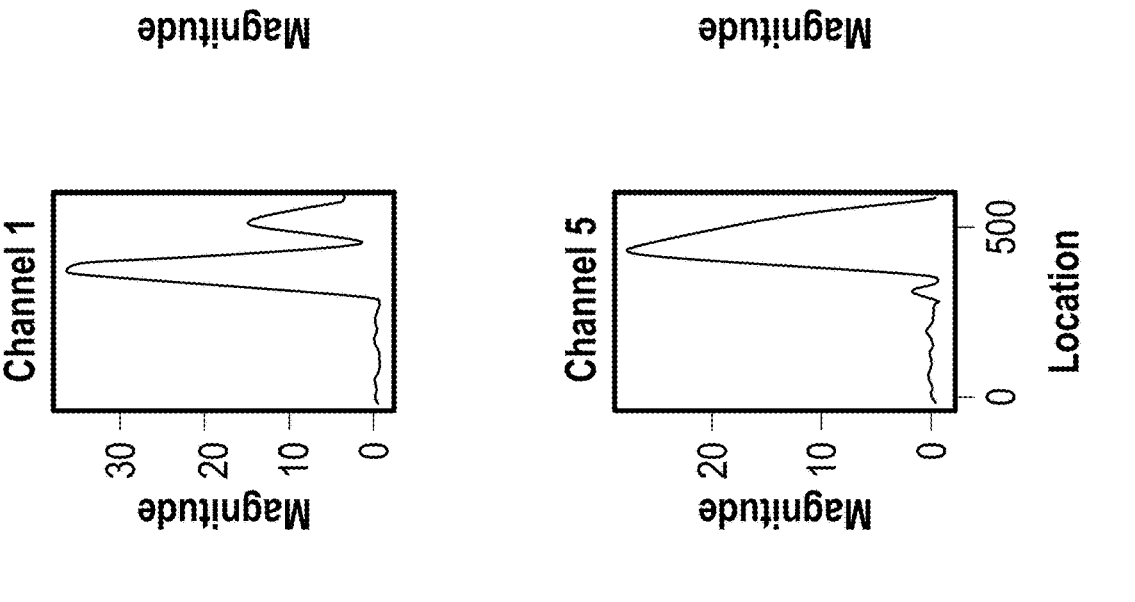
FIG. 41F

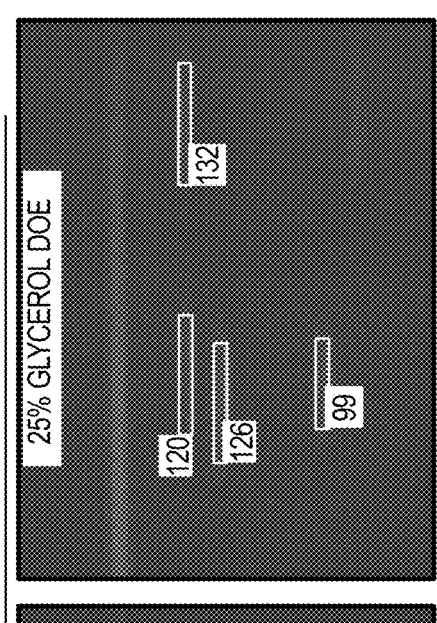
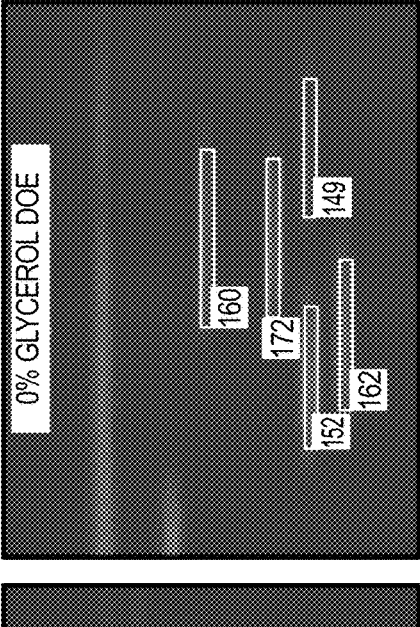
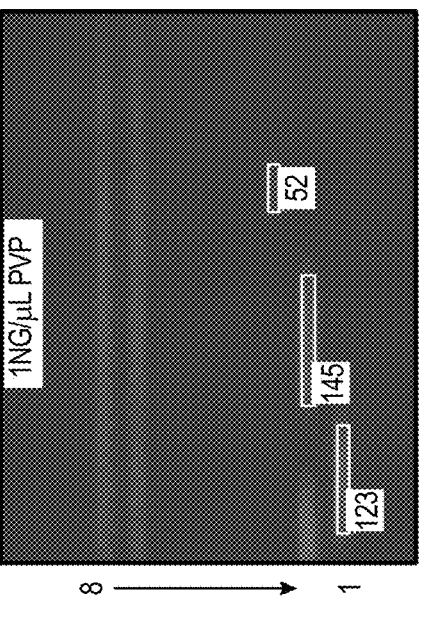
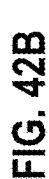
1: LOW   5: LOW
2: LOW   6: LOW
3: LOW   7: PVP HIGH
4: LOW   8: 0 PVP HIGH
25% GLYCEROL DOE
FIG. 42C
0% GLYCEROL DOE
FIG. 42B
PVP 51 BP 10 MIN
1NG/µL PVP
FIG. 42A

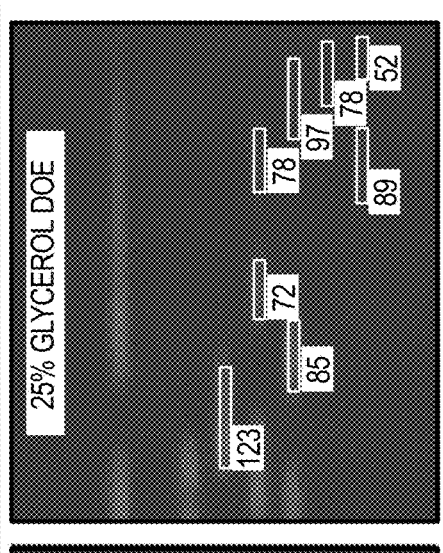
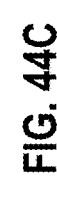
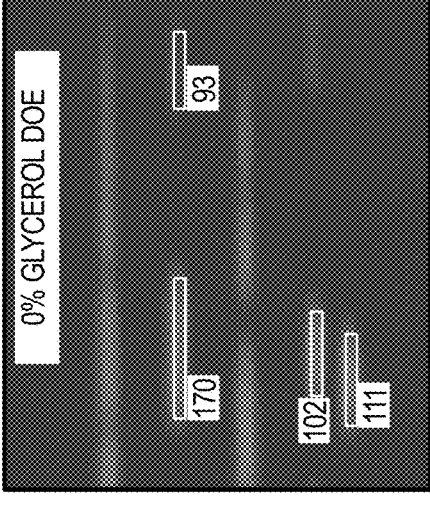
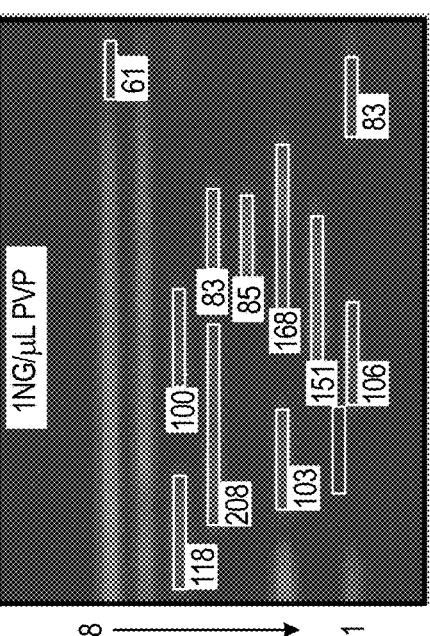
FIG. 44A
FIG. 44B
FIG. 44C

FIG. 44F

PARTITION-FREE DIGITAL PCR (dPCR) SYSTEM

PRIORITY AND INCORPORATION BY REFERENCE

The present application claims priority to U.S. Provisional Patent Application Ser. No. 62/795,392 filed Jan. 22, 2019 and to U.S. Provisional Patent Application Ser. No. 62/947, 393 filed Dec. 12, 2019, the disclosures of which are incorporated herein by reference in their entireties.

BACKGROUND

Field of the Disclosure

The present disclosure relates to implementation of partition-free digital polymerase chain reaction (dPCR). Digital PCR requires that a sample must first be partitioned into individual reactions before amplification can occur. The present disclosure provides methods of partitioning a sample without the use of physical partitions or barriers and methods of performing partition-free digital PCR.

Description of the Related Art

Digital polymerase chain reaction (dPCR) is a method that measures the amount of DNA or RNA in a sample without the need for a calibration curve or reference standards. To perform dPCR, a single PCR reaction mix is partitioned into individual reactions before amplification occurs, so that positive reactions can be counted after the PCR amplification to estimate a number of copies contained in the initial reaction mix. This often takes the form of a digital signal based on whether the target is present or not, resulting in a read off as a "1" or "0" (positive or negative). Absolute quantification can be calculated using Poisson statistics based on the ratio of positive and negative responses. Due to the sensitivity and easy reproducibility, dPCR is becoming popular in both the clinical and scientific communities. For example, dPCR is useful in oncology applications, where rare and limited DNA is often hard to detect. In comparison, traditional qPCR methods utilize an analog signal from a real-time fluorescence vs temperature curve for less accurate quantification (accuracies only as low as 2-fold differences can be seen) and requires a standard curve to interpret the quantitative results.

Current state-of-the-art dPCR systems use physical partitioning of the PCR reagent and sample mixture to achieve a digital signal by generating thousands of water-in-oil droplets or micro reaction wells in the dPCR consumables that require highly complicated microfluidic circuitry in the consumables and detection systems. The high complexity of such systems also requires many hands-on steps for the users or more complicated automation steps. Moreover, the sophisticated detection systems required by this partition based approach in order to count the positive reactions may include a flow cytometer or a high-resolution imaging system to recognize individual physical partitions in the reaction chamber. Current dPCR systems therefore involve numerous instruments and require a long lead time to run each experiment, making it inefficient and difficult to implement dPCR into clinical settings.

SUMMARY OF THE DISCLOSURE

The present disclosure relates to a method for partition-free quantification of molecules.

Thus, in one aspect, the present disclosure provides a method comprising the steps of introducing a sample into a chamber, wherein the sample comprises one or more nucleic acids, and wherein the nucleic acids are distributed across the chamber; providing a thermal system in thermal communication with the sample; providing an optical detection system in communication with the one or more nucleic acid samples, wherein the optical detection system comprises an imaging system; performing amplification of the one or more nucleic acids; obtaining one or more images of the amplified nucleic acids; and digitally quantifying the amplified nucleic acids based on fluorescence distribution across the chamber.

In a second aspect, the present disclosure relates to a system for quantification of molecules comprising a thermal cycler; a cartridge detachably coupled to the thermal cycler, having a region for receiving a nucleic acid sample wherein the region is free of partitions; a detector for detecting fluorescence; and a controller for performing a digital PCR process of the nucleic acid sample received in the region.

These and other embodiments, objects, features, and advantages of the present disclosure will become apparent upon reading the following detailed description of exemplary embodiments of the present disclosure, when taken in conjunction with the appended drawings, and provided claims.

BRIEF DESCRIPTION OF THE FIGURES

FIG. 7 is a flow chart of the image processing process and images depicting the conversion from RGB to fluorescence.

FIG. 10 is a flow chart of the image processing process and images depicting the reduction of each channel's data to a single row.

FIG. 13 is an illustration depicting data that can be obtained by simulations described in the examples, or through analysis of images showing the FWHM cluster boundaries across the length of a channel.

FIG. 14 is a chart showing cluster size and dynamic range as calculated via a monte carlo simulation.

FIG. 15 is a diagram illustrating the simulation conditions.

FIG. 16 is a diagram illustrating the micro-channel of a rectangular cross-section of 180 μm in width and 20 μm in depth used in the simulation.

FIG. 17 details the Stokes-Einstein equation as used in the simulation.

FIG. 20A-D are charts showing the BioRad results for PVP.

FIG. 25A-D are charts showing the maximum additive concentration compared to no template control.

Figures 29A, 29B, 29C, 29D, 29E, 29F:
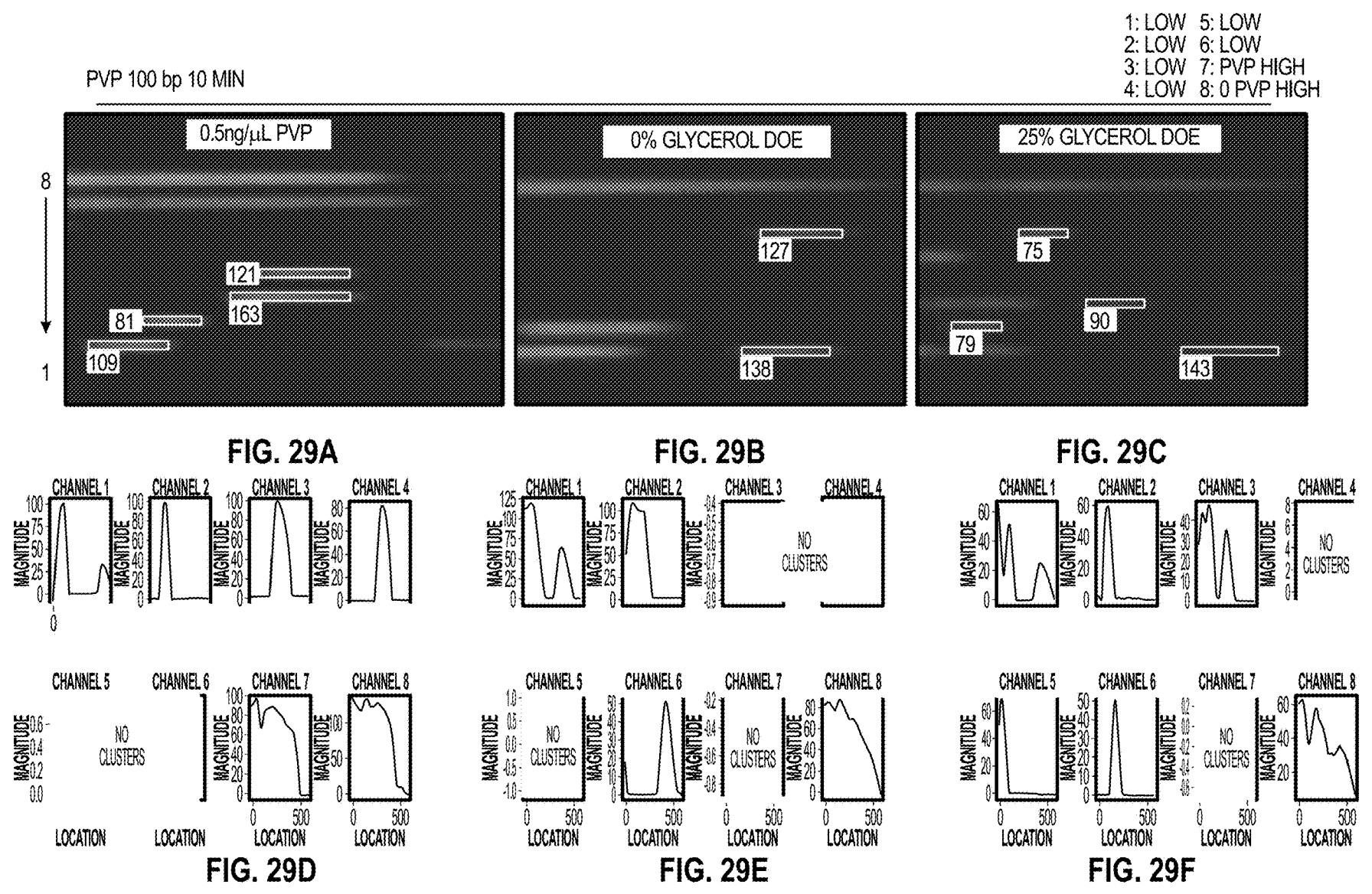

FIG. 29A-C are analyzed images of 8-channel cartridges, and FIG. 29D-F are charts for each channel of the cartridges showing DOE results with PVP for 100 bp assay at 10 minutes.

FIG. 32A-C are charts showing 3 minute PCR results for MTHFR1286 with methyl cellulose.

FIG. 32D-F are charts showing 2 minute PCR results for MTHFR1286 with methyl cellulose. FIG. 32G-I are charts showing 3 minute PCR results for MTHFR665 with methyl cellulose. FIG. 32J-L are charts showing 2 minute PCR results for MTHFR665 with methyl cellulose.

FIG. 33A-C are charts showing 3 minute PCR results for MTHFR1286 with PVP. FIG. 33D-F are charts showing 2 minute PCR results for MTHFR1286 with PVP. FIG. 33G-I are charts showing 3 minute PCR results for MTHFR665 with PVP. FIG. 33J-L are charts showing 2 minute PCR results for MTHFR665 with PVP.

FIG. 34A-C are charts showing 3 minute PCR results for MTHFR1286 with Ficoll. FIG. 34D-F are charts showing 2 minute PCR results for MTHFR1286 with Ficoll. FIG. 34G-I are charts showing 3 minute PCR results for MTHFR665 with Ficoll. FIG. 34J-L are charts showing 2 minute PCR results for MTHFR665 with Ficoll.

FIG. 36A-B are images of a cartridge undergoing HRM on samples having Low DNA Concentration of MTHFR1286 with methyl cellulose. FIG. 36C-J are images from the HRM analysis software of clusters from each channel of the cartridges in 36A-B, with channel 8 in FIG. 36C and channel 1 in FIG. 36J.

FIG. 37A-B are images of a cartridge undergoing HRM on samples having Low DNA Concentration for of MTHFR665 with methyl cellulose. FIG. 37C-J are images from the HRM analysis software of clusters from each channel of the cartridges in 37A-B, with channel 8 in FIG. 37C and channel 1 in FIG. 37J.

FIG. 38A-C are images (FIG. 38A-B) of a cartridge and charts (FIG. 38C) showing HRM analysis following 4 minute PCR of 51 bp CSP1 for methyl cellulose DOE. FIG. 38D-F are images (FIG. 38D-E) of a cartridge and charts (FIG. 38F) showing HRM analysis following 10 minute PCR of 51 bp CPS1 for methyl cellulose DOE.

FIG. 39A-C are images (FIG. 39A-B) of a cartridge and charts (FIG. 39C) showing HRM analysis following 4 minute PCR of 100 bp CSP1 for methyl cellulose DOE. FIG. 39D-F are images (FIG. 39D-E) of a cartridge and charts (FIG. 39F) showing HRM analysis following 10 minute PCR of 100 bp CPS1 for methyl cellulose DOE.

FIG. 40A-B are charts showing the cluster size vs PCTR time and additive for methyl cellulose vs. glycerol.

FIG. 41A-C are analyzed images of 8-channel cartridges and FIG. 41D-F are charts showing DOE results with PVP for 51 bp assay at 4 minutes.

Figure 42E:
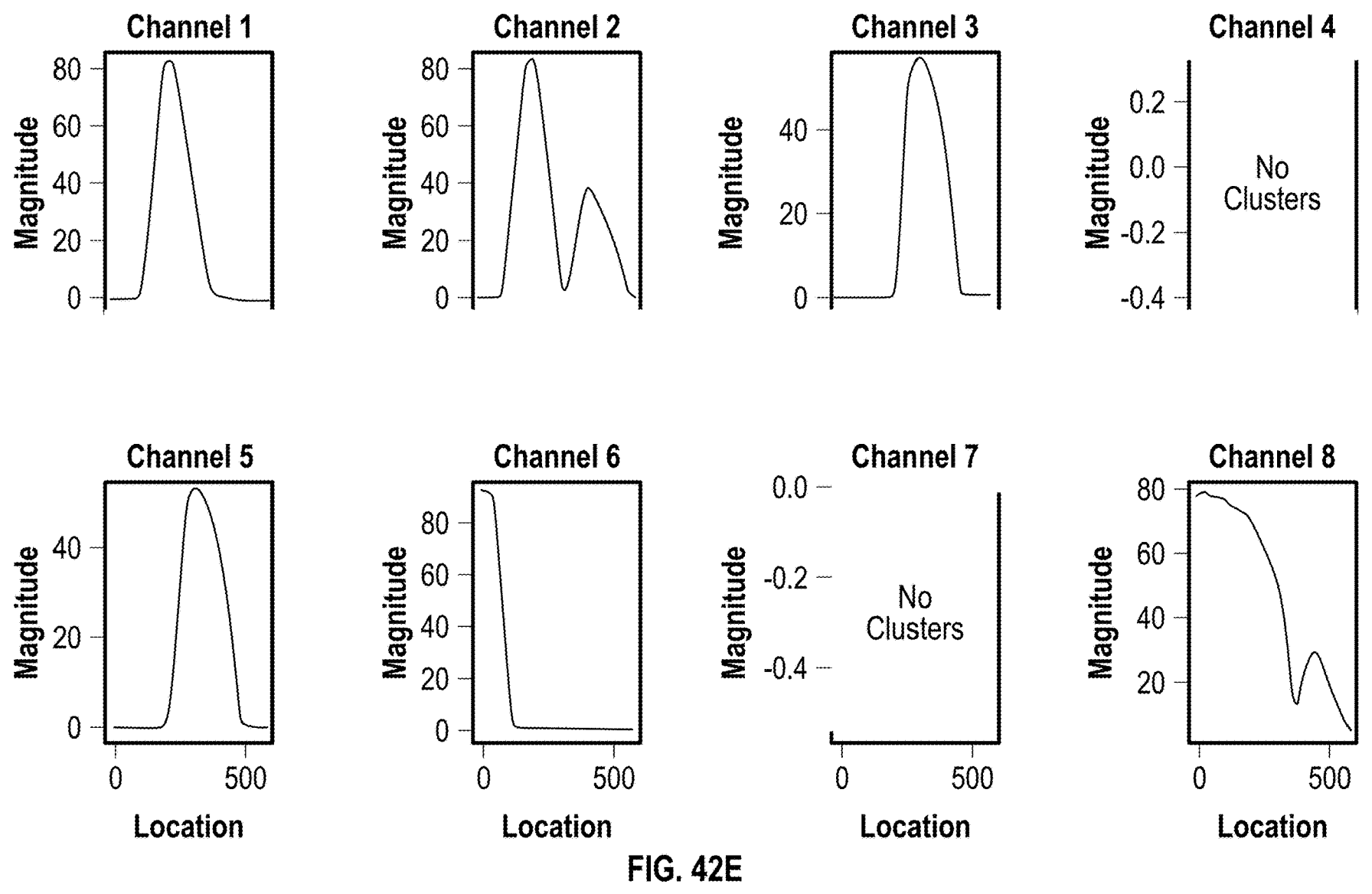
Figure 42F:
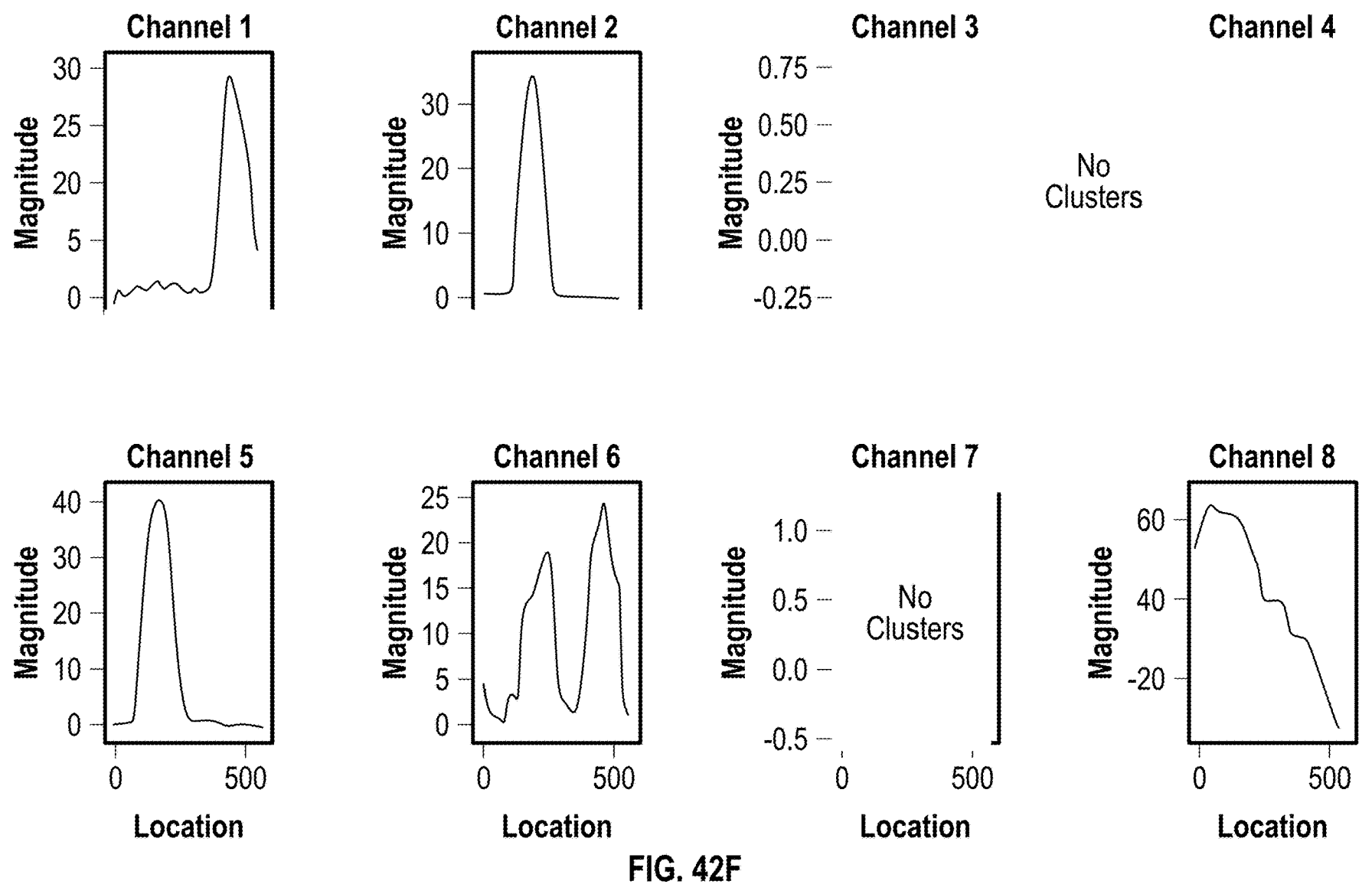

FIG. 42A-C are analyzed images of 8-channel cartridges and FIG. 42D-F are charts showing DOE results with PVP for 51 bp assay at 10 minutes.

Figure 43F:
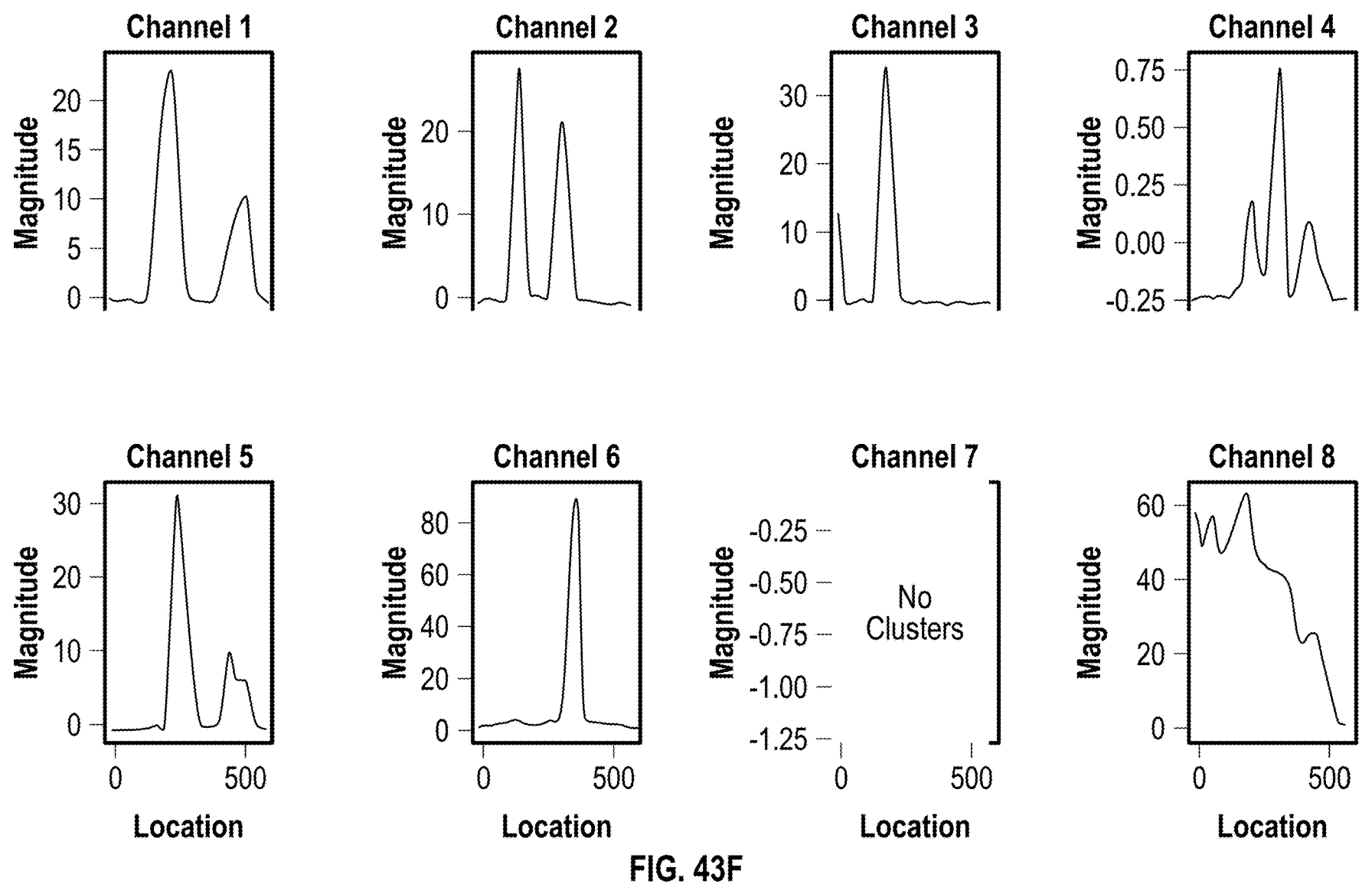

FIG. 43A-C are analyzed images of 8-channel cartridges and FIG. 43D-F are charts showing DOE results with PVP for 272 bp assay at 4 minutes.

Figure 44F:
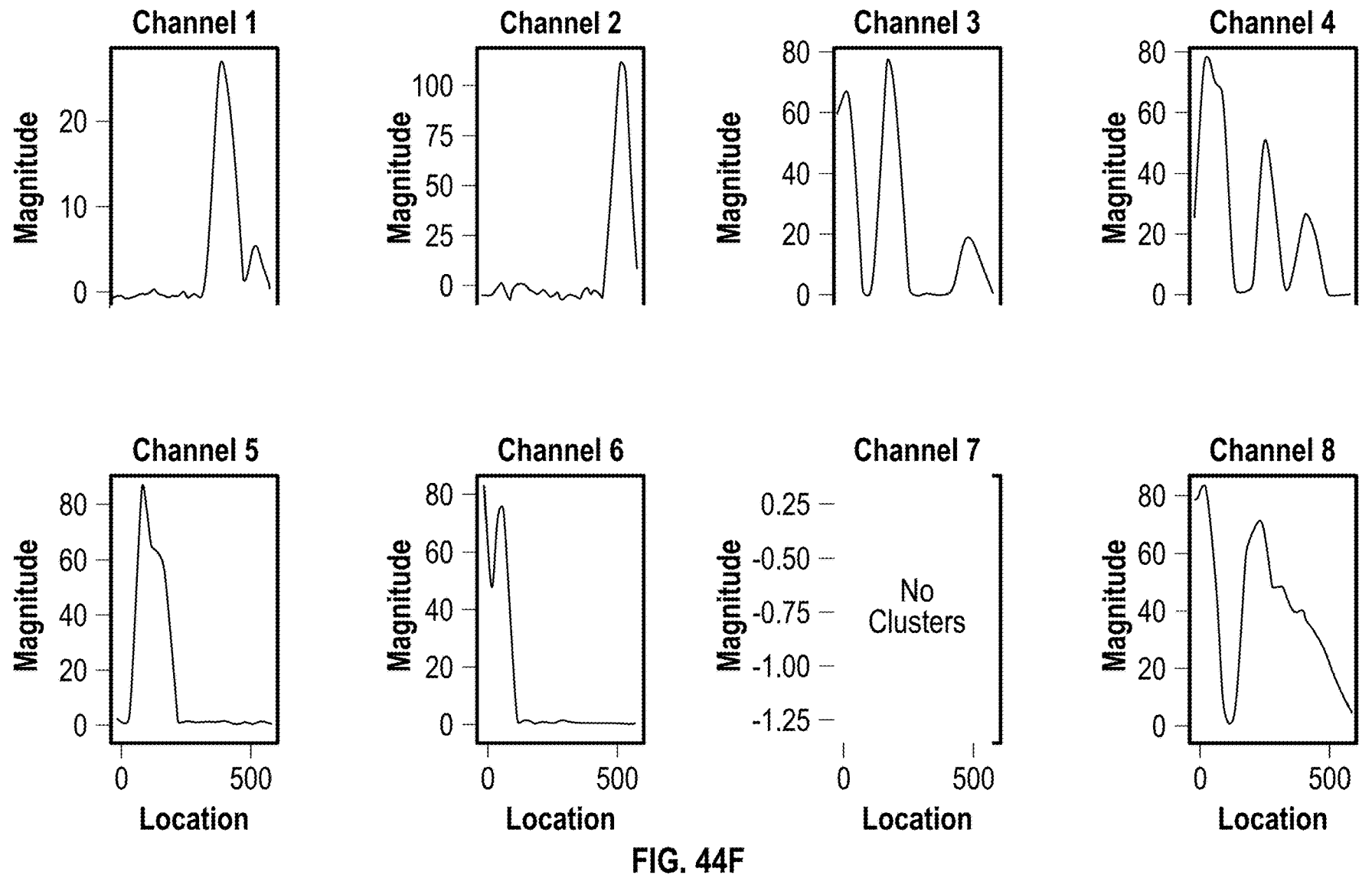

FIG. 44A-C are analyzed images of 8-channel cartridges and FIG. 44D-F are charts showing DOE results with PVP for 100 bp assay at 4 minutes.

Figures 1A, 1B:
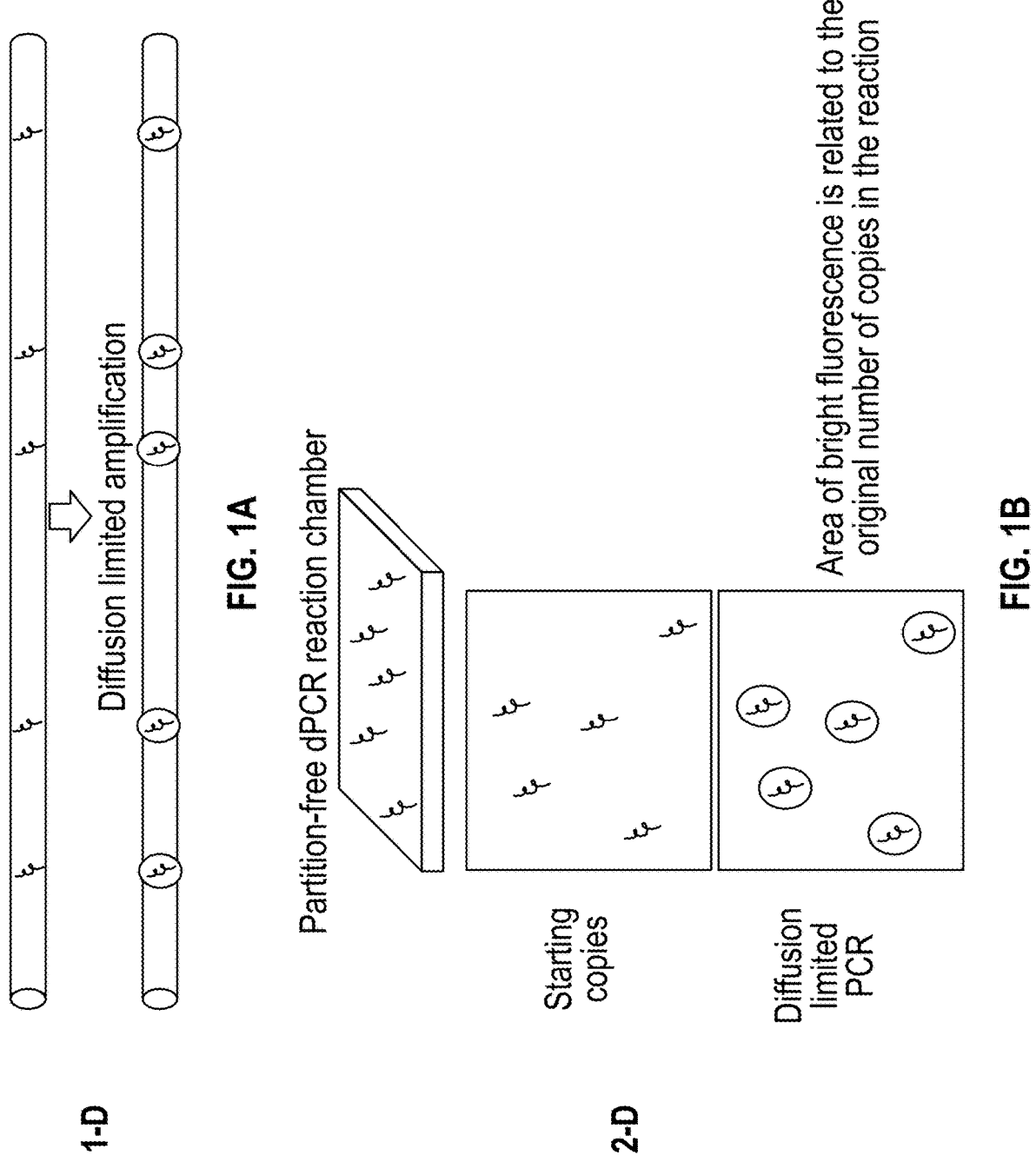
FIG. 1A-B are illustrated examples of partition-free digital analysis after diffusion limited PCR amplification.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative exemplary embodiments. It is intended that changes and modifications can be made to the described exemplary embodiments without departing from the true scope and spirit of the subject disclosure as defined by the appended claims.

DETAILED DESCRIPTION OF EXEMPLARY EMBODIMENTS

The present disclosure has several embodiments and relies on patents, patent applications and other references for details known to those of the art. Therefore, when a patent, patent application, or other reference is cited or repeated herein, it should be understood that it is incorporated by reference in its entirety for all purposes as well as for the proposition that is recited.

In referring to the description, specific details are set forth in order to provide a thorough understanding of the examples disclosed. In other instances, well-known methods, procedures, components and circuits have not been described in detail as not to unnecessarily lengthen the present disclosure.

The practice of the present disclosure may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Stryer, L. (1995) Biochemistry (4th Ed.) Freeman, N.Y., Gait, Oligonucleotide Synthesis: A Practical Approach, 1984, IRL Press, London, Nelson and Cox (2000), Lehninger, Principles of Biochemistry 3rd Ed., W. H. Freeman Pub., New York, N.Y. and Berg et al. (2002) Biochemistry, 5th Ed., W. H. Freeman Pub., New York, N.Y., all of which are herein incorporated in their entirety by reference for all purposes.

As used herein, "genetic material" means any nucleic acid, including DNA and RNA. Thus, genetic material may include a gene, a part of a gene, a group of genes, a fragment of many genes, a molecule of DNA or RNA, molecules of DNA or RNA, a fragment of a DNA or RNA molecule, or fragments of many DNA or RNA molecules. Genetic material can refer to anything from a small fragment of DNA or RNA to the entire genome of an organism.

Digital Quantification

The most common form of digital quantification of molecules is digital polymerase chain reaction (dPCR). dPCR is a modification of a standard polymerase chain reaction that allows the user to quantify the amount of amplified nucleic acid strands that exist following amplification of a sample. Traditional dPCR relies on physical separation of starting material such that small quantities of the nucleic acids are present in each partition prior to amplification. Such physical separation can be accomplished by physical barriers or partitions, for instance a well plate or a microfluidic chip or cartridge having multiple reaction sites. Alternatively, the physical separation can be accomplished by utilizing droplet methods, whereby a small amount of the sample to be amplified is encapsulated within a droplet and held separate from the remainder of the sample, for instance, using water in oil droplets.

Other Amplification Methods

Although digital quantification is most often associated with PCR, numerous other reactions and amplification methods can be used with digital quantification, and therefore with the partition-free method provided in the present disclosure.

The sample may be amplified by amplification techniques known in the art, and specifically by nucleic acid amplification reactions. In addition to PCR, nucleic acid amplification reactions may include ligase chain reaction (LCR), strand displacement amplification (SDA), isothermal amplification and loop-mediated isothermal amplification, among others. Such amplification reactions amplify the quantity of the genetic material present within a given sample to a quantity suitable for detection. Monitoring and/or detection of the results of the amplification reaction can occur simultaneous to the amplification reaction occurring, as is common in both dPCR and real-time PCR, both of which may be used to monitor and/or detect the amplification reaction as it progresses in real time.

The genetic material-containing sample can be mixed with reaction components typical and/or necessary for completion of the desired reaction or amplification. Such reaction components can include those reactants known to those of skill in the art. For example, in one embodiment where the amplification to be performed is PCR, the reaction components may contain PCR primers, a sequence-specific fluorescent DNA probe or marker, salts, buffers, surface passivating reagents and the like.

Several different real-time detection chemistries exist to indicate the presence of amplified DNA. Such chemistries are applicable to the present disclosure, where the monitoring of amplified spots within the reaction chamber is desired. Most of these detection chemistries depend upon fluorescence indicators that change properties as a result of the PCR process. Among these detection chemistries are DNA binding dyes (such as SYBR™ Green) that increase fluorescence efficiency upon binding to double stranded DNA. Other real-time detection chemistries utilize Foerster resonance energy transfer (FRET), a phenomenon by which the fluorescence efficiency of a dye is strongly dependent on its proximity to another light absorbing moiety or quencher. These dyes and quenchers are typically attached to a DNA sequence-specific probe or primer. Among the FRET-based detection chemistries are hydrolysis probes and conformation probes. Hydrolysis probes (such as the TaqMan™ probe) use the polymerase enzyme to cleave a reporter dye molecule from a quencher dye molecule attached to an oligonucleotide probe. Conformation probes (such as molecular beacons) utilize a dye attached to an oligonucleotide, whose fluorescence emission changes upon the conformational change of the oligonucleotide hybridizing to the target DNA.

Dyes that may be useful in the practice of the present invention include those that intercalate within strands of nucleic acids. The classic example of such a dye is ethidium bromide. An exemplary use of ethidium bromide for binding assays includes, for example, monitoring for a decrease in fluorescence emission from ethidium bromide due to binding of test molecules to nucleic acid target molecules (ethidium bromide displacement assay). See, e.g., Lee, M. et al. (J Med Chem 36(7):863-870 (1993)). The use of nucleic acid intercalating agents in measurement of denaturation is well known to those in the art. See, e.g., Haugland (Handbook of Fluorescent Probes and Research Chemicals, Molecular Probes, Inc., Eugene, Oreg. (1996)). Dyes that bind to nucleic acids by mechanisms other than intercalation can also be employed in embodiments of the invention. For example, dyes that bind the minor groove of double stranded DNA can be used to monitor the molecular unfolding/ denaturation of the target molecule due to temperature. Examples of suitable minor groove binding dyes are the SYBR Green family of dyes sold by Molecular Probes Inc. (Eugene, Oreg., USA). See, e.g., Haugland (Handbook of Fluorescent Probes and Research Chemicals, Molecular Probes, Inc., Eugene, Oreg., USA (1996)). SYBR Green dyes will bind to any double stranded DNA molecule. When a SYBR Green dye binds to double stranded DNA, the intensity of the fluorescent emissions increases. As more double stranded DNA are denatured due to increasing temperature, the SYBR Green dye signal will decrease. Another suitable dye is LCGreen Plus sold by BioFire Technology, Inc.

Partition-Free Method

Embodiments of the present disclosure are directed towards partition-free quantitation of molecules, including partition-free based amplification and dPCR systems. In particular, an exemplary embodiment of the present disclosure removes the physical partitions in a reaction chamber and instead uses an open shallow amplification chamber. In place of physical partitions or droplets, virtual partitions are established by seeding small quantities of the sample containing genetic material at distances from the other sample "seeds" and by limiting diffusion among the sample seeds during the amplification of the sample as illustrated in FIG. 1.

Figure 2:
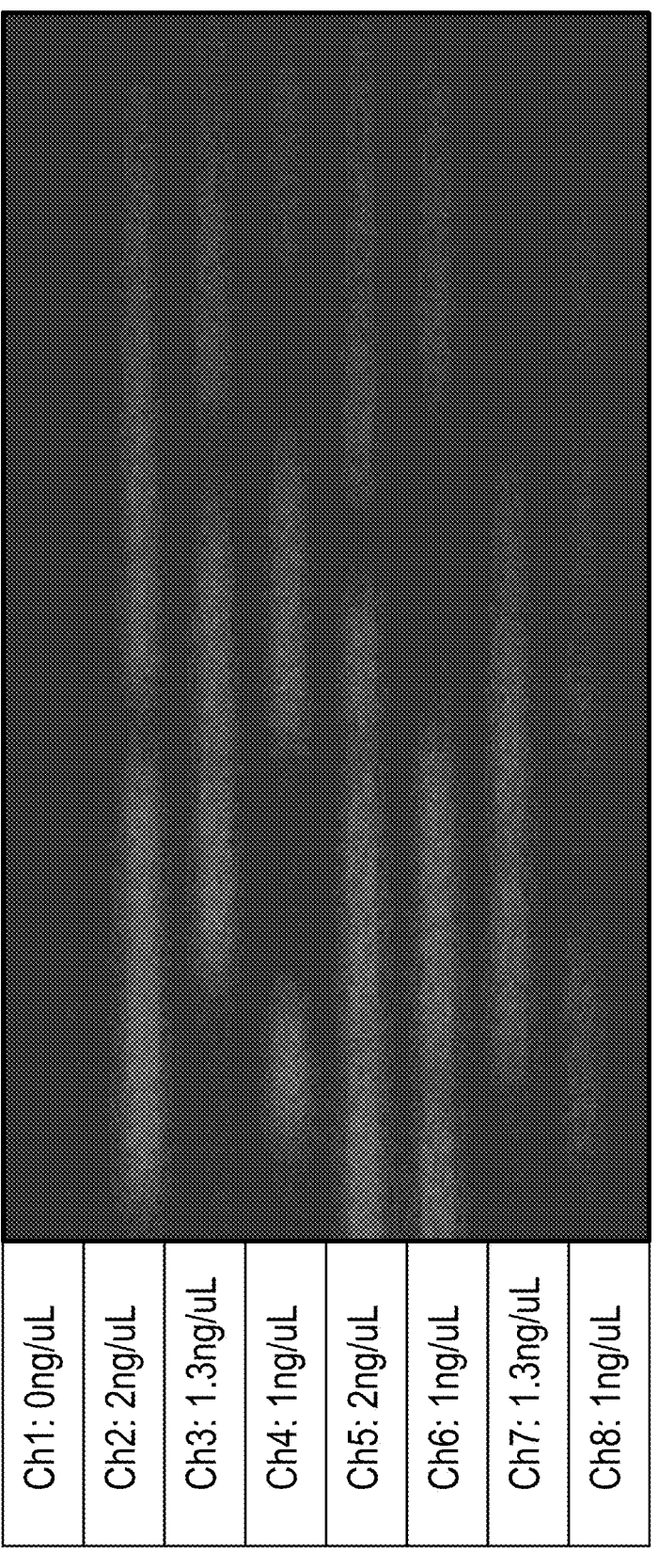
FIG. 2 is a fluorescence image of a PCR showing discrete amplification spots using high speed thermal cycling of 45 cycles within 78 seconds.

FIG. 1 provides a 1-dimensional and 2-dimensional depiction of the partition-free amplification method of the present disclosure. A sample containing genetic material is seeded into a partition free reaction chamber, such that a small amount of genetic material is present at each seeded location. The starting material is sufficiently spread apart that each seed of the sample does not overlap, or has minimal overlap, with other surrounding seeds. In some embodiments, a single copy of the genetic material may be present in the sample at each seeded location. Amplification is performed on the seeded sample, and the amount of genetic material increases while limited diffusion occurs around the seeded location. During and following amplification, an amplification spot is present at each of the seeded locations that successfully underwent amplification as shown in FIG. 2. The partition-free method provides limited diffusion such that the average distance between the amplified spots is comparable to or larger than the average spot size that is determined by the compound diffusion length of the amplified genetic material (amplicons). In this manner, the initial discreteness of the seed starting material can be maintained after amplification, such that each spot can be analyzed independently. Should two or more amplification spots overlap, they can be analyzed as a group.

In one embodiment of the present disclosure, the more seeds or copies of the genetic material in the sample (or in the sample plus reactants) results in an increased number of amplified spots. In one embodiment, the area or number of positive spots over the entire chamber area is related to the starting number of seeds or copies as provided in FIGS. 3 and 4. In one embodiment, the area or number of positive spots can be used to calculate the concentration of the target molecules. In some embodiments, it is desirable to limit the size of the amplified spots to establish high dynamic range (the number of resolvable spots in a given chamber size).

In one embodiment of the present disclosure, the starting material may be any genetic material. In another embodiment, the starting material may be any one or more of DNA, RNA, and cDNA.

While PCR is provided as an exemplary embodiment of the present disclosure to which the partition-free method can be applied, other amplification methods can also be utilized. Thus, embodiments of the present disclosure include application of the partition-free method to amplification or reactions beyond standard PCR. For example, lower speed regular thermal cycling PCR, faster speed PCR, ligase chain reaction, strand displacement amplification, isothermal amplification and loop-mediated isothermal amplification can also be performed using the partition-free methods described herein, among others. In a further embodiment, such amplification and other reactions can also be digitally analyzed with and quantitated, including via the use of active diffusion controls.

In another embodiment, limiting diffusion length results in limiting the size of the amplified spots. In one embodiment, the limited diffusion of the seeded genetic material in the partition-free method is the result of active diffusion control. Active diffusion control can therefore limit the diffusion length of the seeded genetic material-containing sample.

In some embodiments, limiting the diffusion length can include increasing the average distance between the seeded starting materials. For instance, where the starting material is DNA, the number of DNA copies to be seeded in the reaction chamber can be reduced by lowering the starting DNA concentration, allowing the seeded DNA copies to tolerate larger diffusion between the amplified spots.

Increasing Viscosity

In one embodiment, active diffusion control includes increasing the viscosity of the reaction components. In one embodiment, concentrations of the amplification or other reaction reagents can be increased. In another embodiment, cross-linking of the amplification or other reaction reagents can be initiated. In a further embodiment, a viscosity increasing agent can be added to the reactants and starting genetic material.

Viscosity is highly dependent upon molecular structure and molecular weight. Viscosity increasing agents can include PVP, methyl cellulose, glycerol and gelatin. Viscosity increasing agents should be highly viscous at low concentrations and easily form gels, while not inhibiting the desired amplification or other reaction. Other viscosity increasing agents useful in the practice of the present disclosure can include thixotropic, emollient, gallant, cross-linking and other rheology modifying and thickening agents. One of skill in the art would be able to identify other viscosity increasing agents of use in the present partition-free method. Factors for determining the suitability of other viscosity increasing agents include the viscosity of the agent, the compatibility of the viscosity increasing agent (for instance, if performing a PCR reaction, the agent cannot be a PCR inhibitor), and the amount of diffusion observed when the agent is used.

Reducing PCR Time

In another embodiment, active diffusion control can include shortening the length of time of the amplification or reaction. In some embodiments, for instance, when the amplification to be performed is PCR, or otherwise requires thermal cycling, the thermal cycling can be accelerated to have shorter cycle times, or the number of cycles can be reduced.

In some embodiments, reduction of cycle or amplification time can be used to limit the diffusion length. In those instances where the amplification to be performed is PCR, the reduction of cycle time include using a low-noise imaging system to detect positive fluorescence signal early in the amplification process, using high contrast reporter dyes to increase signal-to-noise ratio and terminate PCR cycles early, using methods of heating and cooling to reduce the amount of time for the reaction chamber to reach each desired temperature. In some embodiments, reducing the time for the reaction chamber to reach the desired temperature can include actively cooling the reaction chamber, using hot and cold air for thermal cycling, using a heat transfer substance or device, using optical heating methods, using induction heating methods, using circulating heated fluids, using in-line resistive heaters, using microfluidic channels with in-line resistive heaters using a combination of joule and non-joule heating methods.

In further embodiments, diffusion length can be reduced by accelerating thermal cycling. In some embodiments, accelerating thermal cycling can include using direct or indirect optical or electromagnetic radiation based heating methods. In one non-limiting example, photonic gold can be used as a photothermal medium for highly efficient and uniform light-to-heat conversion. In some embodiments, accelerating thermal cycling is caused by reducing the time to for the reaction chamber to reach each desired temperature In some embodiments, reducing the time for the reaction chamber to reach the desired temperature can include actively cooling the reaction chamber, using hot and cold air for thermal cycling, using a heat transfer substance or device, using optical heating methods, using microfluidic channels with in-line resistive heaters, using a combination of joule and non-joule heating methods.

Reducing PCR Cycling/Thermal Gradients

In some embodiments, active diffusion control can include limiting high temperature steps during amplification. In one embodiment, such active diffusion control can include lowering the denaturation temperature used in an amplification reaction to a temperature lower than is standard, but is still within assay tolerance.

In another embodiment of the present disclosure, fluid flow within the chamber can be reduced in order to reduce the diffusion length. In one embodiment, convectional flow can be decreased by ensuring a uniform temperature distribution in the reaction chamber.

Chamber Geometry

In some embodiments, the reaction chamber can be selected in order to minimize the diffusion length. In one embodiment, the reaction chamber can be selected from a 1-dimensional long channel or a 2-dimensional wide plane. Alternatively or in addition, the chamber depth is relatively shallow to minimize the chance of vertical stacking of multiple seeded starting materials. In some embodiments, the reaction chamber will be a microfluidic channel. In other embodiments, the chamber can be an arbitrary 3-dimensional shape in conjunction with a detection system that can probe spatial sections of the chamber independently. For example, confocal microscopy or light sheet illumination can be used to optically interrogate the entire volume of the chamber. In further embodiments, a 3-dimensional chamber or channel can have dimensions of up to 10 mm×10 mm×10 mm (more practically 3 mm×3 mm×3 mm). A 2-dimensional channel can have dimensions of up to <0.1 mm×100 mm×100 mm (more practically 0.1 mm×15 mm×15 mm), and 1-dimensional channel can have dimensions of up to 0.1 mm×1 mm×10000 mm (more practically 0.1 mm×0.1 mm×2000 m).

Thermal Control

In some embodiments, any controllable thermal cycler or thermal system that can raise and lower the temperature of the reaction chamber in accordance with the desired reaction can be used with the methods and systems of the present disclosure. In one embodiment, the thermal cycler or thermal system can be used to control the temperature in the reaction chamber via a temperature controller. The temperature controller can be a subunit of the controller 604 in FIG. 6 or may be a separate component. The temperature controller, which may be a programmed computer or other microprocessor or analog temperature controller, sends signals to a heating device based on the temperature determined by a temperature sensor (which may comprise one or more temperature sensors, such as, for example, a thin film resistive thermal detectors (RTD) or thin-film thermistor, or a thin-film thermocouple thermometer, or non-contact IR thermometer). In this way, the temperature of the reaction chamber can be maintained at the desired level or cycled through a defined sequence. According to some embodiments of the present disclosure, the reaction chamber can also be cooled by a cooling device (for example, to quickly bring down the channel temperature), which may also be controlled by the temperature controller. In one embodiment, the cooling device could be a peltier device, heat sink, or forced convection air cooled device, for example.

Figure 45:
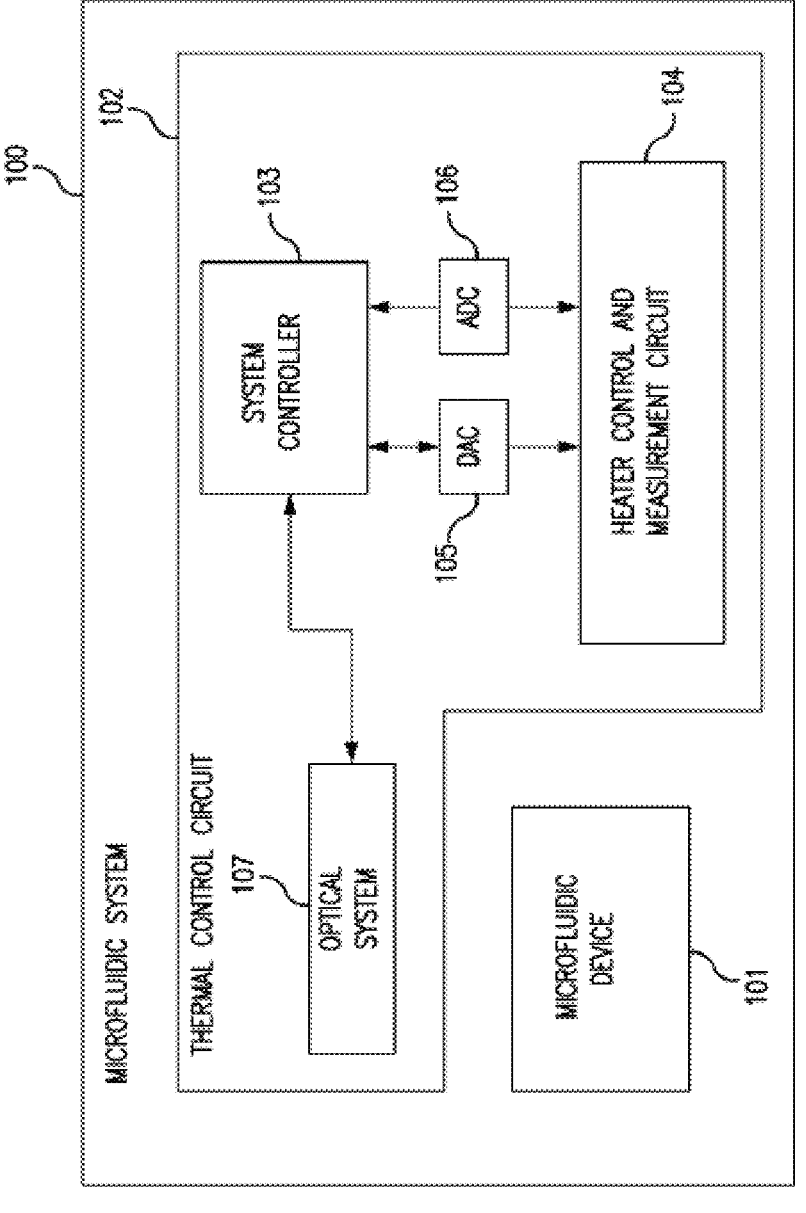
FIG. 45 depicts a block diagram illustrating functional units of a microfluidic system.

Other details of heater systems that can be used in connection with the methods and systems of the present disclosure are described in application U.S. Application Publication No. 2011-0048547, entitled "Microfluidic Systems And Methods For Thermal Control," the disclosure of which is hereby incorporated herein by reference in its entirety. One such system is depicted in FIG. 45, which corresponds to FIG. 1 of U.S. Application Publication No. 2011-0048547. FIG. 45 illustrates a microfluidic system 100 according to one embodiment of the present invention. As shown in FIG. 45, microfluidic system 100 has a microfluidic device 101 and a thermal control circuit 102. Thermal control circuit 102 has a system controller 103, heater control and measurement circuit 104, digital to analog converter (DAC) 105 and analog to digital converter (ADC) 106. Although DAC 105 and ADC 106 are shown in FIG. 45 as separate from system controller 103 and heater control and measurement circuit 104, DAC 105 and ADC 106 may alternatively be part of system controller 103 or heater control and measurement circuit 104. In addition, thermal control circuit 102 may include an optical system 107 to monitor microfluidic device 101. Resistive temperature detectors (RTDs) can be used as heating elements, but can also be used in an alternating polarity concept to minimize waste heat and to deliver high quality temperature measurements without using the RTDs as heating elements. This configuration may be desirable if one has a need to determine the temperature on the microfluidic device 101 but has some other means of heating (e.g., when the device is heated by an external means).

Image Acquisition

In some embodiments, the amplification spots can be visualized through fluorescence using either intercalating dyes or fluorescent probes. In other embodiments, spot visualization can use other optical techniques such as bright or dark field imaging assisted by enhanced scattering or phase-contrast imaging.

In other embodiments, detection of the amplified spots is simpler than traditional methods as it only needs to measure the amplified spot; unlike in traditional dPCR, there is no need to recognize each partition or droplet that may need a high resolution imaging. In some embodiments, low resolution imaging is sufficient to image the amplified spots, and reduces the total PCR time with a shorter exposure time per image than when acquiring traditional real-time PCR data.

According to one embodiment, image acquisition can utilize an optical system that is in optical communication with the reaction chamber. The optical system can include one or more sensors (e.g., a camera), which may have a lens barrel and/or extension tubes depending on the desired configuration. The optical system can also include one or more excitation sources, such as an LED or other appropriate light source. According to one, the detector can be a digital color camera that is capable of recording data at video frame rates, such as, for example, up to 20-30 frames per second. A non-limiting example would be the Canon EOS 5DMkII Digital SLR camera. The lens assembly can include an appropriate fluorescence emission filter. In this exemplary embodiment, the emission filter can be a dual bandpass filter with a pass-band for the DNA binding dye LC Green Plus from Idaho Technology. However, alternative filters may be substituted for appropriate alternative combinations of fluorescent dyes.

Other details of imaging systems that may be used in connection with the systems and methods of the present invention, as well as further details regarding their use, are described in U.S. Provisional Patent Application No. 61/378,471, entitled "Optical System For High Resolution Thermal Melt Detection," and U.S. application Ser. No. 13/222,487 claiming priority therefrom, the disclosures of which are hereby incorporated herein by reference in their entirety.

Thermal Melting

In some embodiments, the partition-free analysis can be also used for quantitative DNA mutation detection in conjunction with a melting analysis, including but not limited to a high resolution melting analysis. The in-situ fluorescence imaging enables to collect melting curve for individual amplicon spots or clusters. Genotyping through the acquired melting curve as well as digital quantification of clusters can provide the allelic frequency of mutant copies in the background of wild type DNA copies.

Genotyping and Allelic Frequency

In another embodiment, the amplification reactants may include one or more labelled probes. Following amplification of the nucleic acids in the presence of one or more labelled probes, multicolor detection can be used to determine one or more genotypes of the amplified nucleic acids. In a further embodiment, allele frequency is also determined based on the multicolor detection. One of skill in the art will understand the manner in which traditional dPCR can be used for genotyping and allelic frequency analysis, and such methods can be used with the partition-free method provided in this disclosure.

Image Processing

The optical detection system obtains images of the nucleic acid sample(s) in the chamber. In one aspect, images can be obtained prior to the start of the amplification, during the amplification, and after the amplification. In another aspect, one or more images can be obtained during each cycle of the amplification, and at any or all of the phase of denaturation, annealing and extension.

Figure 8:
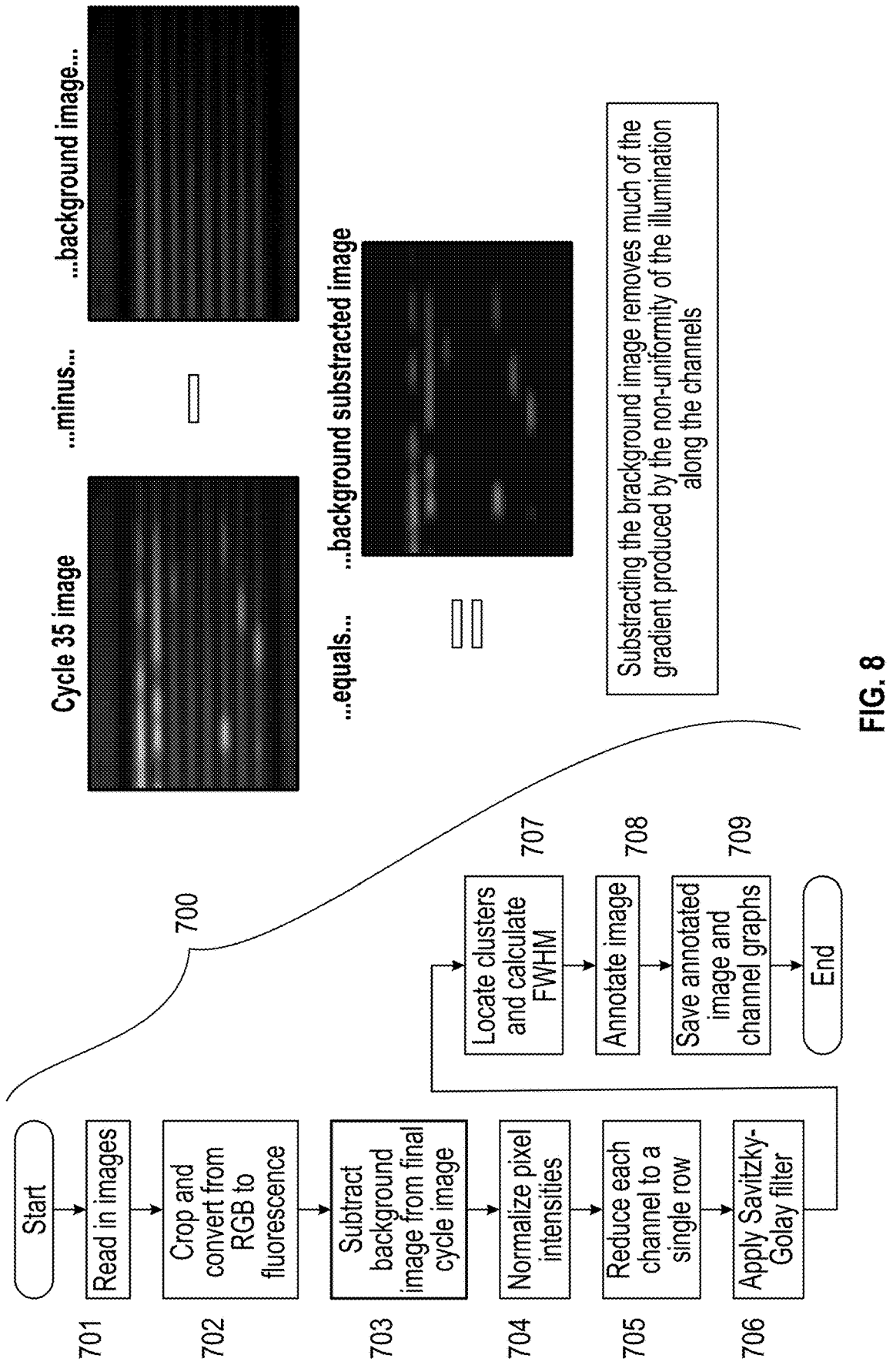
FIG. 8 is a flow chart of the image processing process and images depicting the subtraction of the background image.
Figure 9:
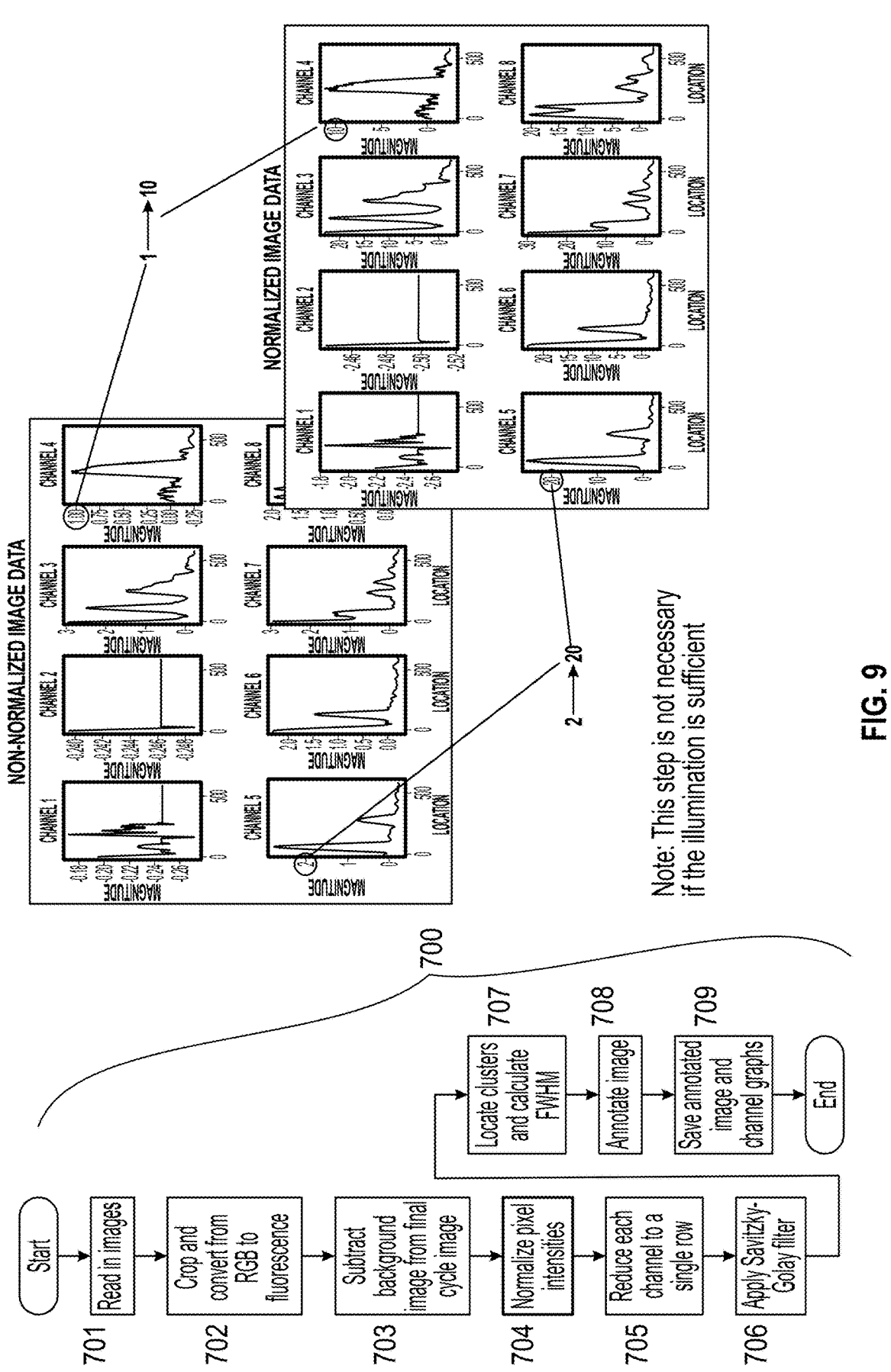
FIG. 9 is a flow chart of the image processing process and graphs depicting normalization of the pixel intensities.
Figure 11:
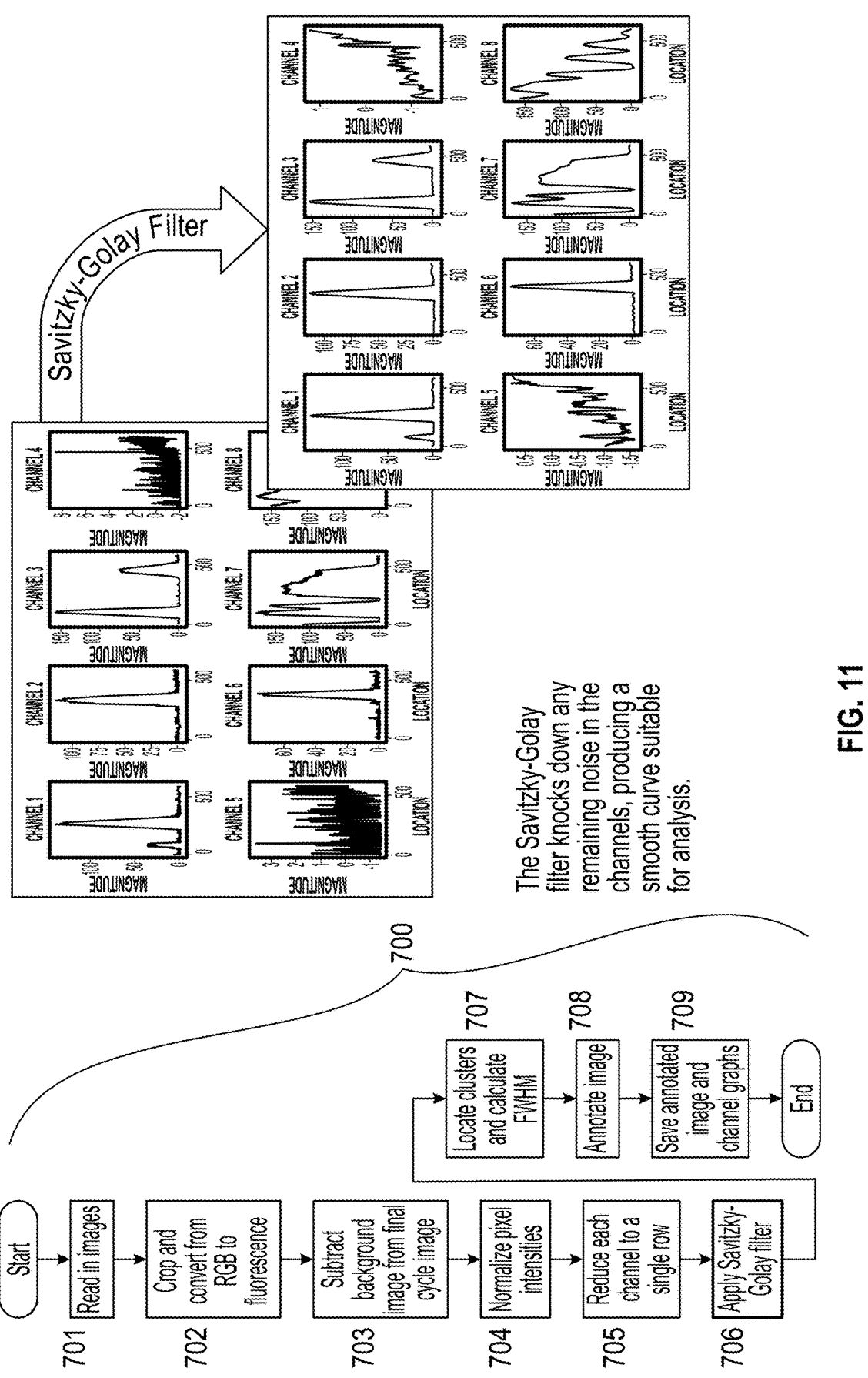
FIG. 11 is a flow chart of the image processing process and graphs depicting the result of application of the Savitzky-Golay filter.

After the optical detection system has obtained images of the nucleic acid samples, in step 701 of process 700, the images are exported, uploaded, or otherwise read in to a controller unit, which processes the images (FIG. 7). In step 702, the images are cropped and converted from RGB to fluorescence:

$$f = \frac{2g + b}{3},$$

wherein f-fluorescence, g=green RGB component and b=blue RGB component. The background image is subtracted from the final cycle image in step 703 (FIG. 8), and the pixel intensities are normalized in step 704 (FIG. 9). Each channel is reduced to a single row in step 705 (FIG. 10), and a Savitzky-Golay filter is applied in step 706 (FIG. 11).

Savitsky-Golay filters are low pass, Finite Impulse Response (FIR) derivative filters, and their application to any dynamical signal is obtained through the convolution of the FIR filter parameters with the raw signal. When the spacing of the independent variable is uniform, the filtered results can give first order and higher order derivatives of the dependent variable relative to the independent variable equivalent. The effect of such a filter is equivalent to a moving polynomial fit, followed by the evaluation of the derivative of that polynomial evaluated at the center of the window. The degree of filtering depends on the polynomial order and window size (or number of points). The use of Savitzky-Golay filter in step 706 removes any remaining noise in the channels, producing a smooth curve suitable for analysis.

U.S. Patent Application Publication No. 20180111125 describes PCR with rapid temperature cycling which included an example that used heating at a programmed melting rate of 50° C./s to 95° C. with an initial denaturation hold of 30 s, followed by 40 cycles of cooling at 12.5° C./s to the annealing temperature with a 2 s hold, heating to 72° C. at 1.8° C./s with a 3 s hold, and heating at 50° C./s to 95° C. with a 2 s hold. U.S. Patent Application Publication No. 20180111125 additionally classified melting rates of 0.13° C./s as slow, 8° C./s as fast, and 32° C./s as very fast. Current real-time PCR instruments that claim high resolution melting vary in the melting rates recommended. Rates from 0.005° C./s to about 0.1° C./s appear standard on currently available instruments. U.S. Patent Application Publication No. 20180111125 described the invention as a method and system for performing a nucleic acid high speed melting analysis where the temperature is increased by the thermal system at the ramp rate selected from a range of from 1° C./s to 50° C./s.

Figure 12:
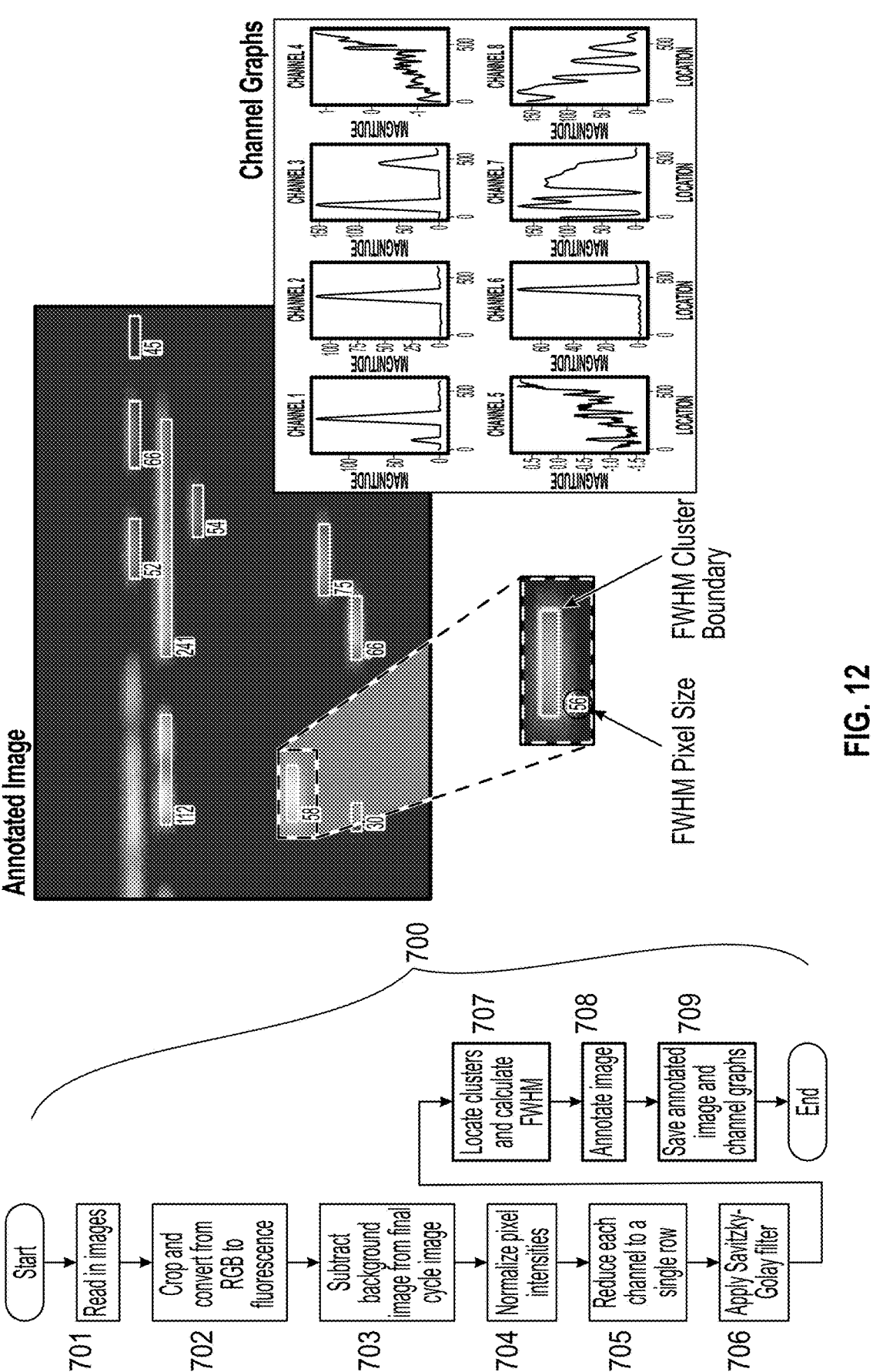
FIG. 12 is a flow chart of the image processing process and an image and graph depicting the annotated image and channel graphs.

In step 707, clusters are located, and the full-width-half-maximum (FWHM) cluster boundary is determined (FIG. 12). The FWHM cluster boundaries are indicative of single amplified spots within the chamber. The images are annotated in step 708, and are saved along with channel graphs that show magnitude vs. location for the pixels within the FWHM cluster boundary.

Quantification Method

The channel graphs provided in step 708, can provide data to allow quantification of the amount of particles or nucleic acids within a single partition. FIG. 13 provides illustrative data that can be obtained by the simulations described in the examples, or through analysis of images as provided above, for example the channel graphs provided in FIG. 12. If the FWHM cluster boundaries overlap, the magnitudes of the clusters can be added to obtain a combined signal. A threshold can be set for what magnitude constitutes a positive signal. By applying that threshold to the data, positive (P) and negative (N) regions of the channel are determined. Using a Poisson distribution equation, the ratio of the negative portions of the reaction chamber (for example, a channel) to the total reaction chamber width can be used to estimate quantification ($\lambda$), wherein $\lambda$ is the average count in a single partition:

$$P(0) = \frac{\text{Sum of negative channel lengths}}{\text{Total channel length}} \Rightarrow \lambda = -\ln P(0).$$

The value of $\lambda$, when used in combination with the number of amplified spots, can be used to determine the total number of particles or nucleic acids within a sample or a portion of a sample.

Furthermore, when used in a simulation, repeating the simulation over a range of $\lambda$ values produces a precision curve from which the dynamic range can be determined. By selecting a desired precision value (for example, 5, 10, 15 or 20%), a horizontal line can be drawn across the graph of the precision curve, which horizontal line will intersect the curve at two points. Vertical lines drawn at those two points will intersect the x-axis to provide the $\lambda$ values at the intersection points. The difference between the lambda values is the dynamic range. Using a Monte Carlo simulation of Poisson distributions, dynamic ranges as various levels of precision can be calculated for desired numbers of partitions (FIG. 14). Plotting dynamic range vs. cluster size in (mm) allows the user to select the desired cluster size. The user can then adjust the parameters of the sample and the amplification reaction to result in the desired cluster size.

Method Overview

Figure 5:
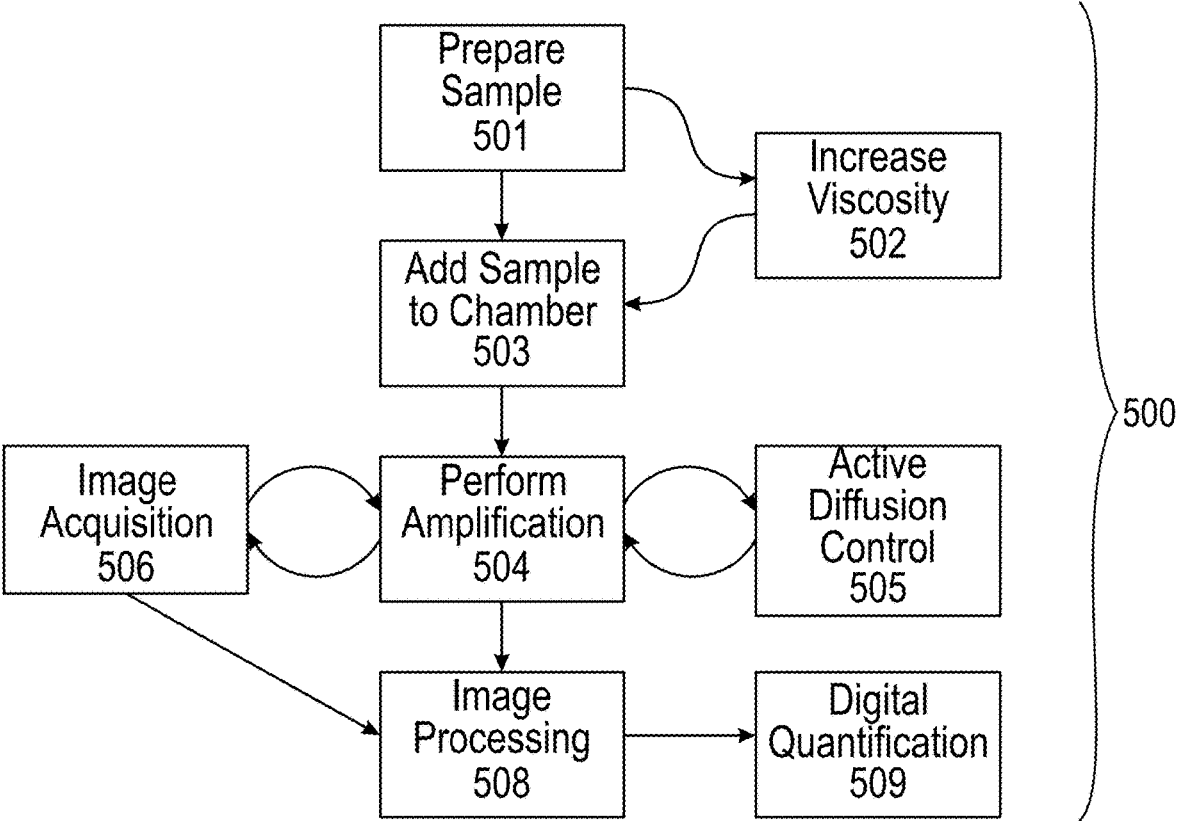
FIG. 5 is a flow chart depicting a partition-free process according to the present disclosure.

Thus, as shown in FIG. 5, there is provided a method 500 for partition-free quantification of molecules comprising the steps of: preparing a sample (step 501), introducing a sample into a chamber (step 503); wherein the sample comprises one or more nucleic acids, and wherein the nucleic acids are distributed across the chamber; providing a thermal system in thermal communication with the sample; providing an optical detection system in communication with the one or more nucleic acid samples, wherein the optical detection system comprises an imaging system; performing amplification of the one or more nucleic acids (step 504); obtaining one or more images of the amplified nucleic acids (step 506); processing the images (step 508) and digitally quantifying (step 509) the amplified nucleic acids based on fluorescence distribution across the chamber.

The amplification reaction is selected from polymerase chain reaction, ligase chain reaction (LCR), strand displacement amplification (SDA), isothermal amplification and loop-mediated isothermal amplification, as well as fast versions of these amplification reactions, wherein the number of cycles is reduced, the length of time for the cycles is reduced, the temperatures required by the amplification are reduced, or any combination thereof. For example, a faster polymerase chain reaction is described in U.S. Patent Application Publication No. 20180111125, which is incorporated herein by reference.

In some embodiments, the present disclosure relates to actively controlling the diffusion of the sample as in step 505. In some instances, actively controlling the diffusion of the sample can include adding a viscosity increasing agent to the sample (step 502), reducing the temperatures that the sample is subjected to during the amplification, increasing the amplified molecule size, and reducing the length of time of the amplification. In some embodiments, the viscosity increasing agent can include polyvinylpyrrolidone, methyl cellulose, glycerol, gelatin, cross-linking reagents, increased sample molecular concentrations, and the like, including any described herein or identified by one of skill in the art. Other viscosity increasing agents useful in the practice of the present disclosure can include thixotropic, emollient, gallant, cross-linking and other rheology modifying and thickening agents.

In further embodiments, reducing the length of time of the amplification comprises minimizing the number of amplification cycles or performing fast thermal cycling (step 505). In still further embodiments, reducing the length of time of the amplification causes the amplified nucleic acids to remain spatially close to the starting seed nucleic acid in the sample.

In some embodiments, reducing the length of time of the amplification is achieved by obtaining images (step 506) of the amplified spots early in the amplification process, providing a high-contrast reporter dye in the sample, or providing a thermal system that quickly allows the desired temperatures to be reached.

In some embodiments, the images of the amplified spots (step 506) are obtained early in the amplification process using a low-noise imaging system to detect a positive fluorescence signal from the amplified nucleic acids. In some embodiments, images of the amplified spots (step 506)

are captured prior to amplification (essentially resulting in an image of the chamber without any amplified spots), one or more times per amplification cycle, and/or once amplification has been completed.

In other embodiments, accelerating thermal cycling includes providing a thermal system that utilizes direct optical, indirect optical, electromagnetic radiation, a heat transfer substance or device, in-line resistive heaters, hot air, inductive heating, circulating heated fluid, microfluidic channels with in-line resistive heaters, or joule or non-joule heating methods, either alone or in any combination to reduce the amount of time it takes for the reaction chamber to be heated or cooled to each required temperature.

In some embodiments, the partition-free quantitation method additionally comprises performing a melting analysis and/or obtaining melting curves for the one or more amplified nucleic acids. In further embodiments, the one or more nucleic acids are genotyped. In other embodiments, the digital quantification and genotyping results are combined to provide the allelic frequency of mutant DNA copies in the background of wild type DNA copies.

In further embodiments, wherein digital quantification includes counting a number of amplified spots or unamplified spots and applying statistics to calculate the number of DNA copies present in the chamber volume. In some embodiments, digital quantification includes measuring overall area of amplified/unamplified spots. In yet further embodiments, the optical detection system comprises fluorescence imaging or bright or dark field imaging assisted by enhanced scattering or phase-contrast imaging. In other embodiments the imaging system visualizes amplified spots by fluorescence detection either during amplification or at the end of amplification. In other embodiments, following visualization of the amplified spots, the amount of fluorescence is measured. In other embodiments, the digital quantification includes measuring overall fluorescence intensity of fluorescence images or an intensity of positive/negative signals generated by other optical techniques. Alternatively or in addition, digital quantification can include combining (i) counting amplified/non-amplified spots and (ii) spot intensity generated by fluorescence or other optical techniques.

Systems for Amplification

Figure 6:
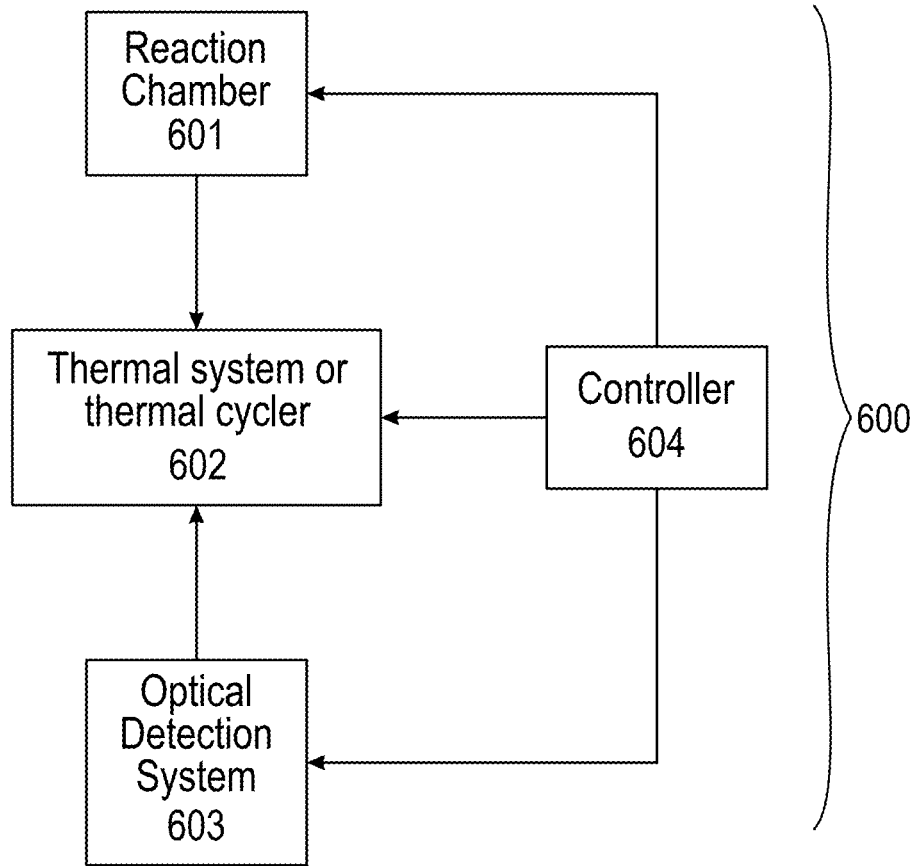
FIG. 6 is a black box diagram depicting a system according the present disclosure.

In some embodiments, and as shown generally in FIG. 6, there is provided a system 600 for quantification of molecules comprising a thermal cycler 602; a reaction chamber or cartridge 601 detachably coupled to the thermal cycler 602, having a region for receiving a nucleic acid sample wherein the region is free of partitions; a detector 603 for detecting fluorescence; and a controller 604 for performing a digital PCR process of the nucleic acid sample received in the region. In some embodiments, the cartridge 601 is a simplified consumable design that does not need the physical partitioning of a reaction mix. In other embodiments, the system 600 functions using a simplified workflow without a separate partitioning step, simplifying the system design and decreasing user hands-on steps, significantly shortening the length of the workflow.

In other embodiments, the controller 604 initiates a polymerase chain reaction process for amplifying the nucleic acid sample in the area, using the thermal cycler 602, wherein the amplified nucleic acid sample is visualized by fluorescence using the optical detection system 603. In some embodiments, the controller 604 additionally determines a distribution of amplified nucleic acids from the sample in the region that is free of partitions, based on fluorescence detected by the detector 603. In yet other embodiments, the controller 604 digitally quantifies the received nucleic acid sample based on the detected distribution. In some embodiments, digital quantification includes measuring overall fluorescence intensity of fluorescence images or an intensity of positive/negative signals generated by other optical techniques.

For the purposes of the present disclosure, all amplification and/or thermal melting experiments described in the present examples were performed on a system as described in U.S. Pat. No. 10,363,558, issued Jul. 30, 2019, the disclosure of which is incorporated herein by reference in its entirety.

A device that may be used in connection with systems and methods of the present disclosure may include features other than, or in addition to, those described above.

Definitions

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "under" "beneath", "below", "lower", "above", "upper", "proximal", "distal", and the like, may be used herein for ease of description to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly. Similarly, the relative spatial terms "proximal" and "distal" may also be interchangeable, where applicable.

The term "cluster," as used herein, is interchangeable with the word "spot", as used to refer to a grouping of amplified molecules surrounding the location of a seed molecule.

The term "about," as used herein means, for example, within 10%, within 5%, or less. In some embodiments, the term "about" may mean within measurement error.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

It will be appreciated that the methods and compositions of the instant disclosure can be incorporated in the form of a variety of embodiments, only a few of which are disclosed herein. Variations of those embodiments may become apparent to those of ordinary skill in the art upon reading the foregoing description. The inventors expect skilled artisans to employ such variations as appropriate, and the inventors intend for the disclosure to be practiced otherwise than as specifically described herein. Moreover, any combination of the above-described elements in all possible variations thereof is encompassed by the disclosure unless otherwise indicated herein or otherwise clearly contradicted by context.

Additionally, while the processes described above and illustrated in the drawings are shown as a sequence of steps, this was done solely for the sake of illustration. Accordingly, it is contemplated that some steps may be added, some steps may be omitted, and the order of the steps may be rearranged.

EXAMPLES

Simulation

A Python simulation was created to compare dPCR results for the scenario of a single nucleic acid copy in a channel, with 30 cycles of an integrative random diffusion through a three step PCR reaction (denaturation, annealing and extension) with duplication of every particle at its current location at the end of the extension period. The output of the simulation was a particle distribution profile along the length (x-axis) of the channel that was used to estimate the size of the resulting cluster or spot. FIG. 15 is a diagram illustrating the simulation conditions.

The simulations utilized a long micro-channel of a rectangular cross-section of 180 μm in width and 20 μm in depth, with no limit to the length (FIG. 16). A single DNA copy was assumed at the start of the simulation, with glycerol in water included in the reaction mixture as an additive to adjust viscosity. The PCR was assumed to start from a single strand copy, with 100% efficiency of the reaction. No hot start was provided for the reaction as it did not contribute to the total diffusion length. The copies were assumed to bounce off the channel walls in both the y and z directions. The time increment was fixed at 0.1 sec. The temperature increment varied depending on the total desired PCR time. Diffusion of the particle(s) at each simulation step was calculated according to the Stokes-Einstein equation, as illustrated in FIG. 17.

Figure 18:
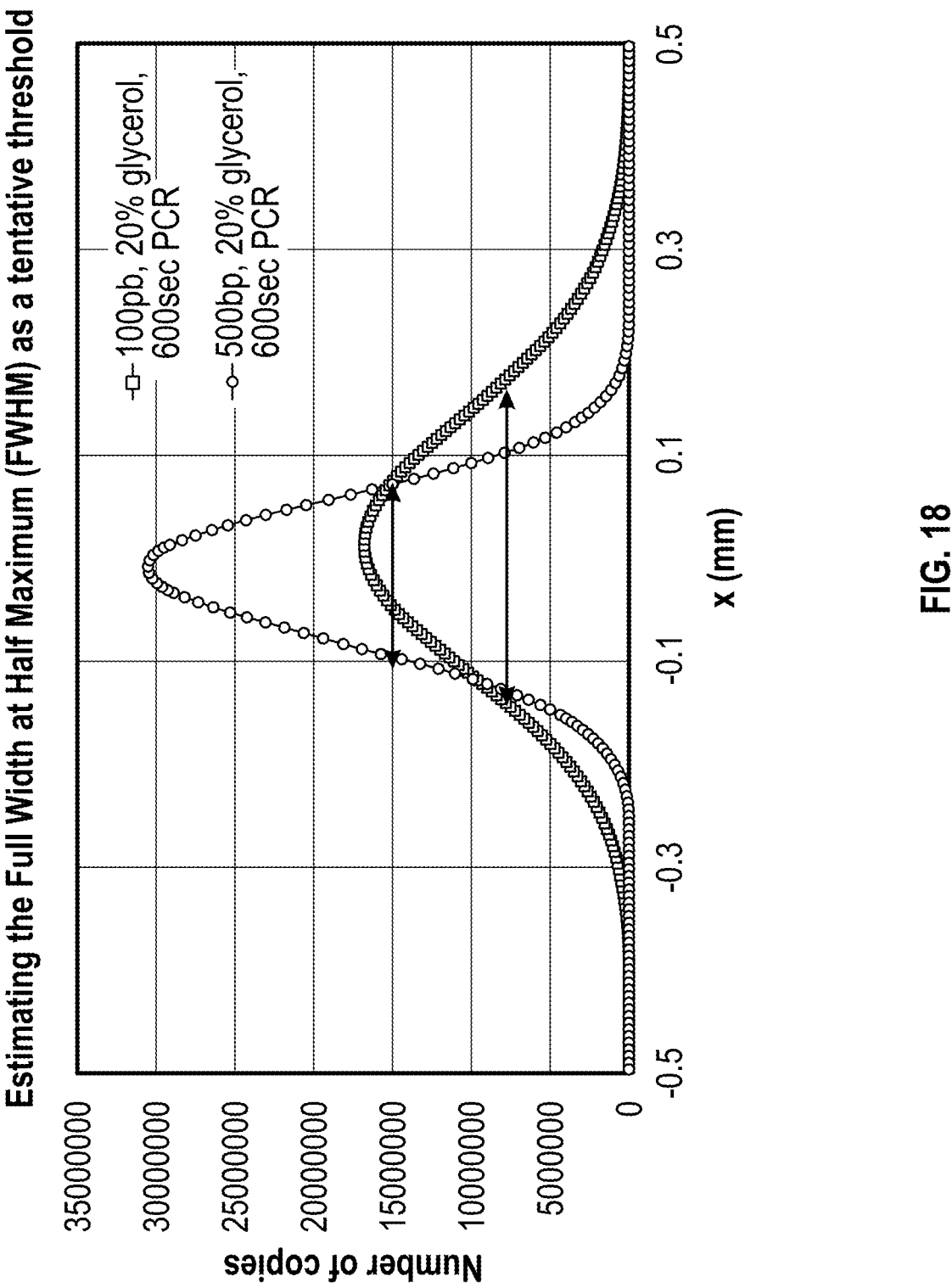
FIG. 18 is a chart showing the FWHM value of the resulting cluster profile from the simulation.
Figure 19:
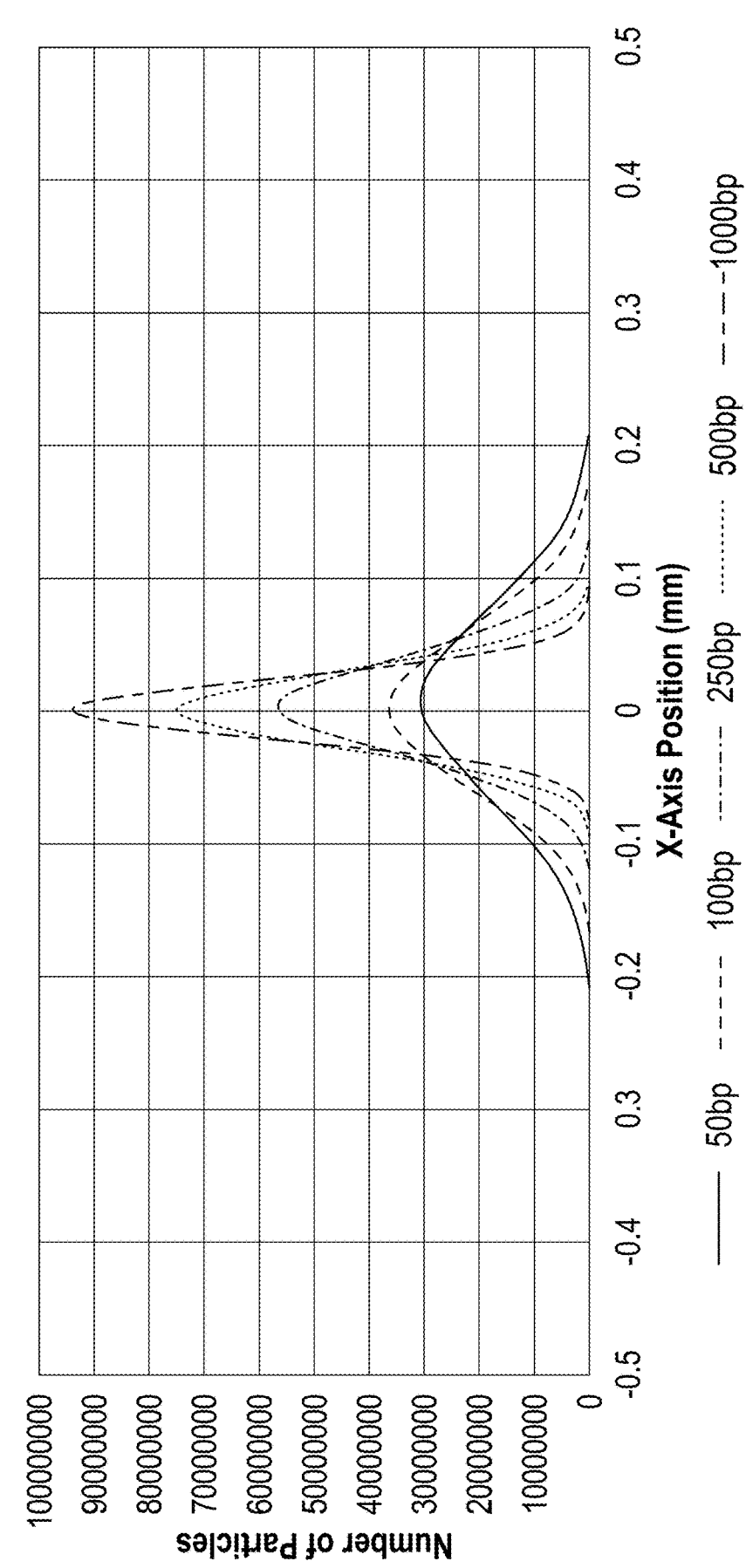
FIG. 19 is a chart showing the output of the simulation at each of the 5 particle sizes.

A total of five particle sizes (50, 100, 250, 500 and 1000 base pairs) were simulated at each of five PCR reaction lengths (1, 4, 7, 10, 13 minutes) at each of three glycerol concentrations (0, 12.5, 25%) for a total of 75 simulations. FIG. 19 illustrates the output at each of the 5 particle sizes. Cluster sizes were measured using a calculation of the FWHM value of the resulting (largely Gaussian) cluster profile (FIG. 18).

Proof of Concept

To show feasibility of the proposed concept, a proof-of-concept experiment was performed with a 1-D long micro-fluidic PCR chamber that has a high speed thermal cycling capability using resistive heaters built into the chip. This provided a relevant test case for shortening PCR time to actively limit diffusion. The dimension of the PCR chamber was a long micro-channel of a rectangular cross-section of 180 μm in width and 20 μm in depth. The total observable channel length was ~7.5 mm. Each cartridge had eight channels that could run multiple PCR reactions simultaneously. Each PCR channel was loaded with PCR mixture having different DNA concentrations (0, 1, 1.3, 2 ng/μL final concentration) and 45 cycles of thermal cycling were performed with fluorescence images captured for monitoring the PCR progress using LC green intercalating dye in the mix. The high speed thermal cycling system completed 45 PCR cycles within 78 seconds. FIG. 2 is the fluorescence image taken after 73 seconds of PCR and it shows discrete bright cluster patches after PCR amplification.

The discrete cluster patches suggested that high speed thermal cycling was able to maintain the digital signature of individual copies spread in the PCR mix after PCR amplification. Amplification around the individual copy was localized due to the limited diffusion, and every fluorescence patch represented the presence of an initial seed nucleic acid copy at that location.

Figure 3:
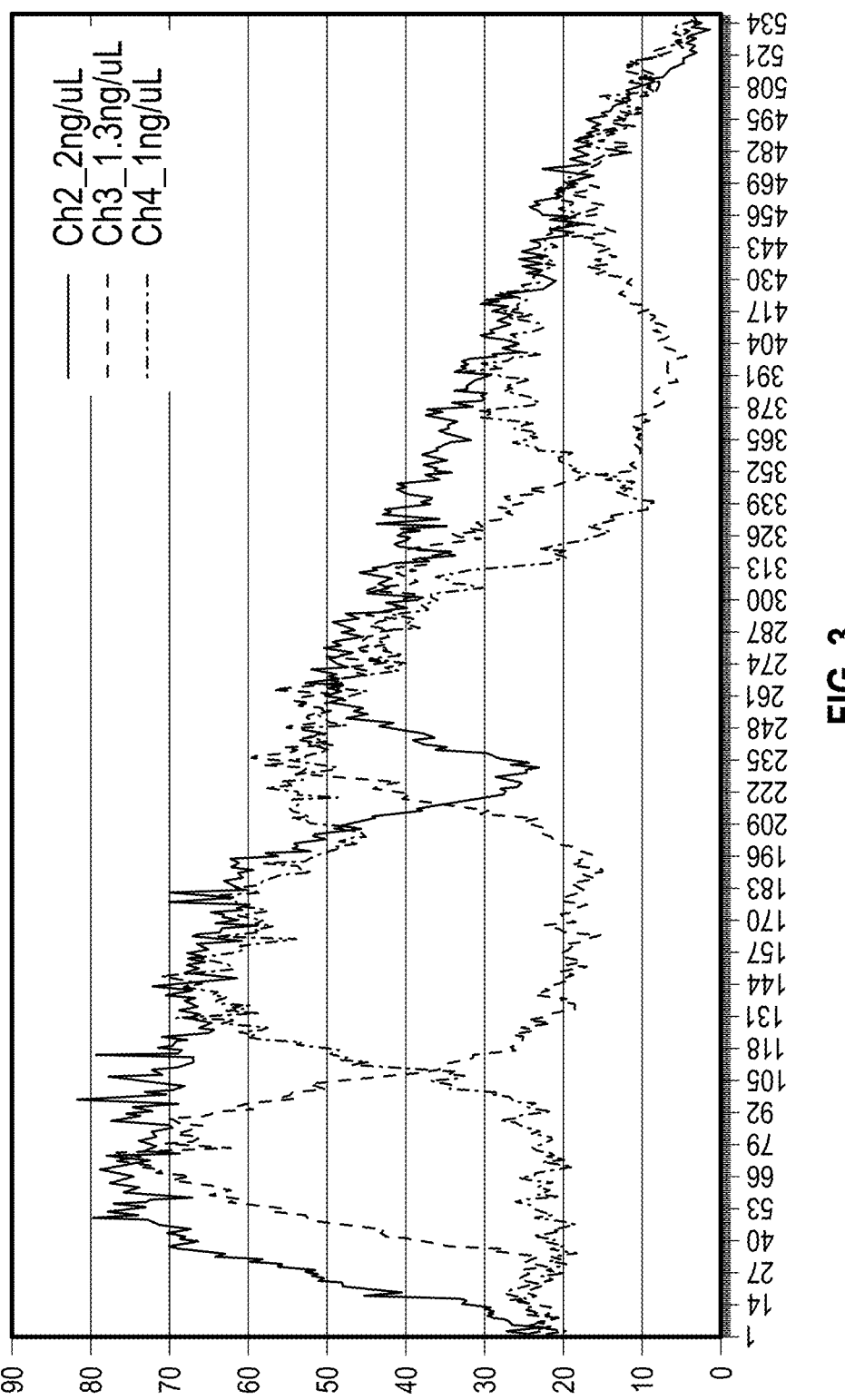
FIG. 3 is a fluorescence intensity profile along the channel axis with three DNA concentrations. The skewed overall intensity profile comes from the illumination pattern of the detection hardware.

This localized amplification visualized by fluorescence could be used to estimate the number of starting copies in the reaction chamber by digital analysis of the fluorescence image. Two analysis methods were applied to check the relationship between fluorescence patches and the starting concentrations. First, fluorescence peaks were observed along the channel axis from the horizontal intensity profiles of each channel as illustrated in FIG. 3. The skewed overall intensity profile comes from the illumination pattern of the detection hardware. The highest 2 ng/μl concentration channel had a broad intensity profile with a single dip along the channel axis while lower concentration reactions showed more discrete peaks. This trend was expected since the lower DNA concentration further separates seed DNA copies from each other. Based on this result, the proportion of the channel length with bright fluorescence can be related to the number of starting copies without considering peak intensity heights.

Figure 4:
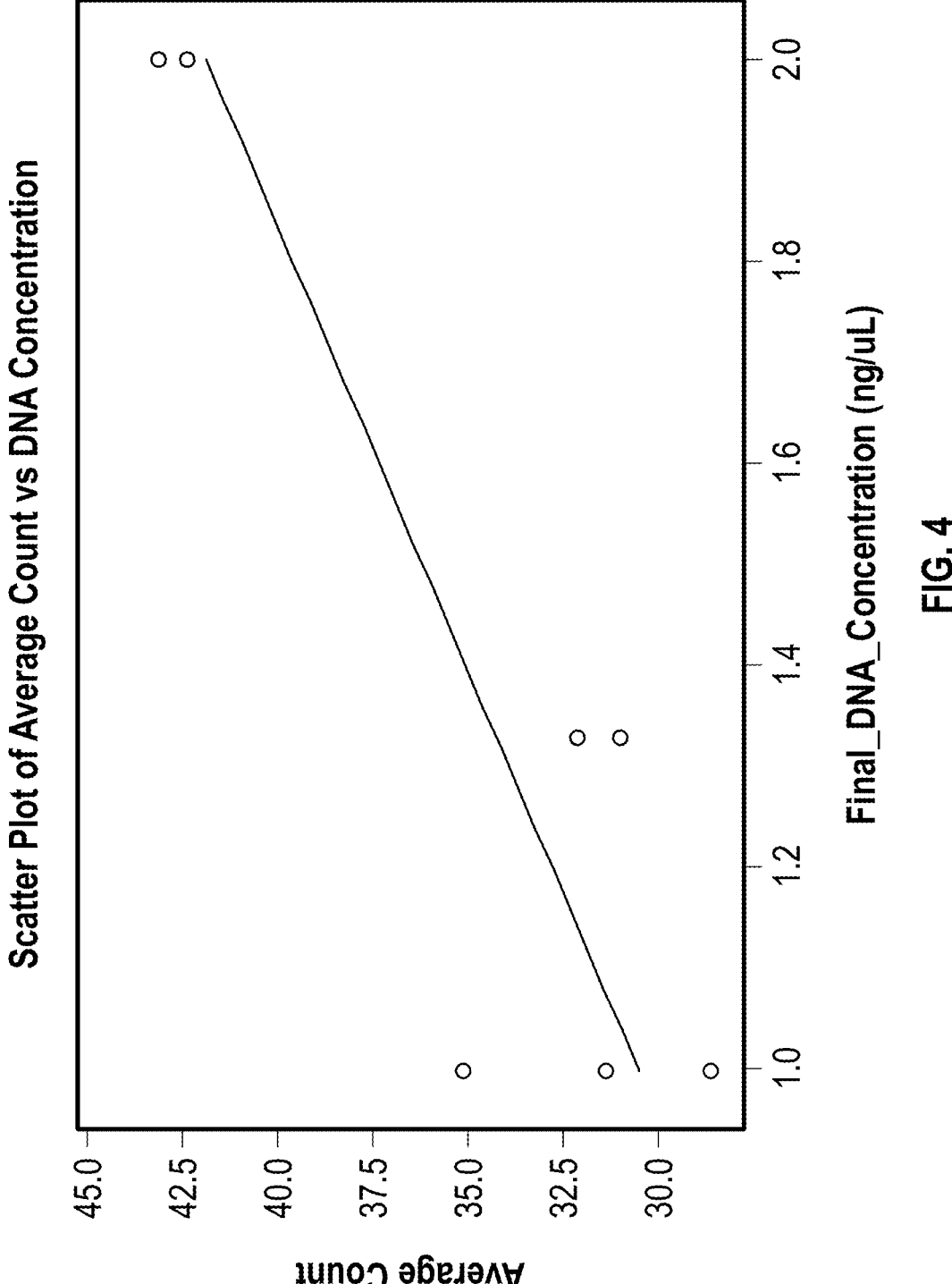
FIG. 4 is a scatter plot of average channel intensity vs. DNA concentration with a linear regression fit. Each data point represents a single channel.

In addition, the relationship between overall channel fluorescence intensity and starting DNA concentration was considered. The overall fluorescence intensity was believed to reflect what portion of the channel is covered by amplicon cluster patches. FIG. 4 shows the result with a linear regression fit and the fit looks good with 78.5% R-square value, confirming the relationship between the overall fluorescence intensity vs starting DNA concentrations as expected in this proposed application.

Increasing Viscosity
Additive Testing

Figure 27:
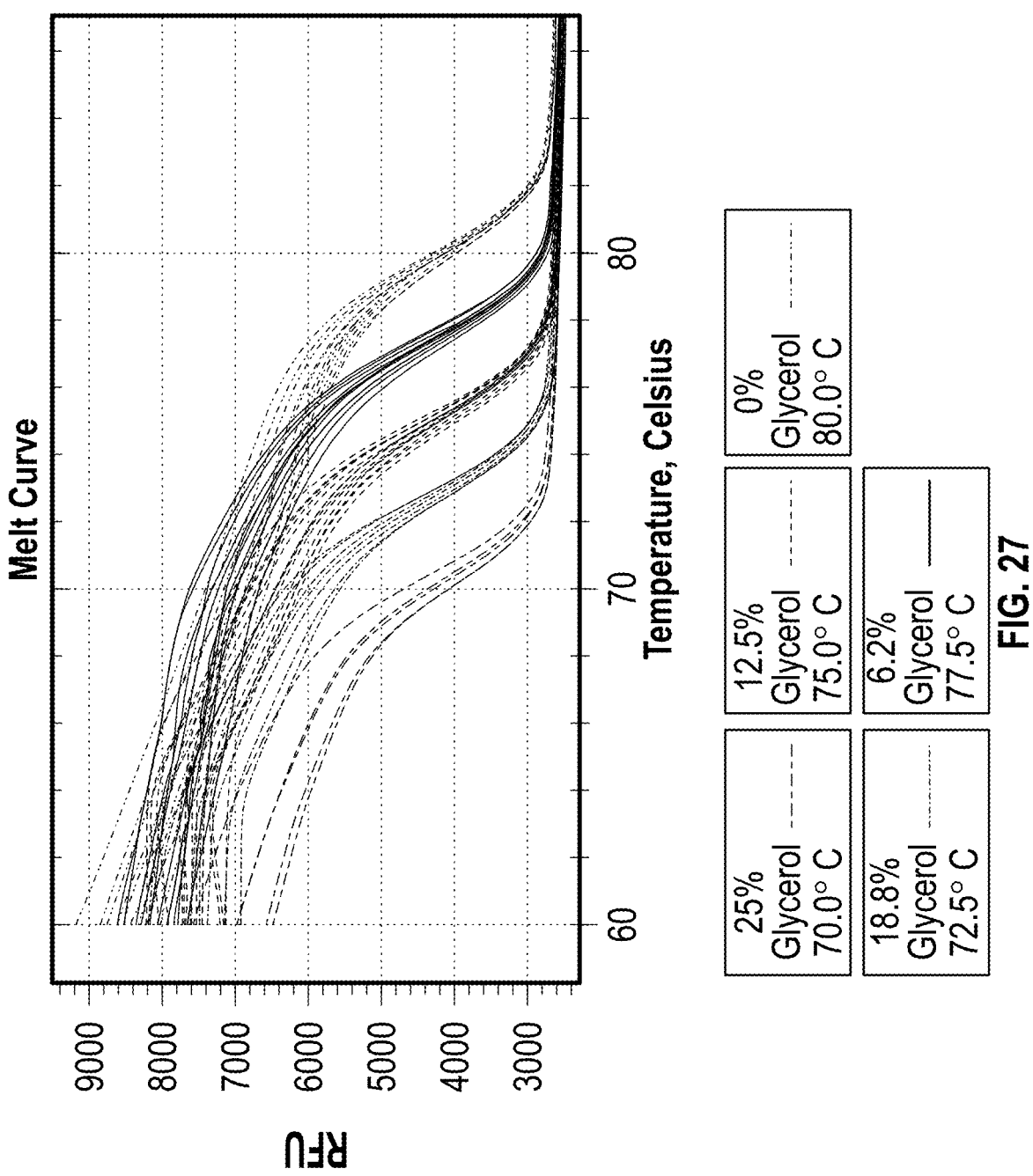
FIG. 27 is a chart showing melting temperature shift with increasing concentration of glycerol.
Figures 28A, 28B, 28C, 28D:
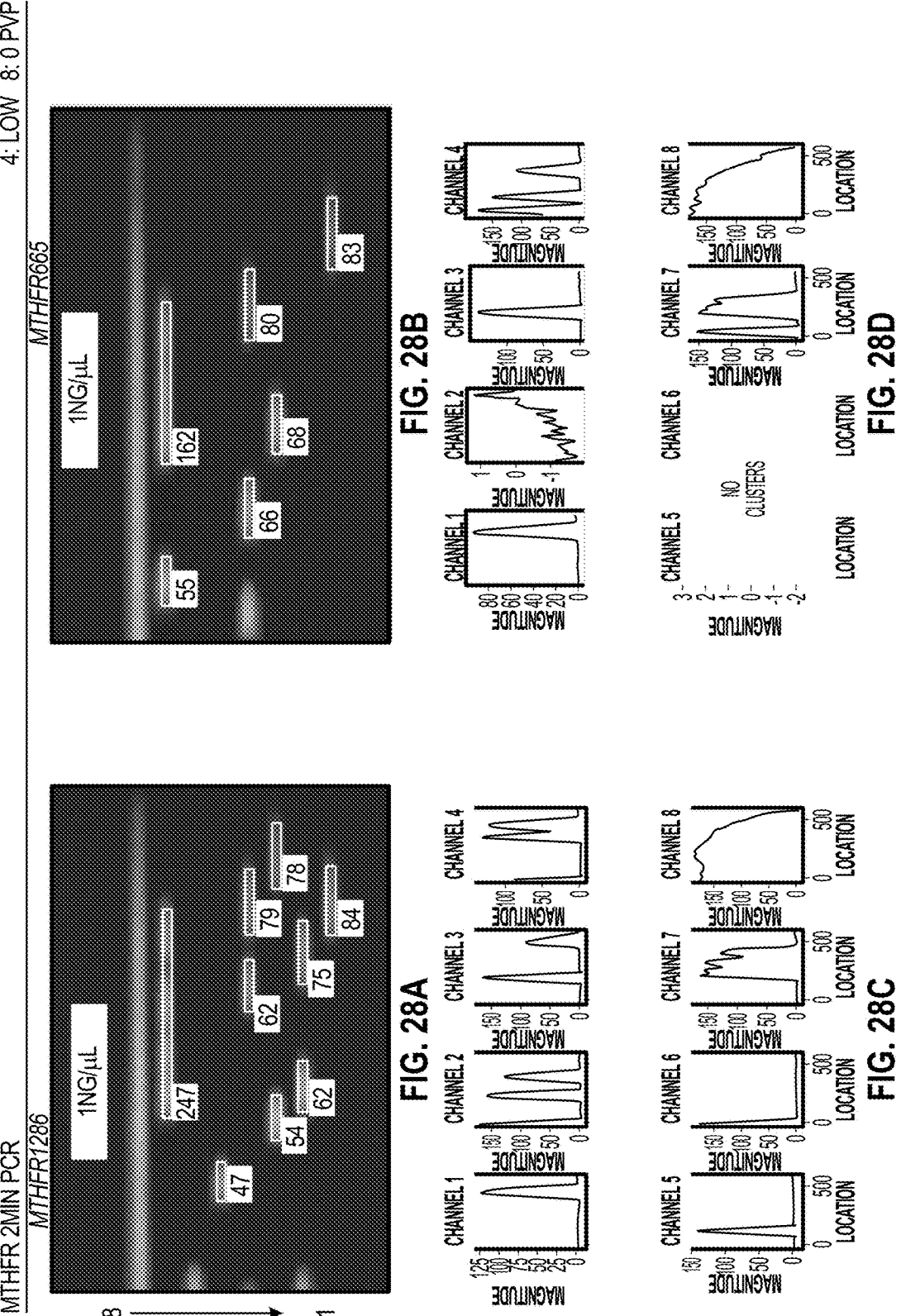
FIG. 28A-B are analyzed images of 8-channel cartridges.
FIG. 28C-D are charts for each channel of the cartridges showing DOE results with PVP for MTHFR coag assays at 2 minutes.
Figures 30A, 30B, 30C, 30D, 30E, 30F:
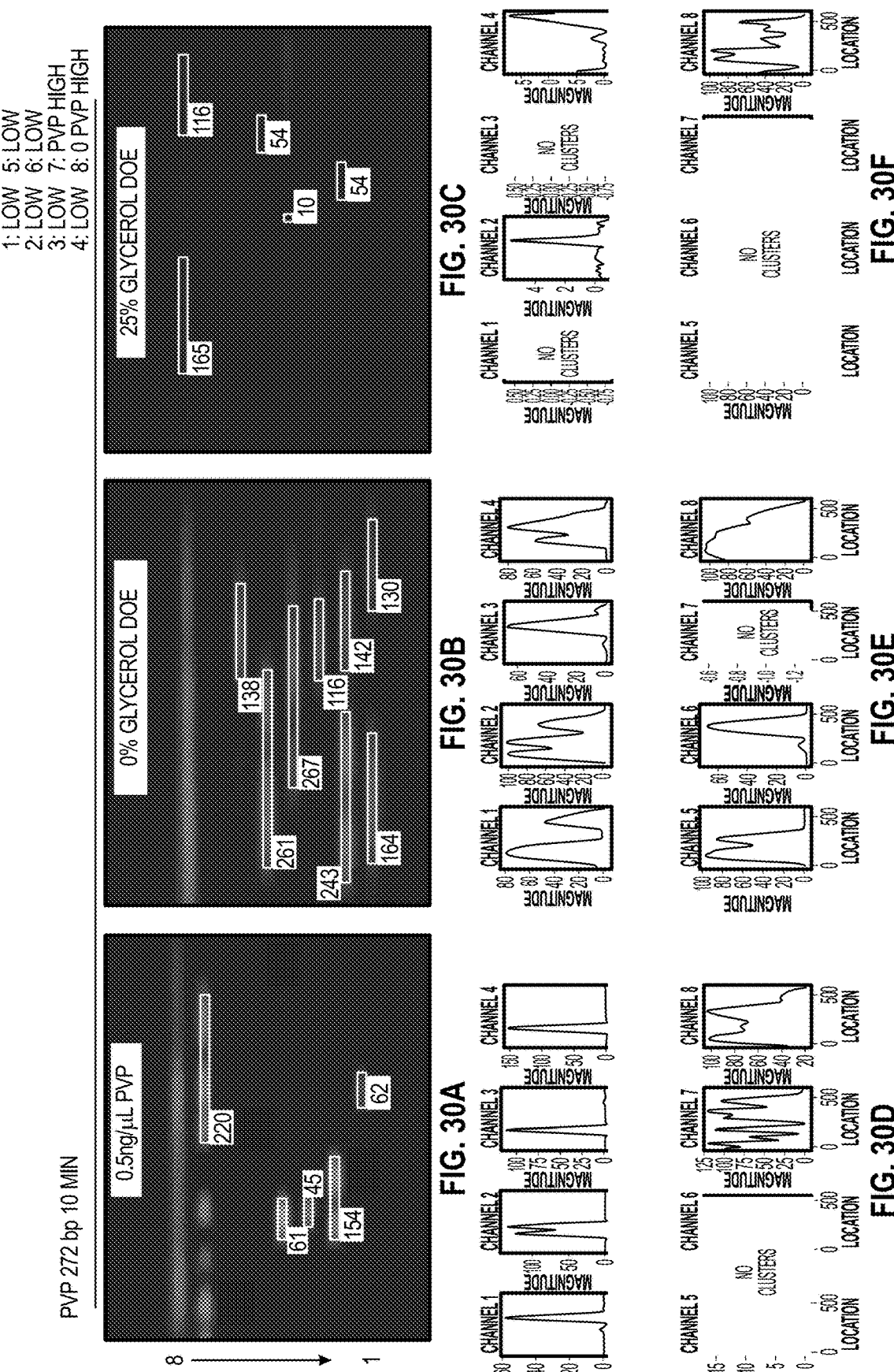
FIG. 30A-C are analyzed images of 8-channel cartridges.
FIG. 30D-F are charts for each channel of the cartridges showing DOE results with PVP for 272 bp assay at 10 minutes.

Initial testing was done using glycerol (1,2,3-propanetriol), a known PCR additive, to increase the viscosity of the solution. While amplicon cluster sizes were reduced, the glycerol resulted in a large shift in melting Tm of the amplicon as shown in FIG. 27. Additionally, the viscosity could not be increased further due to restraints in reaction volume. The additives Polyethylene Glycol (PEG), Polyvinylpyrrolidone (PVP), Methyl Cellulose, Ficoll, Alginic Acid Sodium Salt, Gelatin, Colloidal Silica, and Silk Fibroin (table 1) were additionally chosen for testing. Each chemical was dissolved in Nuclease Free $H_2O$ (NF $H_2O$) starting at 0.5% solution. The concentration was increased slowly until the sample could no longer be pipetted accurately with standard pipettes. This was determined to be the maximum solution concentration for each additive for these experiments. The NF $H_2O$ was boiled using a hot plate and the chemicals were slowly added into the beaker with constant stirring. Samples were cooled completely to properly test viscosity before increasing the concentration. Once the maximum concentration was determined, solutions were made in bulk, 50 mL, and stored until needed. The viscosity of each sample was measured at a later date with a viscometer (Rheosense Micro VISC with A05 chip, 0-100 cP). The viscosity data aligns with theory that larger, more complex molecular structures and higher molecular weight polymers will produce higher viscosities at lower concentrations in solution.

TABLE 1

Viscosity Increasing Additives

| Name | Company | Average Mol Wt (g/mol) | Catalogue Number |
|---|---|---|---|
| PEG | Sigma | 20,000 | 81300 |
| PVP | Sigma | 360,000 | PVP360 |
| Methyl Cellulose | Sigma | 63,000 | M0387 |
| Ficoll | Sigma | 400 | F2637 |
| Alginic Acid Sodium Salt | Sigma | 176.1 | A2033 |
| Gelatin | Sigma | 50,000 | G9391 |
| Colloidal Silica | Sigma | 60.08 | 420778 |
| Silk Fibroin | Canon Virginia, Inc. | 17,200 | Sample "G" |
| Glycerol | Sigma | 92.1 | G9012-1L |

TABLE 2

Maximum Solution Concentration and Viscosities of Each Additive

| Sample | Maximum Concentration (w/v) | Viscosity at 50% Max Concentration @ Room Temp (cP) |
|---|---|---|
| PEG | 20% | 14.99 |
| PVP | 5% | 8.56 |
| Methyl Cellulose | 1% | 7.03 |
| Ficoll | 20% | 4.93 |
| Alginic Acid Sodium Salt | 1% | NA |
| Gelatin | 1% | NA |
| Colloidal Silica | 50% | NA |
| Silk, Fibroin | 7.67% | 28 |
| Glycerol | 50% | 2.33 |

Figures 26A, 26B, 26C, 26D, 26E, 26F:
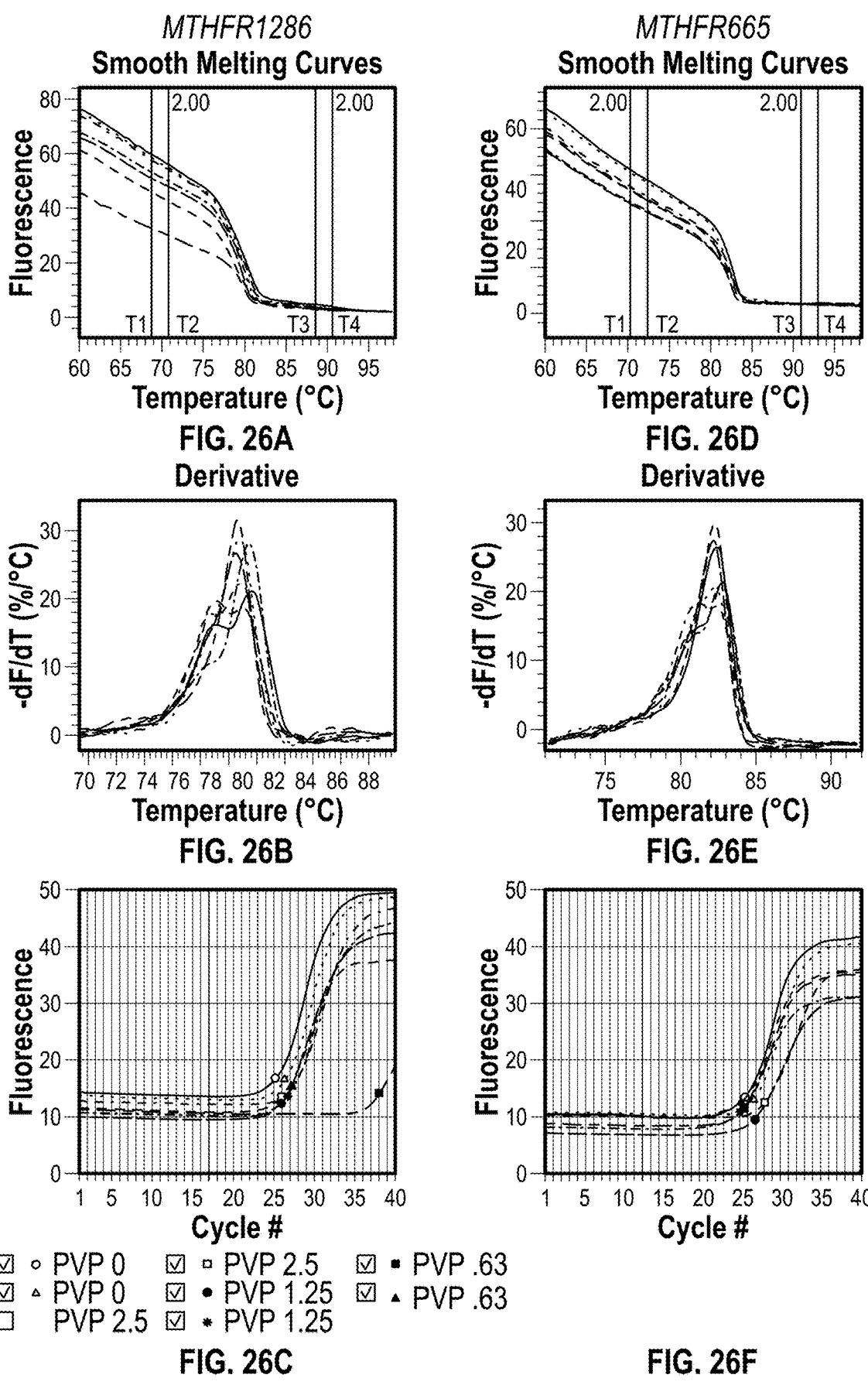
FIG. 26A-F are charts showing PGP results with a concentration gradient.

After the maximum concentration of each solution was determined, the additives were individually added to PCR reactions and tested on the BioRad CFX96 to ensure compatibility with PCR. Tests were done using 2-step PCR (Table 3), human genomic DNA and MTHFR665 primers. Master mixes of the PCR buffer were made according to the Initial PCR Chemistry table (Table 3A) at 2× concentration and diluted to 1× when mixed with various concentrations of each additive. Well plates were prepared as shown in Table 3, with two additives tested on each 96-well plate and 10 µL of PCR mix in each well. Each additive had a concentration gradient to determine the concentration at which each additive began to inhibit PCR. No template controls (NTCs) were not used in the initial testing. PCR efficiency (lowest Cq), Tm (minimum shift), and lowest concentration (w/v) to achieve high viscosity were observed.

istry, primer set, and DNA were used. Each additive was run on the same well plate, with 1 column as the 0% control, 1 column as the maximum concentration with DNA, and 1 column as the maximum concentration NTC. The samples were run with the same 2-step PCR protocol, except the anneal/extension step was held at a single temperature, 72° C. The results with NTCs are shown in FIG. 26. The NTCs did begin to amplify around cycle 37; however, they were a non-specific product that was seen in NTCs with 0% additives from previous experiments and they did not interfere with the data shown.

TABLE 3

Well Plate Map for PCR Additive Testing on BioRad CFX96

| | Additive 1 Concentration (% Maximum Concentration) | | | | | | Additive 2 Concentration (% Maximum Concentration) | | | | | | Anneal/Extension Gradient |
|---|---|---|---|---|---|---|---|---|---|---|---|---|---|
| | 1 | 2 | 3 | 4 | 5 | 6 | 7 | 8 | 9 | 10 | 11 | 12 | (° C.) |
| A | 0 | 3.1 | 6.3 | 12.5 | 25 | 50 | 0 | 3.1 | 6.3 | 12.5 | 25 | 50 | 74.0 |
| B | 0 | 3.1 | 6.3 | 12.5 | 25 | 50 | 0 | 3.1 | 6.3 | 12.5 | 25 | 50 | 73.5 |
| C | 0 | 3.1 | 6.3 | 12.5 | 25 | 50 | 0 | 3.1 | 6.3 | 12.5 | 25 | 50 | 72.4 |
| D | 0 | 3.1 | 6.3 | 12.5 | 25 | 50 | 0 | 3.1 | 6.3 | 12.5 | 25 | 50 | 70.4 |
| E | 0 | 3.1 | 6.3 | 12.5 | 25 | 50 | 0 | 3.1 | 6.3 | 12.5 | 25 | 50 | 68.0 |
| F | 0 | 3.1 | 6.3 | 12.5 | 25 | 50 | 0 | 3.1 | 6.3 | 12.5 | 25 | 50 | 66.0 |
| G | 0 | 3.1 | 6.3 | 12.5 | 25 | 50 | 0 | 3.1 | 6.3 | 12.5 | 25 | 50 | 64.7 |
| H | 0 | 3.1 | 6.3 | 12.5 | 25 | 50 | 0 | 3.1 | 6.3 | 12.5 | 25 | 50 | 64.0 |

Thermal Cycling Information
Hot Start: 95° C. for 30 s, Thermal Cycles: 95° C. for 1 s to 64/74° C. for 1 s - 35 cycles
Premelt: 95° C. for 2 s to 50° C. for 3 s, Melt 70-90° C. at 0.5° C. steps

TABLE 3A

PCR Chemistries

| | Initial PCR Chemistry | | Initial PGP Chemistry | | DOE Chemistry |
|---|---|---|---|---|---|
| Component | Final Concentration | Component | Final Concentration | Component | Final Concentration |
| Tris (8.3) | 50 mM | Tris (8.3) | 50 mM | Tris (8.3) | 50 mM |
| Mg2+ | 4.5 mM | Mg2+ | 4.5 mM | Mg2+ | 4.5 mM |
| Tween20 | 0.04% mM | Tween20 | 0.04% mM | Tween20 | 0.04 mM |
| BSA | 0.5 mg/mL | BSA | 0.5 mg/mL | BSA | 0.5 mg/mL |
| LCGreen+ | 1X | LCGreen+ | 1X | LCGreen+ | 2X |
| KlenTaq | 0.04 U/µL | KlenTaq | 0.04 U/µL | Klen Taq | 0.25 U/µL |
| Aptamer | 1 µM | Aptamer | 1 µM | Aptamer | 2 µM |
| dNTPs | 1.5 mM | dNTPs | 1.5 mM | dNTPs | 1.5 mM |
| Primers | 1 µM | Primers | 1 µM | Primers | 1 µM |
| DNA | 0.5 ng/µL | DNA | 10 ng/µL | DNA | ng/µL |

Figures 21A, 21B, 21C, 21D:
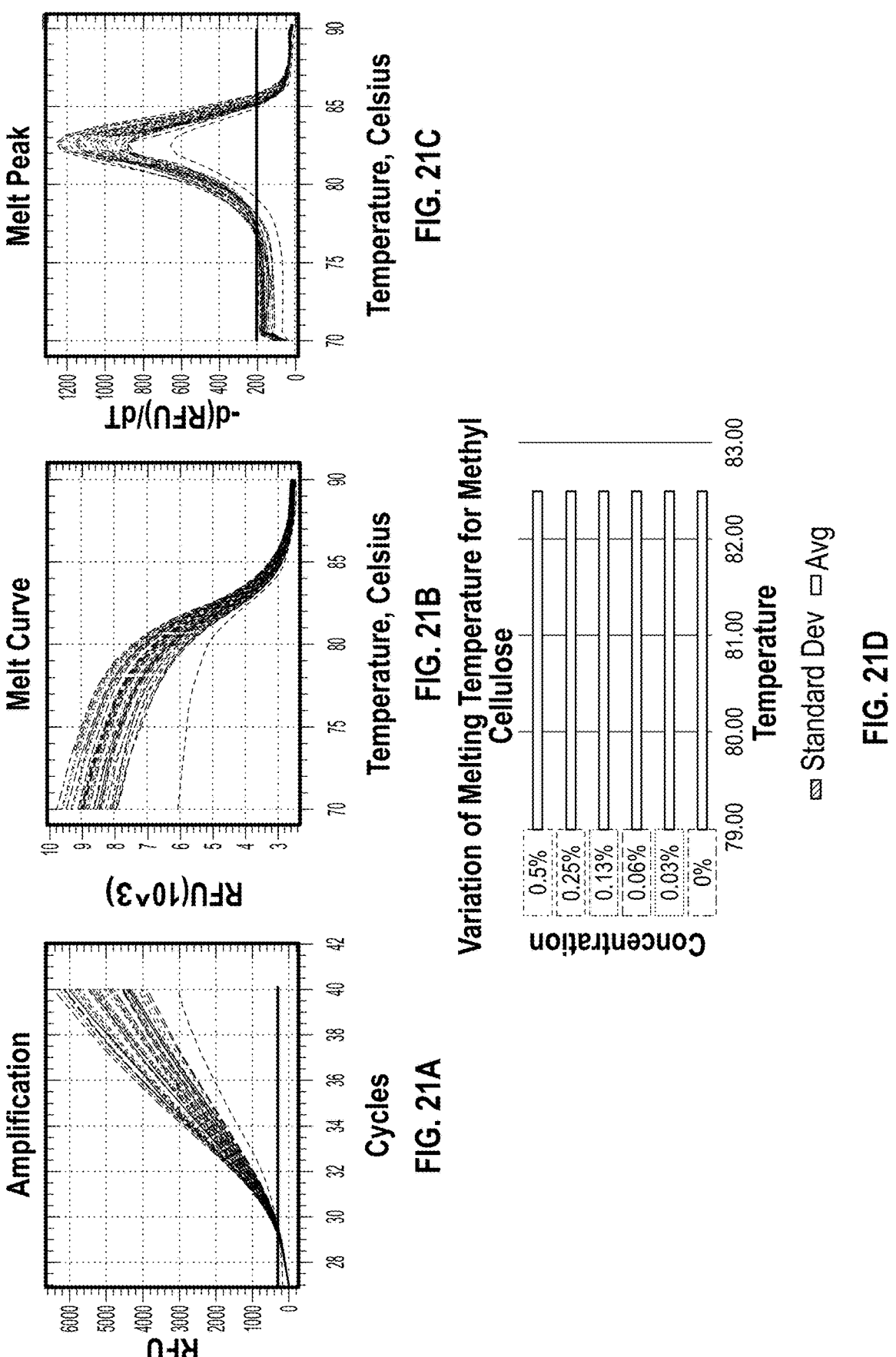
FIG. 21A-D are charts showing the BioRad results for Methyl Cellulose.
Figures 22A, 22B, 22C, 22D:
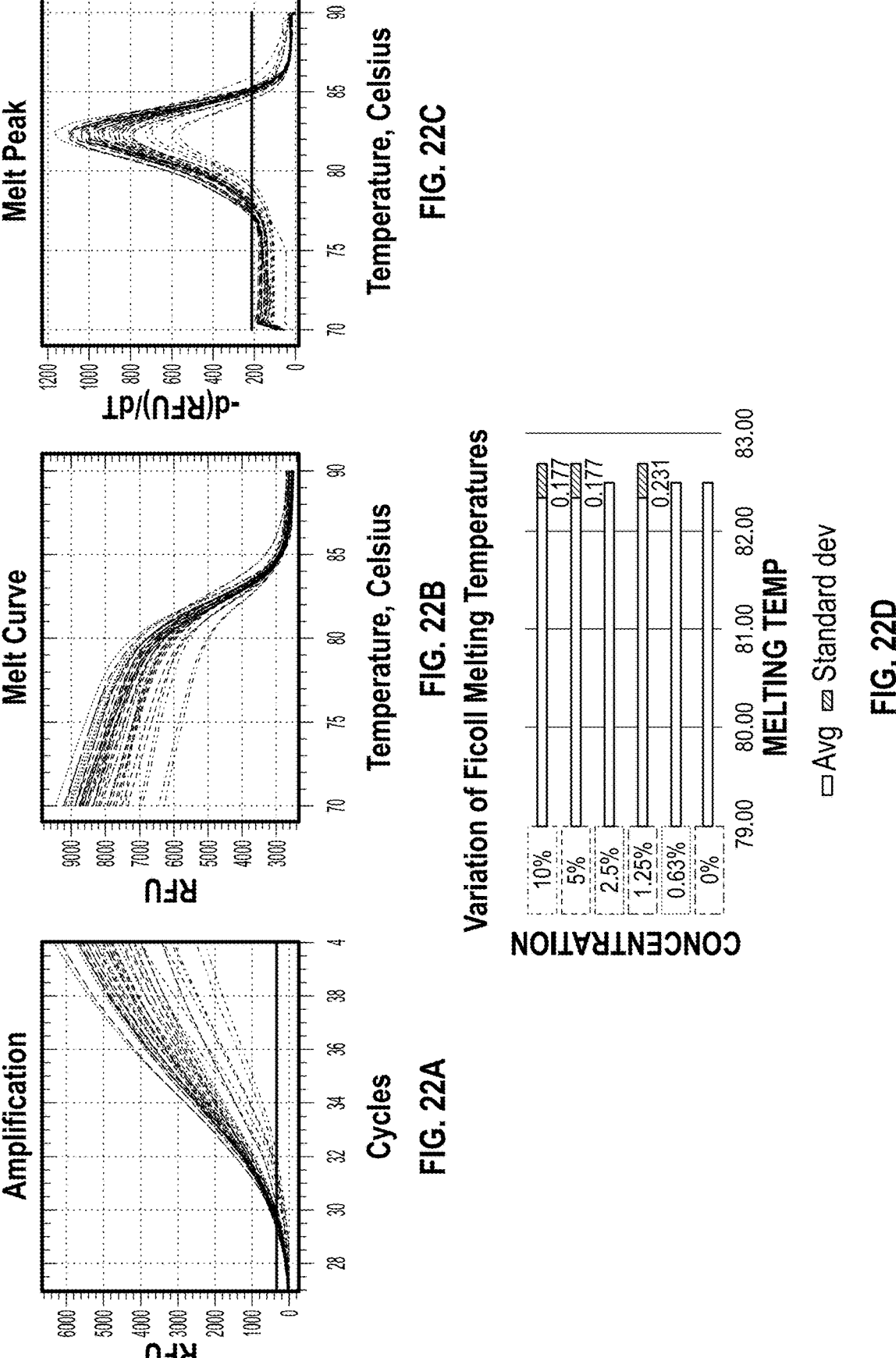
FIG. 22A-D are charts showing the BioRad results for Ficoll.
Figures 23A, 23B, 23C, 23D:
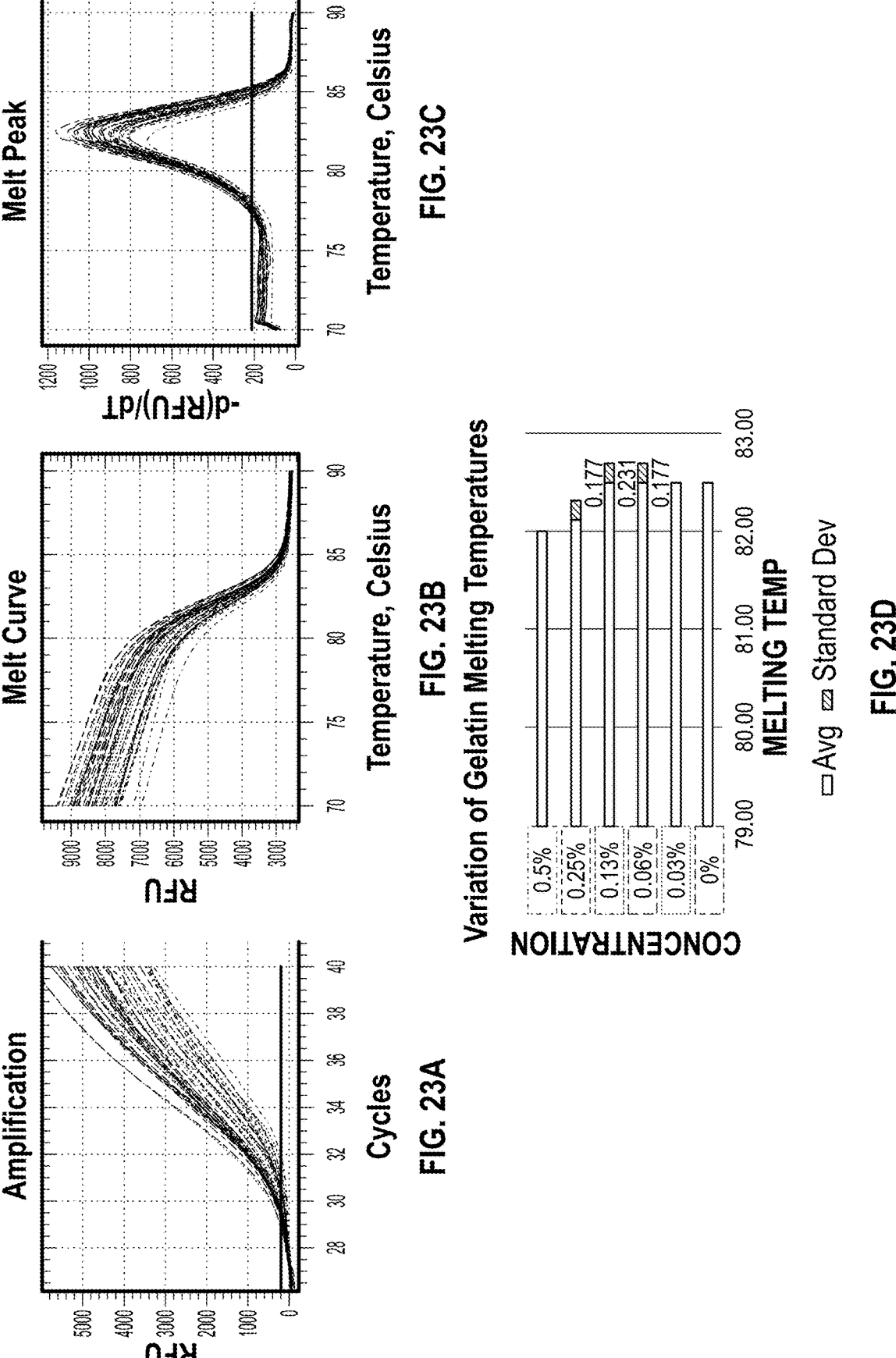
FIG. 23A-D are charts showing the BioRad results for gelatin.
Figures 24A, 24B:
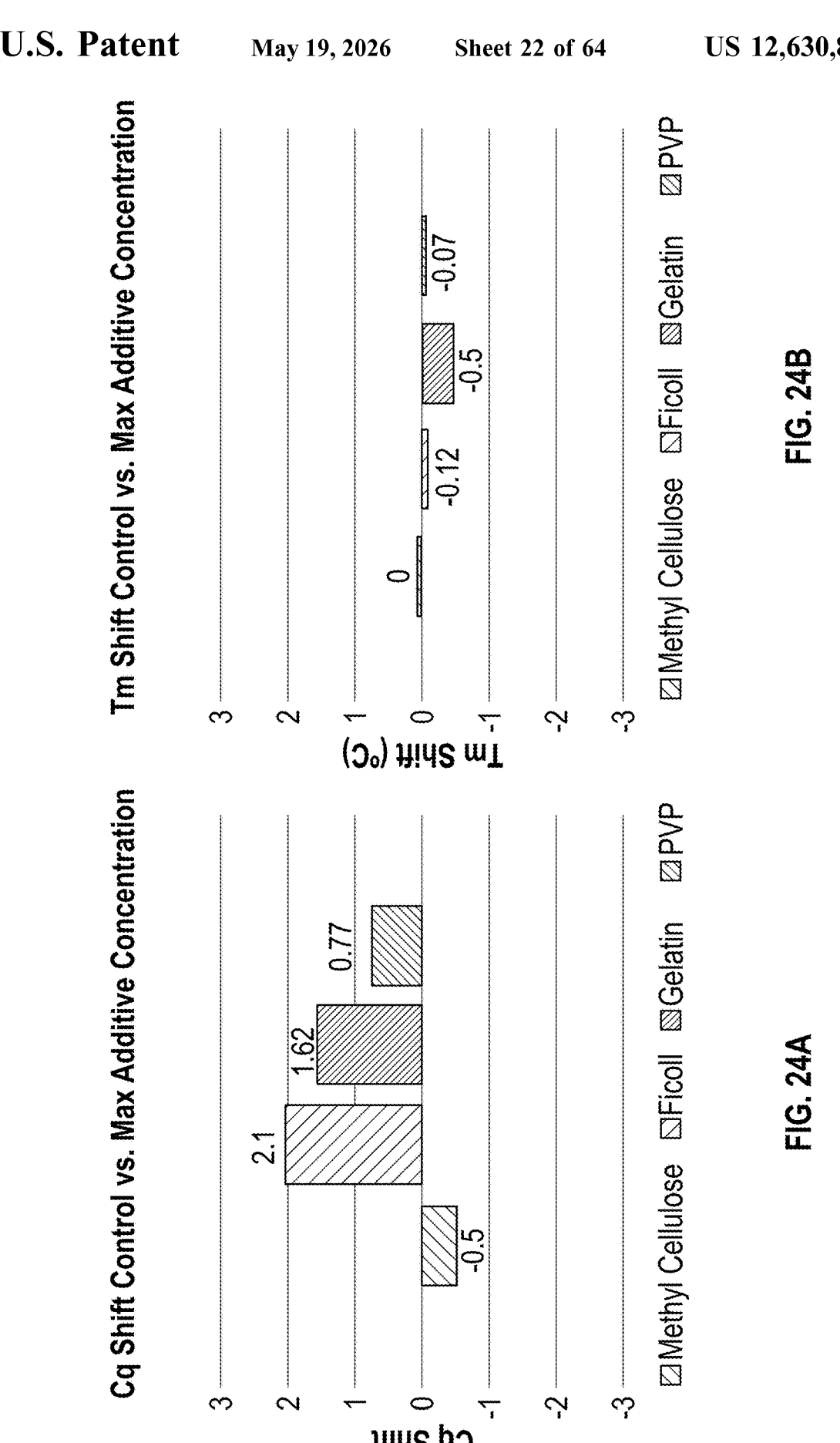
FIG. 24A-B are charts showing a comparison of PCR efficiency.

Methyl Cellulose was an efficient additive, as shown in FIG. 21. It had very little effect on PCR and no shift in Tm. PVP, Ficoll, and Gelatin all appeared to begin slightly inhibiting the PCR reaction at maximum concentration (FIGS. 20, 22 and 23). There was a slight increase in Cq values observed when compared to the 0% control (FIG. 25). Alginic acid, colloidal silica, PEG, and silk all showed various levels of PCR inhibition and/or shifts in Tm at the concentrations tested. Out of all of the additives, Methyl Cellulose was the only one to decrease the Cq value when compared to the 0% control as shown in FIG. 24. Methyl Cellulose, PVP, Ficoll, and Gelatin were chosen for further analysis.

The final four additives were tested again on the BioRad with NTCs and 0% controls to ensure that the additives did not lead to any non-specific amplification. The same chem-

TABLE 3B

PCR Settings

| | | Temperature (° C.) | Hold Time (s) | Ramp Rate (° C./s) | 35 Cycle Time (min) | 40 Cycle Time (min) |
|---|---|---|---|---|---|---|
| 2 Minute PCR Settings | Hot Start | 95 | 10 | 200 | 1.9 | 2.2 |
| | Denature | 95 | 0 | 200 | | |
| 40 Cycles | Anneal | 65 | 0 | 200 | | |
| | Extension | 65 | 2 | 200 | | |

TABLE 3B-continued

| | | Temperature (° C.) | Hold Time (s) | Ramp Rate (° C./s) | 35 Cycle Time (min) | 40 Cycle Time (min) |
|---|---|---|---|---|---|---|
| PCR Settings | | | | | | |
| 3 Minute PCR Settings | Hot Start | 95 | 10 | 200 | 2.5 | 2.9 |
| | Denature | 95 | 0 | 200 | | |
| | Anneal | 65 | 0 | 200 | | |
| | Extension | 65 | 3 | 200 | | |
| 4 Minute PCR Settings | Hot Start | 95 | 10 | 200 | 4.7 | 5.3 |
| | Denature | 95 | 0 | 200 | | |
| | Anneal | 65 | 3 | 200 | | |
| | Extension | 72 | 2.6 | 7 | | |

TABLE 3B-continued

| | | Temperature (° C.) | Hold Time (s) | Ramp Rate (° C./s) | 35 Cycle Time (min) | 40 Cycle Time (min) |
|---|---|---|---|---|---|---|
| PCR Settings | | | | | | |
| 10 Minute PCR Settings | Hot Start | 95 | 10 | 200 | 11.7 | 13.3 |
| | Denature | 95 | 0 | 200 | | |
| | Anneal | 65 | 3 | 200 | | |
| | Extension | 72 | 14.6 | 7 | | |

*The 4 and 10 minute PCR settings do not match the total PCR time for 40 cycles (or 35 cycles), because they were designed for 30 thermal cycles to match the simulation results. The amplicon clusters were not bright enough after 30 cycles during testing, so analysis was done after the 35th PCR cycle.

TABLE 4A

Well Plate Set-up for PGP Runs

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| A | 35 | 35 | 35 | | | | | | | | | | | | | | | | | | | | | 50 |
| B | µL | µL | µL | | | | | | | | | | | | | | | | | | | | | µL |
| C | Test 1 | Test 2 | Test 3 | | | | | | | | | | | | | | | | | | | | | SAMPLE |
| D | Primer | Primer | Primer | | | | | | | | | | | | | | | | | | | | | DNA |
| E | | | | | | | | | | | | | | | | | | | | | | | | |
| F | | | | | | | | | | | | | | | | | | | | | | | | |
| G | | | | | | | | | | | | | | | | | | | | | | | | |
| H | | | | | | | | | | | | | | | | | | | | | | | | |
| I | | | | | | | | | | | | | | | | | | | | | | | | 35 |
| J | | | | | | | | | | | | | | | | | | | | | | | | µL |
| K | | | | | | | | | | | | | | | | | | | | | | | | CALI- |
| L | | | | | | | | | | | | | | | | | | | | | | | | BRATOR |
| M | | | | | | | | | | | | | | | | | | | | | | | | |
| N | | | | | | | | | | | | | | | | | | | | | | | | |
| O | | | | | | | | | | | | | | | | | | | | | | | | |
| P | | | | | | | | | | | | | | | | | | | | | | | | |

TABLE 4B

Well Plate Set-up for PGP

| | | Test 1 | Test 2 | Test 3 |
|---|---|---|---|---|
| Speed Testing | Row A - 0% Max Additive Rows B-D - 50% Max Additive | Rows A-D MTHFR1286 | Rows A-D MTHFR665 | Rows A-D Buffer |
| | Rows E-G - 50% Max Additive Row H - 0% Max Additive | Rows E-H Buffer | Rows E-H MTHFR1286 | Rows E-H MTHFR665 |
| Methyl Cellulose 2 min PCR Testing | Row A - 0% Max Additive with 10 ng/µL DNA Rows B-D - 0% Max Additive with 0.5 ng/µL DNA Rows E-G - 0.5% methyl cellulose with 0.5 ng/µL DNA Row H - 0.5% methyl cellulose with 10 ng/µL DNA | MTHFR665 | MTHFR1286 | N/A |
| Methyl Cellulose 4/10 min PCR Testing | Row A - 0% Max Additive with 10 ng/µL DNA Rows B-D - 0% Max Additive with 0.5 ng/µL DNA Rows E-G - 0.5% methyl cellulose with 0.5 ng/µL DNA | CSP1 - 51 bp Assay | CSP1 - 100 bp Assay | CSP1 - 272 bp Assay |

TABLE 4B-continued

| Well Plate Set-up for PGP | | | | |
|---|---|---|---|---|
| | | Test 1 | Test 2 | Test 3 |
| PVP Testing 4/10 min PCR Testing | Row H - 0.5% methyl cellulose with 10 ng/µL DNA Rows A-F - 2.5% PVP with 0.5-1 ng/µL DNA Row G - 2.5% PVP with 10 ng/µL DNA Row H - 0% Max Additive with 10 ng/µL DNA | CSP1 - 51 bp Assay | CSP1 - 100 bp Assay | CSP1 - 272 bp Assay |
| 2 min PCR Low DNA Testing | Rows A-G - 2.5% w/v PVP with 0.5-1 ng/µL DNA Row H - 0% Max Additive with 10 ng/µL DNA | MTHFR665 | MTHFR1286 | N/A |

PGP-Increasing PCR Speed

After confirming that the additives work in the PGP and that the NTCs were clean, the PCR reactions were sped up. Maximum concentration for each additive was used along with a 0% control. Both primers were split into two separate tests to achieve two different PCR speeds in the same cartridge for a side-by-side comparison. To do this, primers were only used in channels 1-4 for the first test and the channels 5-8 in the second test. PCR was completed in two and three minutes as shown in Table 3B (2 Minute PCR Settings and 3 Minute PCR Settings). Results are shown in FIG. 32-34.

Figure 35:
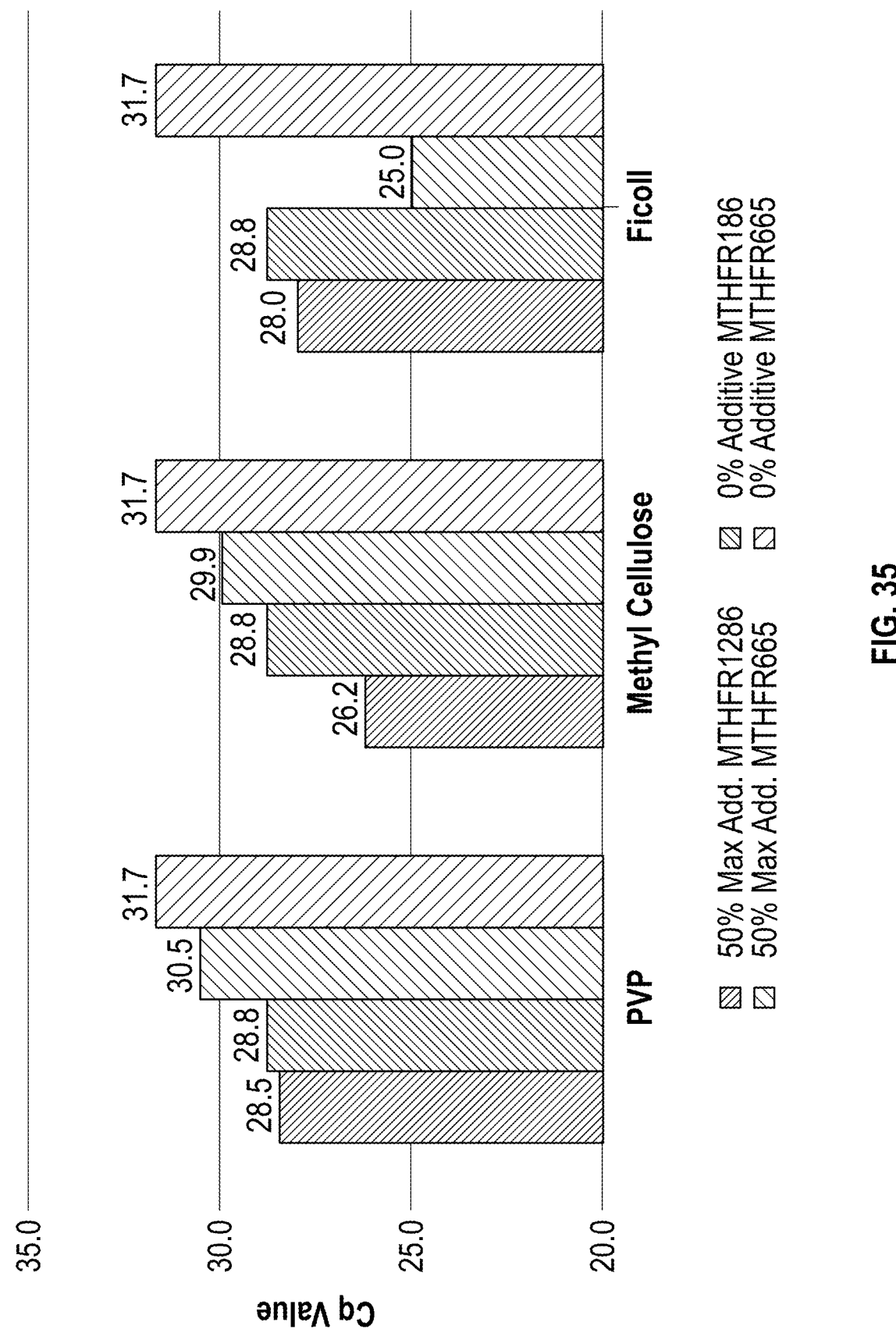
FIG. 35 is a chart showing a comparison of 2 minute PCR Cq results with additives.
Figure 41D:
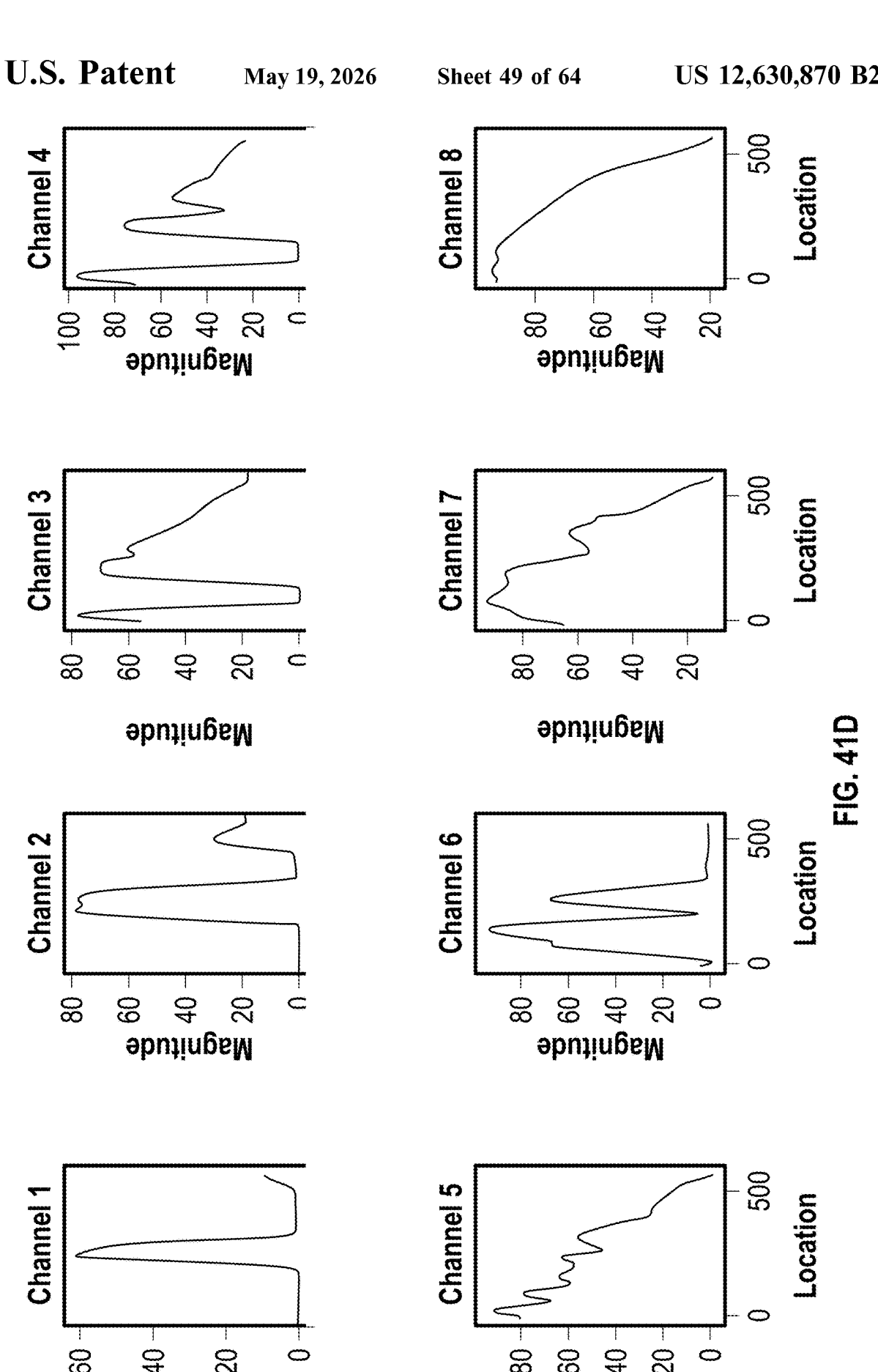
Figure 41E:
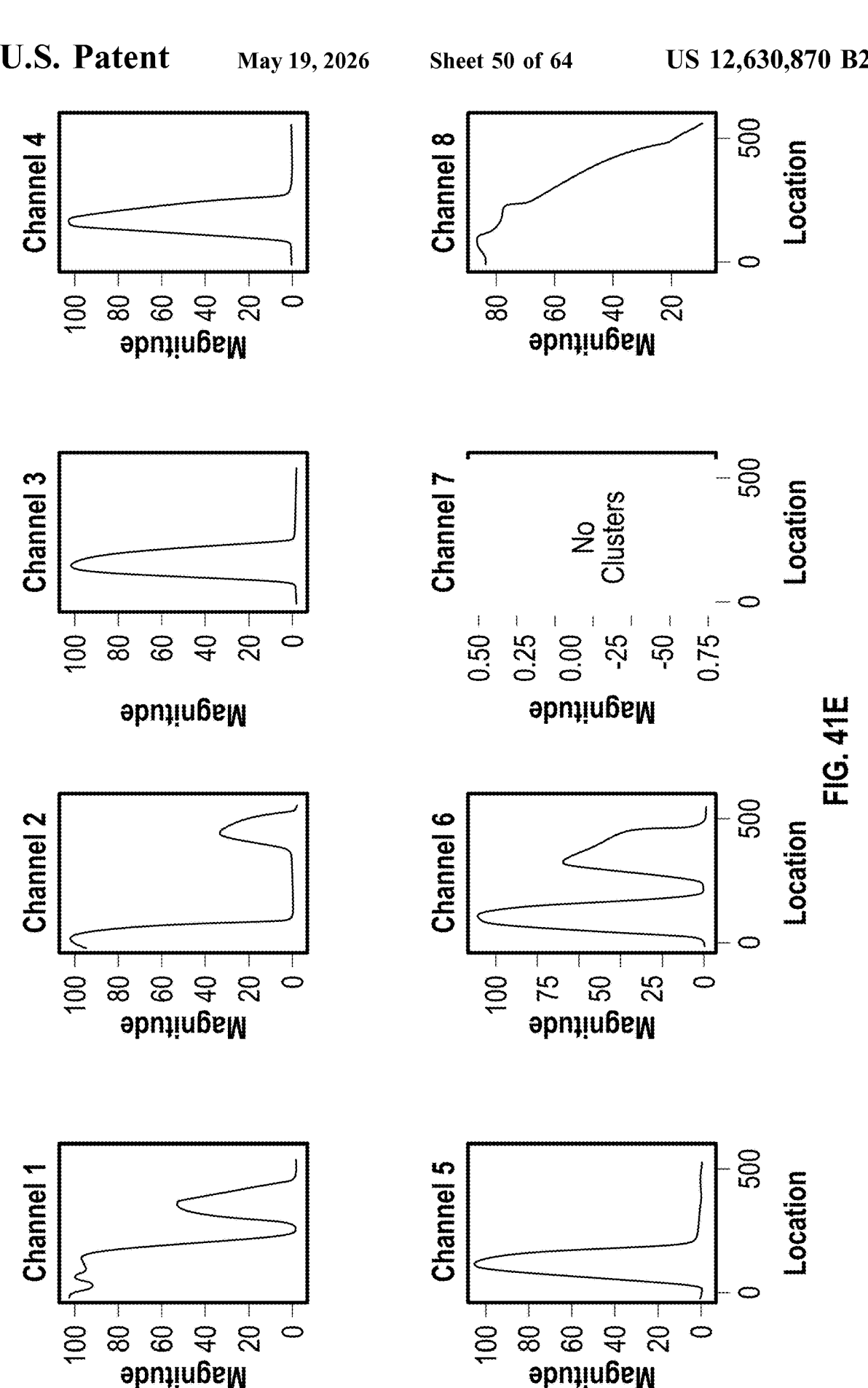
Figure 42D:
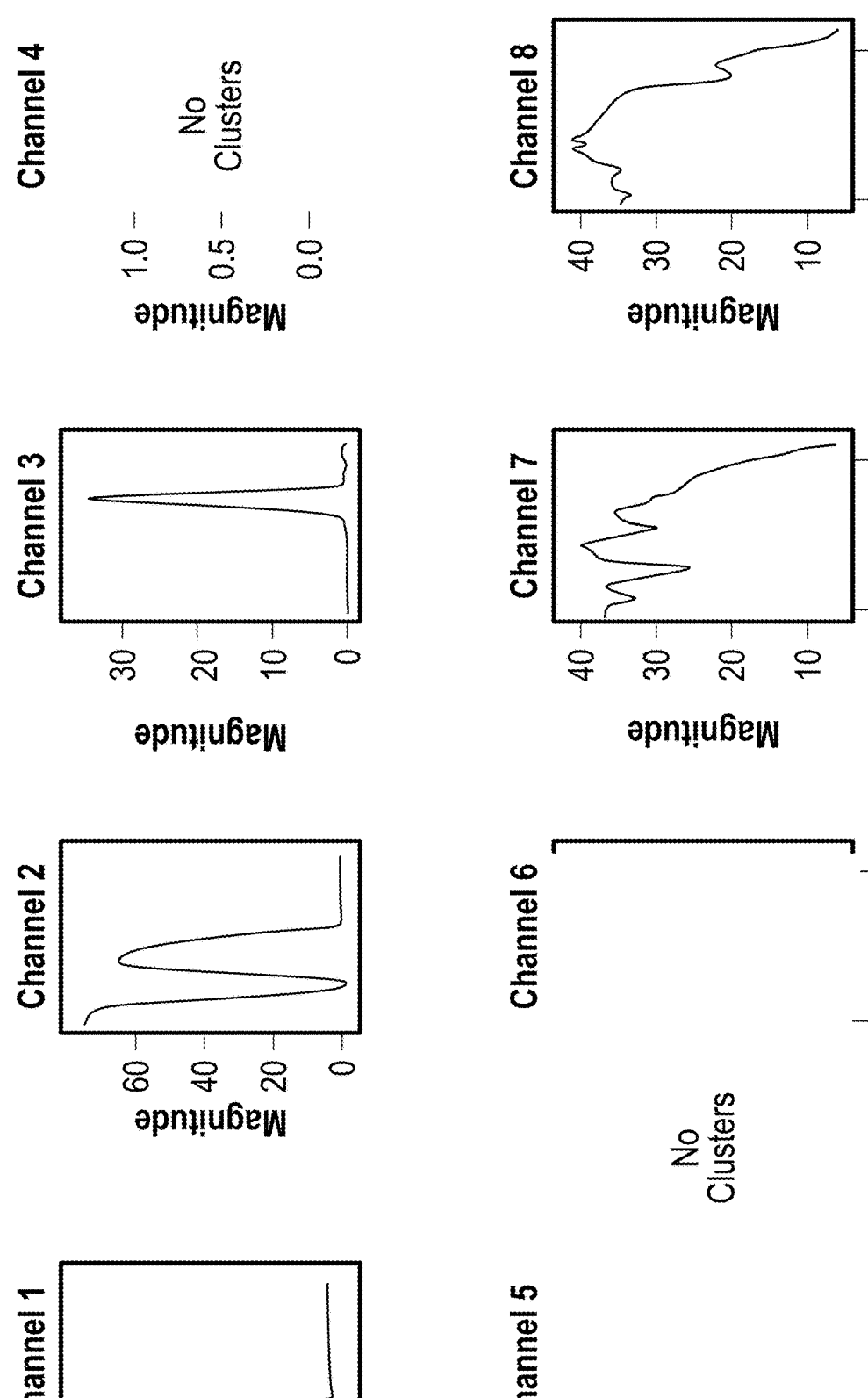
Figure 43C:
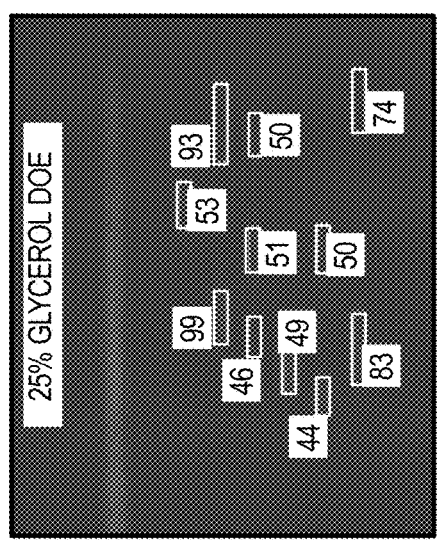
Figure 43B:
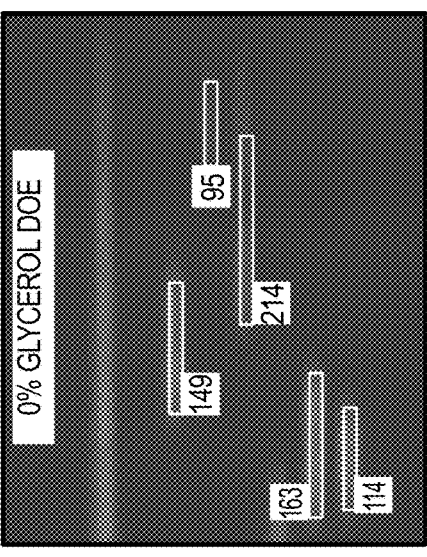
Figure 43A:
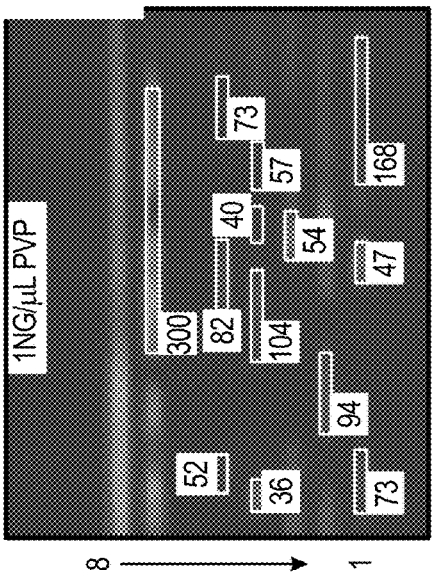
Figure 43D:
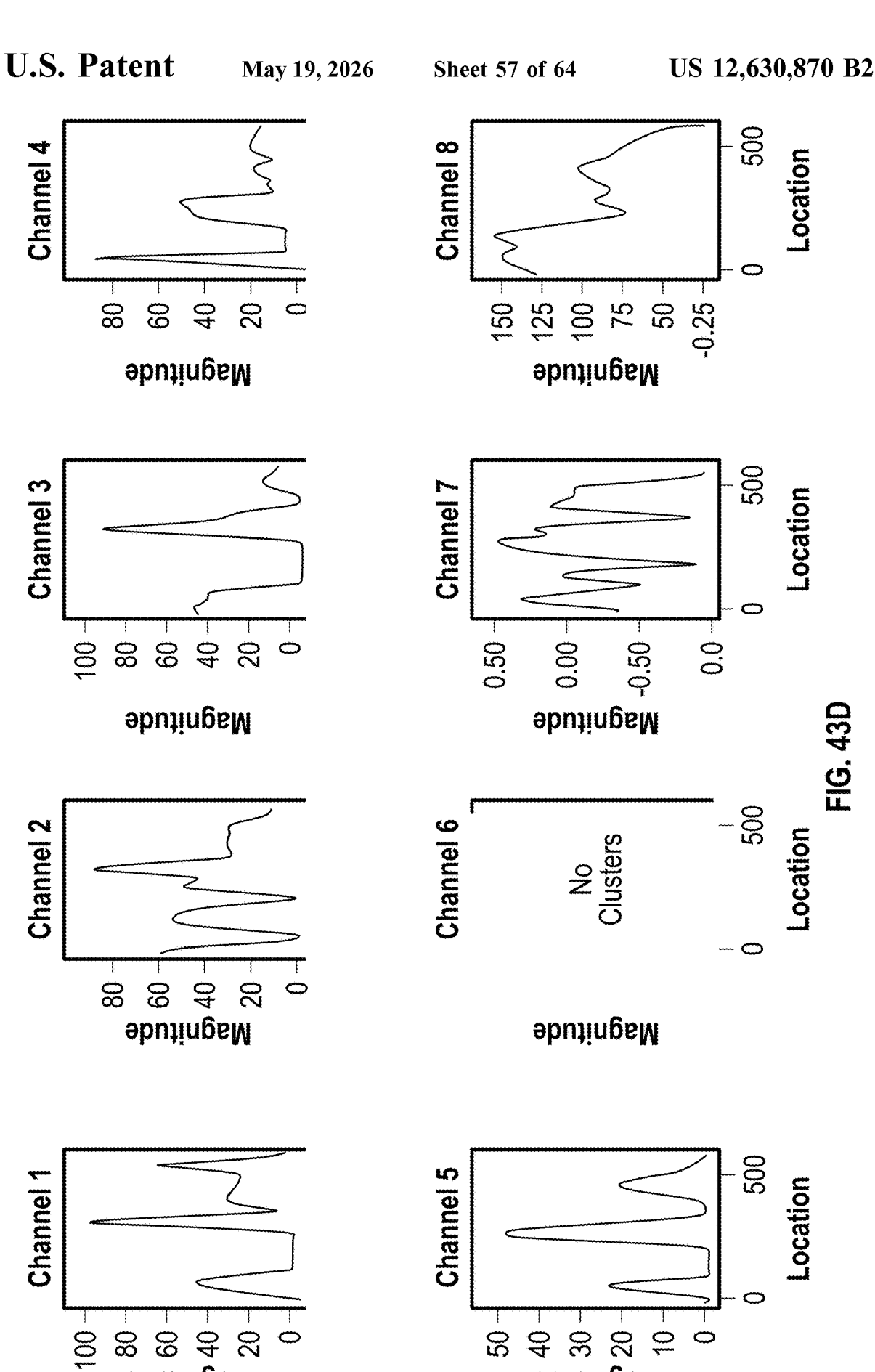
Figure 43E:
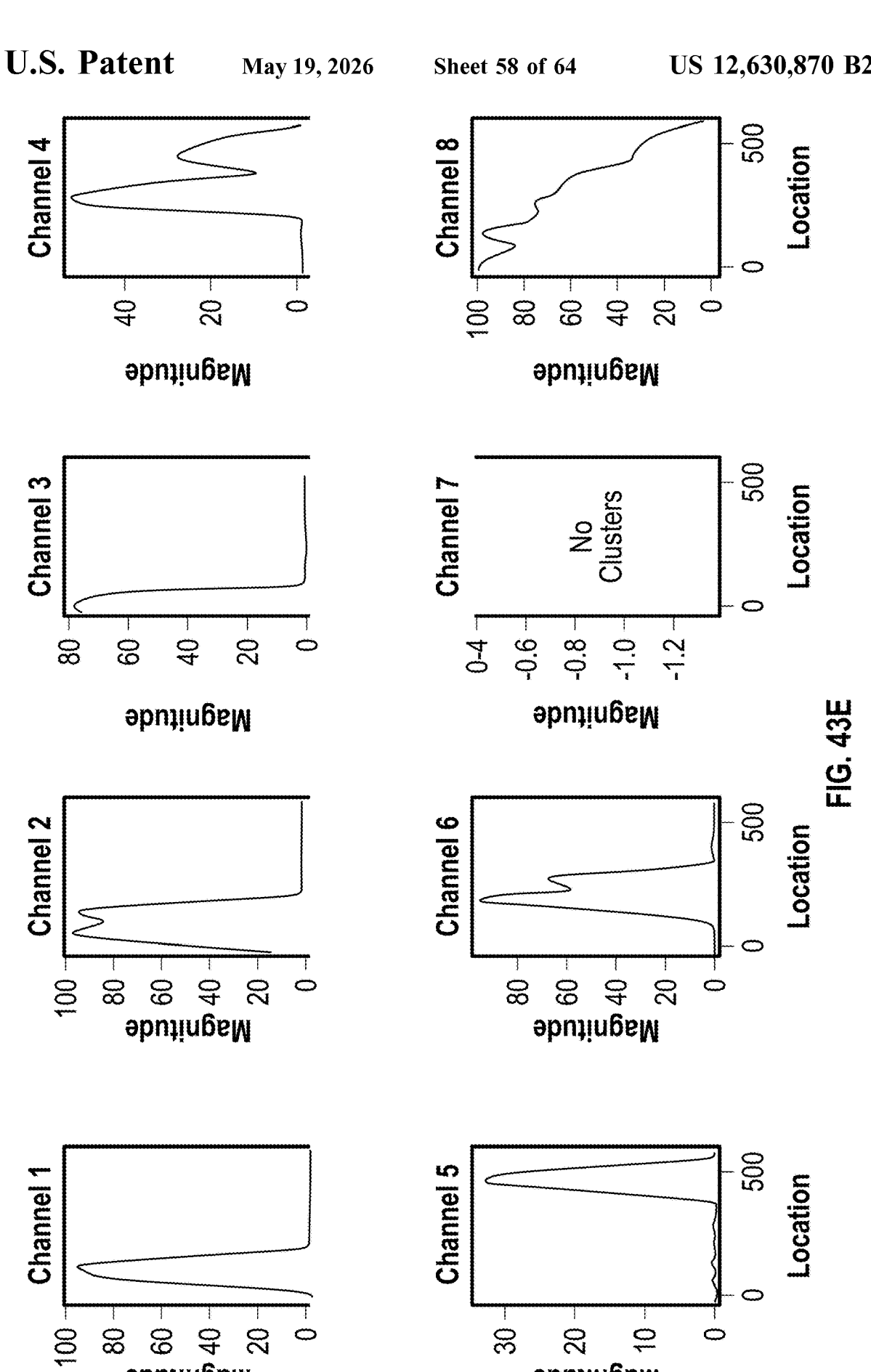
Figure 44D:
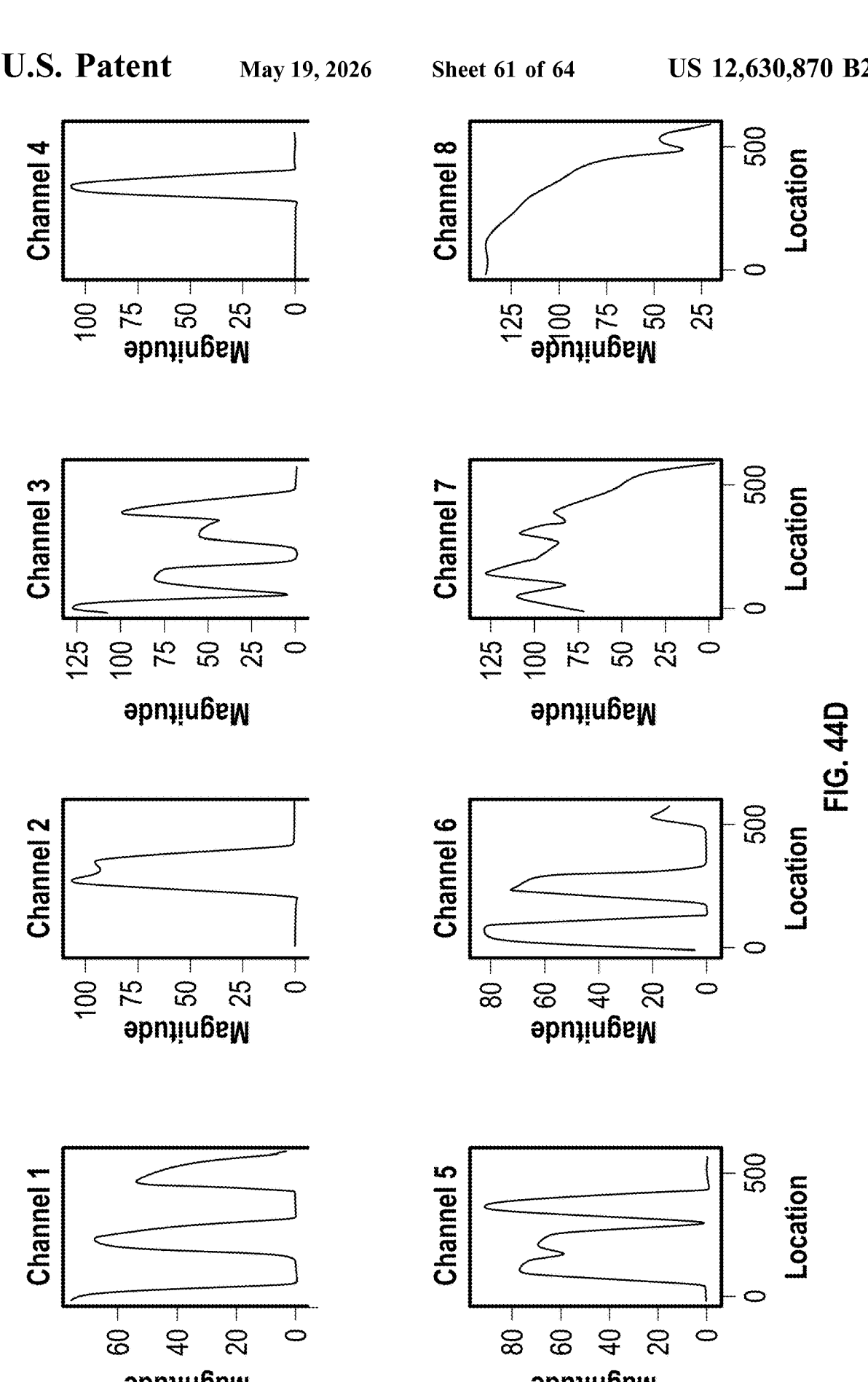
Figure 44E:
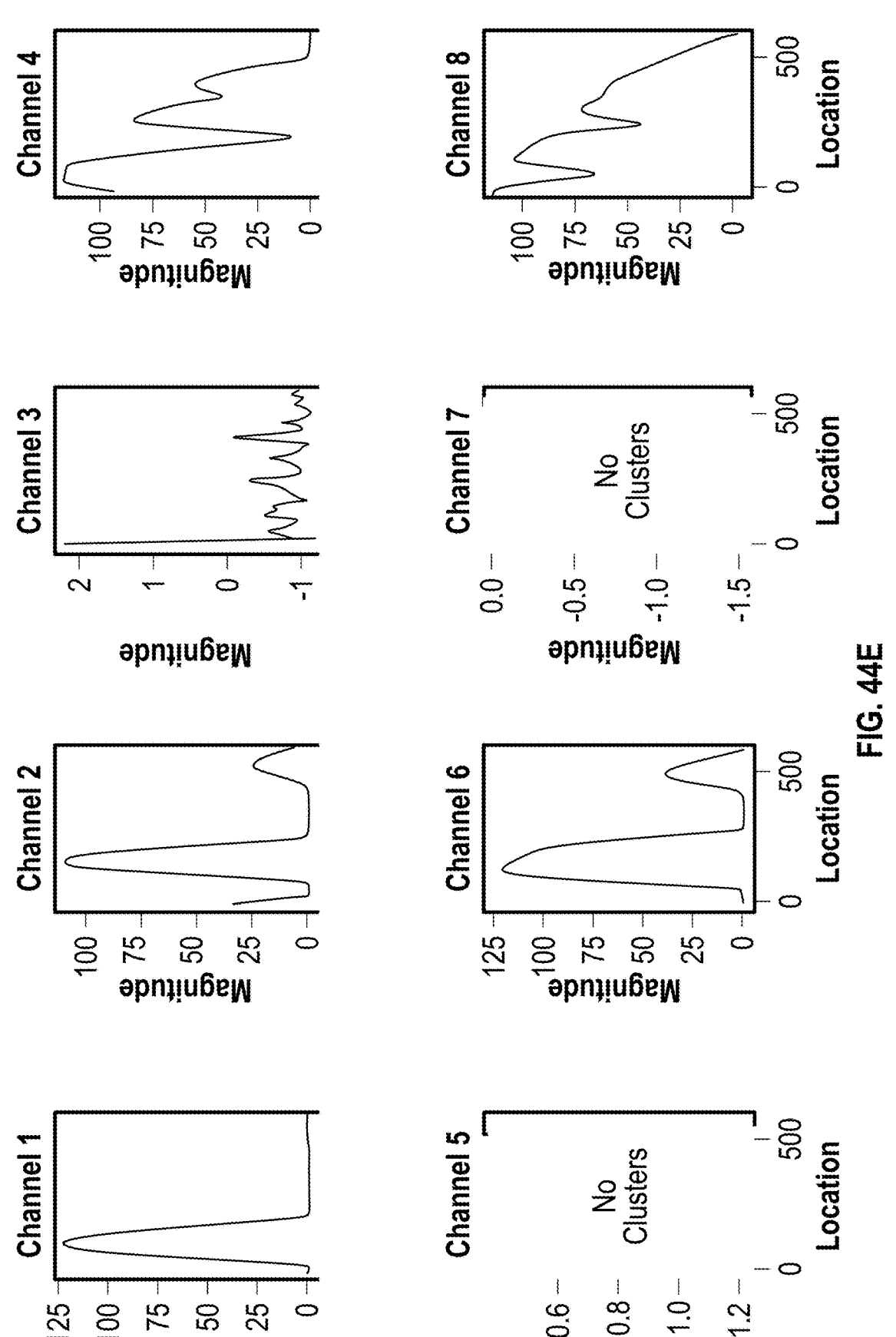

The Methyl Cellulose, Ficoll, and PVP all had similar results to the 0% additive controls. All three additives had slightly better Cq values for the 2-minute PCR when compared to the no additive controls (FIG. 35). All three additives seemed capable of withstanding the stress of faster PCR with minimal effect on efficiency. As PCR performance could not be used to separate the three remaining additives, methyl cellulose was selected for further testing due to the high viscosity observed at such low concentrations.

PGP-Low Vs High DNA with Methyl Cellulose

DNA was diluted from the 10 ng/µL used in previous reactions to 0.5 ng/µL to create a low DNA concentration sample. The high DNA concentration sample maintained the 10 ng/µL used previously and was used as a control. Dynamic slug control was turned off for these tests. This would allow clusters to form within the channels with the low DNA concentration. Both MTHFR1286 and MTHFR665 were tested with four channels containing no additive and four containing 0.5% methyl cellulose, with three channels at low DNA and one with high DNA concentration each (2 minute methyl cellulose settings in table 4B). This allowed the clusters generated in the low DNA samples with methyl cellulose to be compared to the 0% controls run on the same cartridge. The same PGP settings from the 2-minute PCR reactions were used for this experiment. Two tests were run to achieve reproducible results. There were a few channels that had no DNA detection; however, this was to be expected because of the low concentration and the small regions of interest (ROIs) being analyzed. HRM analysis was conducted with a custom HRM analysis software, which allows for the analysis of the full channel rather than a small ROI. All clusters had the same melting Tm, and multiple clusters can be seen in some channels (FIGS. 36, 37). The channels are in reverse order when compared to the original plate map (i.e. channel 1 for the analysis software is actually channel 8). PCR images from the 1$^{st}$ and 35$^{th}$ PCR cycle were identified, and cluster size analysis was performed. The cluster size differences were not significant when comparing the 0% and the 0.5% methyl cellulose samples. However, this data was obtained with faster PCR cycles, leaving less time for diffusion to make a difference.

PCR chemistry was prepared with new primers targeting CSP1 gene. The primers all target the same loci but generate four different product sizes, 51, 100 and 272 bp. Chemistry was the same as the previous tests except the LC Green concentration was increased from 1× to 2× and the KlenTaq concentration was increased from 0.04 to 0.15 U/µL (DOE Chemistry in Table 3A) to facilitate rapid PCR. The 51 and 100 bp CSP1 assays were used for the bulk of the data. The runs were randomized between the two assays, and the 4, and 10 minute PCR settings in Table 3B. The 0.5% methyl cellulose and a 0% control were both used at the low and high DNA concentrations in the previous test (4/10 minute methyl cellulose settings in Table 4B).

FIGS. 38 and 39 show the cluster size analysis for the low DNA concentration DOE, and the results are summarized in FIG. 40. The program used was unable to differentiate between clusters at times because they were too close together (e.g. Channel 8 from the 4 Minute 51 bp in FIG. 38). For the graphs in FIG. 40, clusters were ignored when multiple clusters clearly merged (histograms with shoulders or double peaks) or when clusters were too far to the right of the image (intensity too low). The analysis method along with the limited area led to few data points being collected. Based on the results, it was inconclusive if the methyl cellulose consistently reduced spot size. Spot size range for samples with Methyl Cellulose ranged from 1.3 mm to 1.8 mm. The size is about the same when compared to the 0% additive channels. These cluster sizes were much larger than anticipated, based on the research and viscosity measurements done regarding Methyl Cellulose.

PGP-Low Vs. High DNA with PVP

Figures 31A, 31B:
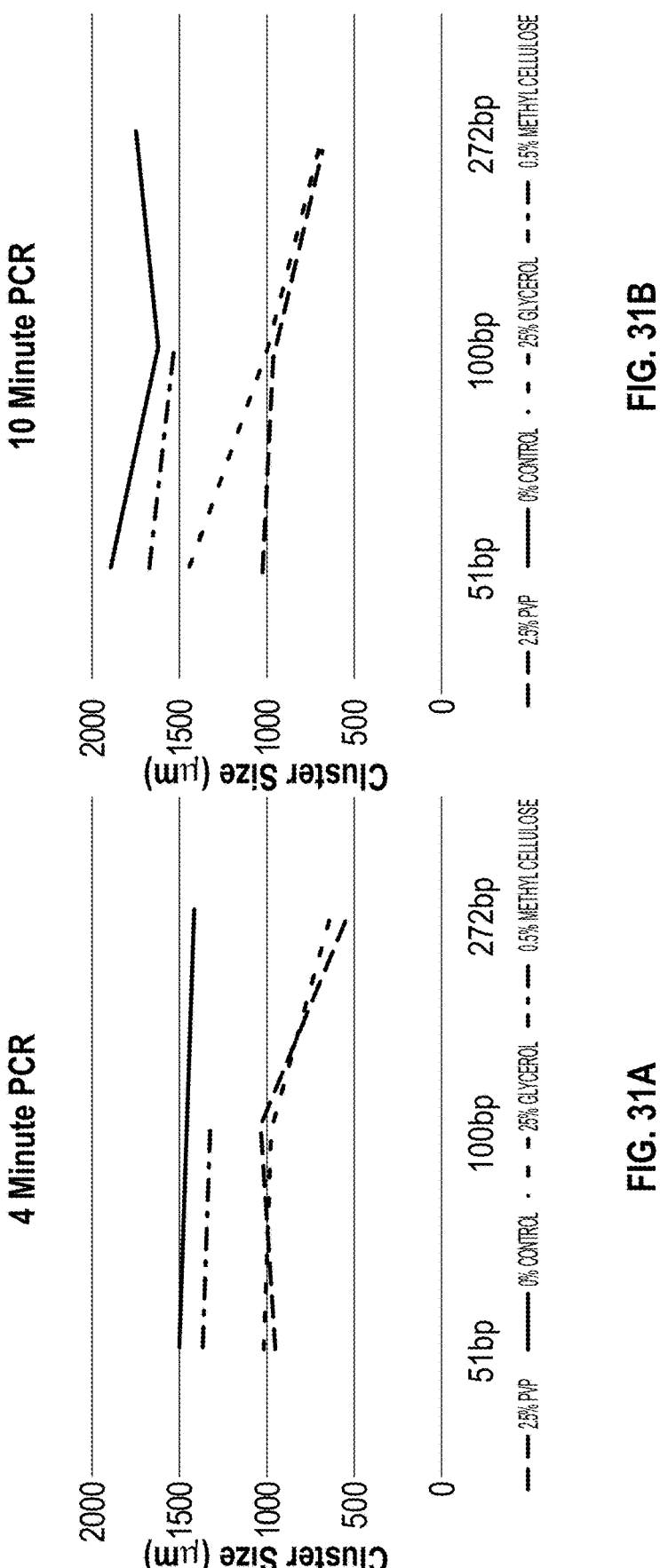
FIG. 31A-B are charts depicting cluster size vs PCR time and additive for PVP vs methyl cellulose vs glycerol

The same experimental methods and chemistry were used to determine the cluster sizes generated with PVP as the additive (4/10 minute PVP settings in Table 4B). After 1 round of experiments, the DNA concentration was increased to 1 ng/L in an attempt to get more clusters to appear. The cluster sizes from both rounds of experiments were averaged together when summarized. PVP had smaller cluster sizes than the 0% control and the 25% glycerol runs tested previously. FIGS. 28-30 and 41-44 show the analyzed images for each experimental condition as well as an additional 2 minute PCR assay testing the MTHFR primers (665 and 1286). FIG. 31 shows the average cluster size for the three CSP1 assays at 4 and 10 minute PCR settings with no additive, 2.5% PVP, 0.5% methyl cellulose, and 25% glycerol. FIG. 31 shows the average cluster size for the MTHFR assays with no additive and 2.5% PVP. Even with higher DNA concentrations (10 ng/μL), it is evident that clusters are forming. This is most prevalent in FIG. 30, channel 7.

What is claimed is:

1. A method for diffusion-controlled quantification of molecules comprising the steps of:

introducing a sample into a chamber; wherein the sample comprises primers, amplification reagents, and one or more nucleic acids, and wherein the nucleic acids are distributed across the chamber;

providing a thermal system in thermal communication with the sample;

providing an optical system in optical communication with the sample comprising one or more nucleic acids, wherein the optical detection system comprises an optical sensor;

performing amplification of the one or more nucleic acids;

actively controlling the diffusion of the amplified sample within the chamber such that an amplification spot is formed at each location of a nucleic acid that underwent amplification;

obtaining one or more images of the amplification spots;

digitally quantifying the amplified nucleic acids based on fluorescence distribution of the amplification spots across the chamber;

wherein, digitally quantifying the amplified nucleic acids comprises:

analyzing the one or more images to determine full-width-half-maximum (FWHM) cluster boundaries that are indicative of single amplification spots;

counting positive and negative spots based on the FWHM cluster boundaries, and, using a ratio of the positive and negative spots in the chamber to estimate quantification (λ).

2. The method of claim 1, wherein the amplification is selected from polymerase chain reaction and isothermal amplification.

3. The method of claim 1, wherein actively controlling the diffusion of the sample is selected from the group consisting of: adding a viscosity increasing agent to the sample, increasing the amplified molecule size, reducing the temperatures that the sample is subjected to during the amplification, and reducing the length of time of the amplification.

4. The method of claim 3, wherein the reducing the length of time of the amplification comprises minimizing the number of amplification cycles or performing thermal cycling.

5. The method of claim 4, wherein reducing the length of time of the amplification causes the amplified nucleic acids to remain spatially close to an initially amplified nucleic acid in the sample.

6. The method of claim 3, wherein the viscosity increasing agent is selected from the group consisting of:

thixotropic, emollient, gellant, cross-linking, and other rheology modifying and thickening agents.

7. The method of claim 1, wherein the chamber has dimensions of up to 0.1 mm×1 mm×10000 mm.

8. The method of claim 7, wherein the chamber is a three-dimensional shape, and the imaging system is configured to image spatial sections of the chamber independently.

9. The method of claim 7, wherein the chamber is a microfluidic channel having cross sectional dimensions that minimize stacking of starting seed molecules.

10. The method of claim 1, wherein there is minimal flow of the sample in the chamber to reduce diffusion between amplified nucleic acids.

11. The method of claim 10, wherein the chamber has a uniform temperature distribution to decrease convectional flow of the sample in the chamber.

12. The method of claim 3, wherein means for reducing the length of time of the amplification are selected from the group consisting of: obtaining images of the amplified nucleic acids early in the amplification process, providing a high-contrast reporter dye in the sample, and providing a thermal system that uses (i) hot air, (ii) optical heating methods, (iii) in-line resistive heaters, (iv) inductive heating, and/or (v) circulating heated fluid.

13. The method of claim 12, wherein obtaining images of the amplified nucleic acids early in the amplification process comprises using a low-noise imaging system to detect a positive fluorescence signal from the amplified nucleic acids.

14. The method of claim 3, wherein means for accelerating thermal cycling is selected from the group consisting of: providing a thermal system that utilizes direct optical, indirect optical or electromagnetic radiation based heating.

15. The method of claim 1, additionally comprising the step of performing a melting analysis.

16. The method of claim 15, further comprising obtaining melting curves for the one or more amplified nucleic acids.

17. The method of claim 16, further comprising genotyping the one or more nucleic acids.

18. The method of claim 17, wherein the digital quantification and genotyping results are combined to provide the allelic frequency of mutant DNA copies in the background of wild type DNA copies.

19. The method of claim 2, wherein the polymerase chain reaction is fast PCR.

20. The method of claim 1, wherein digital quantification includes counting a number of amplified spots or unamplified spots and applying statistics to calculate the number of DNA copies present in the chamber volume.

21. The method of claim 20, wherein digital quantification includes measuring overall area of amplified/unamplified spots.

22. The method of claim 1, wherein the optical detection system comprises (i) fluorescence imaging; or (ii) bright or dark field imaging, wherein the bright or dark field imaging is assisted by enhanced scattering or phase-contrast imaging.

23. The method of claim 22, wherein the imaging system visualizes amplified spots by fluorescence detection either during amplification or at the end of amplification.

24. The method of claim 23, wherein following visualization of the amplified spots, the amount of fluorescence is measured.

25. The method of claim 1, wherein digital quantification includes measuring overall fluorescence intensity of fluorescence images or an intensity of positive/negative signals generated by other optical techniques.

26. The method of claim 1, wherein digital quantification includes combining (i) counting amplified/non-amplified spots and (ii) spot intensity generated by fluorescence or other optical techniques.

27. The method of claim 11, further comprising an optical heating method that comprises using photonic gold as a photothermal medium to provide uniform light-to-heat conversion.

28. The method of claim 1, further comprising providing one or more labeled probes, wherein following amplification of the sample, the digital quantification additionally comprises using multicolor detection to determine one or more genotypes of the amplified nucleic acids.

29. The method of claim 28, additionally comprising determining the allele frequency.

* * * * *